US007585501B2

(12) United States Patent
Krumlauf et al.

(10) Patent No.: US 7,585,501 B2
(45) Date of Patent: Sep. 8, 2009

(54) COMPOSITIONS AND METHODS FOR TREATING KIDNEY DISEASE

(75) Inventors: Robb Krumlauf, Kansas City, MO (US); Debra Ellies, Kansas City, MO (US)

(73) Assignee: Stowers Institute for Medical Research, Kansas City, MO (US)

( * ) Notice: Subject to any disclaimer, the term of this patent is extended or adjusted under 35 U.S.C. 154(b) by 0 days.

(21) Appl. No.: 11/613,658

(22) Filed: Dec. 20, 2006

(65) Prior Publication Data

US 2007/0298038 A1 Dec. 27, 2007

Related U.S. Application Data

(63) Continuation-in-part of application No. 11/508,701, filed on Aug. 23, 2006, which is a continuation-in-part of application No. 10/464,368, filed on Jun. 16, 2003.

(60) Provisional application No. 60/710,803, filed on Aug. 23, 2005, provisional application No. 60/388,970, filed on Jun. 14, 2002.

(51) Int. Cl.
*A61K 39/395* (2006.01)
*C07K 16/00* (2006.01)
*C07K 16/28* (2006.01)

(52) U.S. Cl. .............. 424/130.1; 424/141.1; 424/144.1; 530/387.1; 530/388.1; 530/388.2

(58) Field of Classification Search .................. None
See application file for complete search history.

(56) References Cited

U.S. PATENT DOCUMENTS

| 5,780,263 | A  | 7/1998 | Hastings et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,803,453 | B1 | 10/2004 | Brunkow et al. |
| 6,875,570 | B2 | 4/2005 | Gerlach et al. |
| 2008/0160060 | A1 | 7/2008 | Ellies |

FOREIGN PATENT DOCUMENTS

WO   WO 00/32773   6/2000

OTHER PUBLICATIONS

Mizuno et al., J. Clin. Invest., 1998, 101: 1827-1834.*
Lederman et al., Molecular Immunology 28: 1171-1181, 1991.*
Li et al., PNAS 77: 3211-3214, 1980.*
Capecchi, 1994, Scientific American, pp. 52-59.
Brunkow, et al., US 2003/0166247 A1.
Houdebine, 1994, J. Biotech, 34, pp. 269-287.
Wall, Theriogenology, 45:57-68, 1996.
Niemann, Transg. Res., 7:73-75, 1998.
Keri et al., PNAS, 97(1):383-38, 2000.
Brunkow et al., Am. J. Hum. Genet., 68:577-589, 2001.
Balmain et al., Trends in Genetics, 14(4):139-144, 1998.
Cameron, Molec. Biol., 7:253-265, 1997.
Aubin, J.E., et al., Monoclonal Antibodies as Tools for Studying the Osteoblast Lineage, Microscopy Research and Technique, 33:128-140 (1996).
Bachiller, D., et al., The organizer factors Chordin and Noggin are required for mouse forebrain development Nature, vol. 403 (Feb. 10, 2000).
Balemans, W., et al., Extracellular Regulation of BMP Signaling in Vertebrates: A Cocktail of Modulators, Developmental Biology 250:231-250 (2002).
Balemans, W.. et al.. Increased bone density in sclerosteosis is due to the deficiency of a novel secreted protein (SOST), Human Molecular Genetics, vol. 10 (5): 537-543 (2001).
Bork, P., The modular architecture of a new family of growth regulators related to connective tissue growth factor, FEBS Letters 327(4125-130 (Jul. 1993).
Boyden, L.M., et at, High Bone Density Due to a Mutation in LOL-Receptor-Related Protein 5, The New England Journal of Medicine. vol. 348(20). pp. 1513-1521 (May 16, 2002).
Bruder, S.P., et al., Monoclonal Antibodies Reactive With Human Osteogenic Cell Surface Antigens, Elsevier, Bone vol. 21, No. 3:225-235 (Sep. 1997).
Brunkow. M.E., et al, Bone Dysplasla Sclerosteosis Results from Loss of the SOST Gene Product, a Novel Cystine Knot-Containing Protein, Am. J. Hum. Genet. 68:577-589 (2001).
Chen, X., et al.. Thy-1 Antigen Expression by Cells in the Osteoblast Lineage, Journal of Bone and Mineral Research, 14(3): 362-375 (1999).
Dewitt, N., Bone and Cartilage, Nature 423:315 (May 2003).
Ellies, D.L., et al., Novel Wnt Inhibitor, WISE, Affects Bone Density (manuscript).
Gong, Y., et al., LDL Receptor-Related Protein 5 (LRP5) Affects Bone Accrual and Eye Development. Cell 107: 513-523 (Nov. 16, 2001).
Hamersma, H., el at, The natural history of sclerosteosis, Clinical Genetics 63:192-197 (2003).
Harada, S., et al, Control of osteoblast function and regulation of bone mass, Nature 423:349-355 (2003).
Harris, S., et al. Human Fetal Osteoblast Progenitor Cell Lines (hFOB), http.//www.mayo.edutechcomm/93010.html, visited Jun. 11, 2003.
Hartley, K.O., et al., Targeted gene expression in trasngenic *Xenopus* using the binary Ga14-UAS system, Proc. Natl. Acad. Sci. 99(3): 1377-1382.
Hartmann. C., Wnt-signaling and skeletogenesis, J. Musculoskel Neuron Interact 2(3):274-276 (2002).
Hemmati-Brivanlou, A., Vertebrate Neural Induction, Annual Review Neuroscience 20:43-60 (1997).
Hoppler, S., Wnt Signalling In *Xenopus* Development, http://www.personal.dundee.ac.uk/-sphopple/research.html, visited on May 1, 2002.

(Continued)

*Primary Examiner*—Ilia Ouspenski
(74) *Attorney, Agent, or Firm*—Bryan Cave LLP

(57) ABSTRACT

The present invention relates to methods and compositions for the prevention and treatment of renal damage. The invention provides protein-based renal therapeutic agents for administration to subjects in order to prevent or treat renal degeneration or damage.

6 Claims, 1 Drawing Sheet

OTHER PUBLICATIONS

Itasaki, N.. et al., Wise, a context-dependent activator and inhibitor of Wnt signalling, Development 130:4295-4305 (2003).

Ivkovic, S., et al., Connective tissue growth factor coordinates chondrogenesis and angiogenesis during skeletal development, Development 130:2779-2791 (2003).

Karsenty G., The complexities of skeletal biology, Nature 423:316-318 (2003).

Kato. M., et al., Cbfal-Independent decrease in osteoblast proliferation, osteopenia, and persistent embryonic eye vascularization In mice deficient inLrp5, a Wnt coreceptor, The Journal of Cell Biology, 157 (2): 303-314 (Apr. 15, 2002).

Kerszberg, M., et al., A simple molecular model of neurulation, BioEssays 20:758-770 (1998), John Wiley & Sons, Inc.

Kronenberg. H.M., et al., Developmental regulation of the growth plate, Nature 423: 332-338 (2003).

Kusu, N., et al., Sclerostin is a Novel Secreted Osteoclast-Derived Bone Morphogenetic Protein (BMP) Antagonist with Unique Ligand Specificity, The American Society for Biochemistry and Molecular Biology, Inc., published on Apr. 17, 2003 as Manuscript M301716200.

Latinkic, B. V., et. al., *Xenopus* Cyr61 regulates gastrulation movements and modulates Wnt signalling. Development 130:2429-2441 (2003).

Little, R.D., et. al., A Mutation in the LDL Receptor-Related Protein 5 Gene Results in the Autosomal Dominant High-Bone-Mass Trait, The American Journal of Human Genetics 70:11-19 (2002).

Little, R.D., et. al., High Bone Density Due to a Mutation in LDL-Receptor-Related Protein 5, The New England Journal of Medicine, vol. 347(12), pp. 943-944 (Sep. 19, 2002).

Mao. B., et. al., LDL-receptor-related protein 6 is a receptor for Dickkopf proteins. Nature 411:321-325 (May 17, 2001).

Mathis, J.R., et. al., Pre-Steady-State Study of Recombinant Sesquiterpene Cyclases, Biochemistry 38:8340-8348 (1997).

McClary, K., et al., The Effects of Ascorbic Acid on the Osteoblast Extracellualr Matrix, http://lsvl.Ia.asu.edu/ubep2001/abstracts/mcclaryl, visted on Jun. 11, 2003.

McMahon, J.A., et al., Noggin-mediated antagonism of BMP signaling is required for growth and patterning of the neural tube and somite, Genes & Development 12:1438-1452.

Meitinger, T., et al., Molecular modelling of the Norrie disease protein predicts a cystine knot growth factor tertiary structure, Nature Genetics, vol. 5 (Dec. 1993).

Mercurio, S., et al., Connective-Tissue growth factor (CTGF) modulates Wnt signalling and interacts with the Wnt receptor complex (manuscript).

Moon, R.T., et al., Overview of the role of beta-catenin in specification of the dorsal-ventral axis of Xenopus, http://www.ucalgary.ca/UofC/eduweb/virtuatembryo/beta catenin.html.

Nijweide, P.J., et al., Idenfication of osteocytes in osteoblast-like cell cultures using a monoclonal antibody specifically directed against osteocytes, Histochemistry 84:342-347 (1986).

Patel, Z., et al., The Role of Retinoic Acid in Patterning of the CNS in *Xenopus*, http://www.ucalgary.ca/UofC/eduwebg/virtualembryo/retinoicCNS.html.

Prince, V.E., et al., Hox gene expression reveals regionalization along the anteroposterior axis of the zebrafish notochord. Dev Genes Evol 208:517-522 (1998).

Rosen, C.J., et al., Defining the Genetics of Osteoporosis: Using the Mouse to Understand Man, Osteoporosis International 12:803-810 (2001).

Segarini, P.R.. et al., The Low Density Lipoprotein Receptor-Related Protein/alpha2-Macroglobulin Receptor is a Receptor for Connective Tissue Growth Factor (CTGF), The American Society for Biochemistry and Molecular Biology, Inc., Published on Aug. 22, 2001 as Manuscript M105180200.

Simmons, D.G., et al., Uterine Sensitization-Associated Gene-1: A Novel Gene Induced Within the Rat Endometrium at the Time of Uterine Receptivity/Sensitization for the Decidual Cell Reaction, Biology of Reproduction 67:1638-1645 (2002).

Stephen. L.X.G., et al., Dental and oral manifestations of Sclerosteosis, International Dental Journal 51:287-290 (2001).

Streit, A., et al., Neural induction a bird's eye view, Trends In Genetics 15(1): 20-24 (1999).

Tamai, K, et al., LDL-receptor-related proteins in Wnt signal transduction. Nature 407:530-535 (2000).

Thisse, B., et al., Activin-and Nodel-related factors control anteroposterior patterning of the zebrafish embryo, Nature, vol. 403 (Jan. 27, 2000).

Torres, R.M., et al., The Cologne Guide to Gene Targeting (manuscript) (1995).

Wu, W., et al., Mutual antagonism between dickkopf1 and dickkopf2 regulates Wnt/beta-catenin signaling, Current Biology14-28; 10 (24) 1611-14 (2000).

Zelzer, E., et at, The genetic basis for skeletal diseases, Nature 423:343-348 (2003).

Amaya, E., et al., Expression of a Dominant Negative Mutant of the FGF Receptor Disrupts Mesoderm Formation in *Xenopus* Embryos, Cell 66:257-270 (Jul. 26, 1991).

Axelrod, J.D., et al., Differential recruitment of Dishevelled provides signaling specificity in the planar cell polarity and Wingless signaling pathways, Genes & Development 12:2610-2622 (1998).

Baker, J.C., et al., Wnt signaling in *Xenopus* embryos Inhibits Bmp4 expression and activates neural development, Genes & Development 13:3149-3159 (1999).

Beddington, R., et al., Anterior patterning in mouse, Trends in Genetics 14:277-284 (Jul. 1998).

Beddington, R., et al., Axis Development and Early Asymmetry In Mammals, Cell 98:195-209 (Jan. 22, 1999).

Blumberg, B., et al., An essential role for retinoid signaling in anteroposterior neural patterning, Development 124:373-379 (1997).

Bourguignon, C., et al., XBF-1, a winged helix transcription factor with dual activity, has a role in positioning neurogenesis in *Xenopus* competent ectoderm, Development 125:4889-4900 (1998).

Bradley, L., et al., Different Activities of the Frizzled-Rotated Proteins frzb2 and sizzled2 during *Xenopus* Anteroposterior Patterning, Developmental Biology 227:118-132 (2000).

Brannon, M., et al., A β-catentn/XTcf-3 complex binds to the slamois promoter to regulate dorsal axis specification in *Xenopus*, Genes & Development 11:2359-2370 (1997).

Cadigan, K.M., et al., Wnt signaling: a common theme in animal development, Genes & Development 11:3286-3305 (1997).

Capdevila, J., et al., Control of Dorsoventral Somite Patterning by Wnt-1 and β-Catenin, Developmental Biology 193:182-194 (1998).

Christian, J.L., et al., Interactions between Xwnt-8 and Spemann organizer signaling pathways generate dorsoventral pattern in the embryonic mesoderm of *Xenopus*. Genes & Development 7:13-28 (1993).

Condie, B.G., et al., Most of the Homeobox-Containing Xhox 36 Transcripts in Early Xenopus Embryos Cannot Encode a Homeodomain Protein, Molecular and Cellular Biology 10:3376-3385 (Jul. 1990).

Cox, W.G., et al., Caudalization of neural fate by tissue recombination and bFGF, Development 121:4349.4358 (1995).

Danielian, P.S., et al., Engrailed-1 as a target of the Wnt-1 signalling pathway in vertebrate midbrain development, Nature 383:332-334 (Sep. 26, 1996).

Dickinson, ME., et al., Dorsalization of the neural tube by the nonneural ectoderm, Development 121: 2099-2106 (1995).

Doniach, T., Planar and Vertical induction of anteroposterior Pattern during the Development of theamphibian Central Nervous System, Journal of Neurobiology 24 (10):1256-1275 (1993).

Ensini, M., et al., The control of rostrocaudal pattern in the developing spinal cord: specification of motor neuron subtype identity is initiated by signals from paraxial mesoderm, Development 125:969-982 (1998).

Fagotto, F., et al., Induction of the primary dorsalizing center in Xenopus by the Wnt/GSK/β-catenin signaling pathway, but not by Vg1, Activin or Noggin, Development 124:453-460 (1997).

Fan, M.J., et al., A role for Siamois in Spemann organizer formation, Development 124:2581-2589 (1997).

Fredieu, J.R., et al., Xwnt-8 and Lithium Can Act upon either dorsal Mesodermal or Neurectodermal Cells to Cause a Loss of Forebrain in Xenopus Embryos, Developmental Biology 188: 100-114 (1997).

Gavalas, A., et al., Retinoid signaling and hindbrain patterning, Cur Opin Genet Dev 10:380-386 (2000).

Glinka, A., et al., Dickkopf-1 is a member of a new family of secreted proteins and functions in head induction, Nature 391:357-382 (Jan. 22, 1998).

Glinka, A., et al., Head induction by simultaneous repression of Bmp and Wnt signaling In Xenopus, Nature 389:517-519 (Oct. 2, 1997).

Gould, A., et al., Initiation of Rhombomeric Hoxb4 Expression Requires Induction by Somites and a Retinoid Pathway, Neuron 21:39-51 (Jul. 1998).

Grapin-Botton, A., et al., Hox gene Induction in the neural tube depends on three parameters: competence, signal supply and paralogue group, Development 124:849-859 (1997).

Hamburger, V., et al., A series of normal stages in the development of the chick embryo, J. Morph. 88:49-92 (1951).

He, X., et al., A Member of the Frizzled Protein Family Mediating Axis Induction by Wnt-5A, Science 275:1652-1654 (Mar. 14, 1997).

Heasman, J., et al', β-Catenin Signaling Activity Dissected in the Early Xenopus Embryo: A Novel Antisense Approach, Developmental Biology 222:124-134 (2000).

Heisenberg, C.P., et al., Silberblick/Wnt11 mediates convergent extension movements during zebrafish gastrulation, Nature 405:76-81 (May 4, 2000).

Hemmati-Brivanlou, A., et al., Follistatin, an Antagonist of Activin, Is Expressed in the Spemann Organizer and Displays Direct Neuralizing Activity, Cell 77:283-295 (Apr. 22, 1994).

Hemmati-Brivanlou, A., et al., Vertebrate Embryonic Cells Will Become Nerve Cells Unless Told Otherwise, Cell 88:13-17 (Jan. 10, 1997).

Hemmati-Brivanlou, A., et al., Inhibition of Activin Receptor Signaling Promotes Neuralization in Xenopus, Cell 77:273-281 (Apr. 22, 1994).

Hoppler, S., et al., Expression of a dominant-negative Wnt blocks induction of MyoD in Xenopus embryos, Genes & Development 10:2805-2817 (1996).

Hsieh, J. C., et al., A new secreted protein that binds to Wnt proteins and inhibits their activites, Nature 398:431-436 (Apr. 1, 1999).

Itasaki, N., et al., Reprogramming Hox Expression in the Vertebrate Hindbrain: Influence of Paraxial Mesoderm and Rhombomere Transposition, Neuron 18:487-500 (Mar. 1996).

Itoh, K., et al., Graded amounts of Xenopus disheveled specify discrete anteroposterior cell fates in prospective ectoderm, Mechanisms of Development 61:113-125 (1997).

Itoh, K., et al., Axis determination by inhibition of Wnt signaling in Xenopus, Genes & Development 13:2328-2338 (1999).

Itoh. K., et al., Specific modulation of ectodermal cell fates in Xenopus embryos by glycogen syntase kinase, Development 121:3979-3988 (1995).

Jones, CM., et al., An Overview of Xenopus Development, Methods in Molecular Biology 97:331-340 (1999).

Jones, C.M., et al., Wholemount In Situ Hybridization to Xenopus Embryos, Methods in Molecular Biology 97:635-640 (1999).

Joyner, XL, Engrailed, Wnt and Pax genes regulate midbrain-hindbrain development, Trends in Genetics 12(1)15 15-20 (1996).

Kintner, C., Molecular bases of early neural development In Xenopus embryos, Ann. Rev. Neurosci 15:251-284 (1992).

Kolm, P.J., et al., Xenopus Hindbrain Patterning Requires Retinoid Signaling, Developmental Biology 192, 1-16 (1997).

Krieg, Pa., et al., In Vitro RNA Synthesis with SP6 RNA Polymerase, Methods in Enzymology 155:397-415 (1988).

Lamb, T.M., et al., Fibroblast growth factor is a direct neural inducer, which combined with noggin generates anterior-posterior neural pattern, Development 121:3827-3636 (1995).

Lee, K.J., et al., The specification of dorsal cell fates in the vertebrate central nervous system, Annual Review of Neuroscience 22(1) 261-294 (1999).

Leyns, L., et al., Frzb-1 is a Secreted Antagonist of Wnt Signaling Expresses in the Spemann Organizer, Cell 88:747-756 (Mar. 21, 1997).

Liem, K.F., et al., A Role for the Roof Plate and Its Resident TGFβ-Related Proteins in Neuronal Patterning in the Dorsal Spinal Cord. Cell 91:127-138 (Oct. 3, 1997).

Liem, K.F., et al., Dorsal Differentiation of Neural Plate Cells Induced by BMP-Mediated Signals from Epidermal Ectoderm, Cell 82:969-979 (Sep. 22, 1995).

Lin, X., et al., Daily cooperates with Drosophila Frizzled 2 to transduce Wingless signaling, Nature 400:281-284 (Jul. 15, 1999).

Lu, J., et al., Isolation and characterization of checker β-catenin, Gene 196:201-207 (1997).

Lumsden, A., et al., Patterning the Vertebrate Neuraxis, Science 274:1109-1115 (1996).

McGrew, L.L., et al., Wnt and FGF pathways cooperatively pattern anteroposterior neural ectoderm in Xenopus, Mechanisms of Development 69:105-114 (1997).

McGrew, L.L., et al., Specification of the Anteroposterior Neural Axis through Synergistic Interaction of the Wnt Signaling Cascade with noggin and follistatin, Developmental Biology 172:337-342 (1995).

McGrew, L.L.,. et al., Direct regulation of the Xenopus engrailed-2 promoter by the Wnt signaling pathway, and a molecular screen for Wnt-responsive genes, confirm a role for Wnt signaling during neural patterning in Xenopus, Mechanisms of Development 87:21-32 (1999).

McMahon, A.P., et al., The Midbrain-Hindbrain Phenotype of Wnt-1-/Wnt-1- Mice Results from Stepwise Deletion of engrailed-Expressing Cells by 9.5 Days Postcoitum, Cell 69:581-595 (1992).

Moon, R.T., et al., Structurally Related Receptors and Antagonists Compete for Secreted Wnt Ligands, Cell 88:725-728 (Mar. 21, 1997).

Muhr, J., et al., Convergent Inductive Signals Specify Midbrain, Hindbrain, and Spinal Cord Identify in Gastrula Stage Chick Embryos, Neuron 23:689-702 (Aug. 1999).

Muhr, J., et al., Assignment of Early Caudal Identity to Neural Plate Cells by a Signal from Caudal Paraxial Mesoderm, Neuron 19:487-502 (Sep. 1997).

Munsterberg, A.E., et al., Combinatorial signaling by Sonic hedgehog and Wnt family members induces myogenlc gHLH gene expression in the somite, Genes & Development 9:2911-2922 (1995).

Nieuwkoop, P.D., et al., Activation and organization of the central nervous system in amphibians, The Journal of Experimental Zoology 120(1):1-108 (Jun. 1952).

Pera, E.M., et al., A direct screen for secreted proteins in Xenopus embryos indentifies distinct activities for the Wnt antagonists Crescent and Frzb-1, Mechanisms of Development 98:183-195 (2000).

Piccolo. S., et al., The head Inducer Cerberus is a multifunctional antagonist of Nodal, BMP and Wnt signals, Nature 397:707-710 (Feb. 25, 1999).

Piccolo, S., et al., Dorsoventral Patterning in Xenopus: Inhibition of Ventral Signals by Direct Binding of Chordin to BMP-4, Cell 86:589-598 (Aug. 23, 1996).

Pinson, K.I., et al., An LDL-receptor-related protein mediates Wnt signaling in mice, Nature 407:535-538 (Sep. 28, 2000).

Pownall, M.E., et al., eFGF, Xcad3 and Hox genes form a molecular pathway that establishes the anteroposterlor axis In Xenopus, Development 122:3881-3892 (1998).

Pownall, M.E., et al., Two phases of Hox gene regulation during early Xenopus development, Current Biology 8(11):673-676.

Rasmussen, J.T., et al., Regulation of eye development by frizzled signaling in Xenopus, Proc Natl Acad Sci USA 98(7):3881-3866 (Mar. 27, 2001).

Rothberg, J.M., et al., slit: an extracellular protein necessary for development of midline glia and commissural axon pathways contains both EGF and LRR domains, Genes & Development 4:2169-2187 (1990).

Ruiz i Altaba, A., Pattern formation in the vertebrate neural plate, TINS 17 (6):233-243 (1994).

Salic, A.N., et al., Sizzled: a secreted Xwnt8 antagonist expressed in the ventral marginal zone of Xenopus embryos. Development 124:4739-4748 (1997).

Tada, M., et al., Xwntll is a target of *Xenopus brachyury*: regulation of gastrulation movements via Disheveled, but not through the canonical Wnt pathway, Development 127:2227-2238 (2000).

Tamai, K., et al., LDL-receptor-related proteins in Wnt signal transduction, Nature 407:530-535 (Sep. 28, 2000).

Trainor, P., et al., Plasticity in mouse neural crest cells reveals a new patterning role for cranial mesoderm, Nature Cell Biology 2:96-102 (Feb. 2000).

Tsuda, M., et al., The cell-surface proteoglycan Daily regulates Wingless signaling in Drosophila, Nature 400:276-280 (Jul. 15, 1999).

Vleminckx, K., et al., The C-terminal transactivation domian of β-catenin is necessary and sufficient for signaling by the LEF-1/β-catenin complex in *Xenopus laevis*, Mechanisms of development 81:65-74 (1999).

von Heune, G., A new method for predicting signal sequence cleavage sites, Nucleic Acid Research 14:4683-4690 (1986).

Wallingford, J.B., et al., Dishevelled controls cell polarity during Xenopus gastrulation, Nature 405:81-85 (May 4, 2000).

Wang, S., et al., Frzb, a Secreted Protein Expressed in the Spemann Organizer, Binds and inhibits Wnt-8, Cell 88:757-766 (Mar. 21, 1997).

Wehrli, M., et al., arrow encodes an LDL-receptor-related protein essential for Wingless signaling, Nature 407:527-530 (Sep. 28, 2000).

Yang, X., et al., CBFA1, OSF-1 Expression and Ex Vivo Mineralisation by Human Osteoprogenitors on 3-Dimensional Porous biodegradable Structures, Poster Session, 47$^{th}$ Annual Meeting, Orthopaedic Research Society, Feb. 25-28, 2001, San Francisco, CA.

Abreu, J.G., et al., Connective tissue growth factor modulates cell signaling by BMP and TGF-β (manuscript).

Beighton, P., Sclerosteosis, Journal of Medical Genetics 25:200-203 (1988).

Kadkhodayan, S., et al., Cloning, Expression, and One-Step Purification of the Minimal Essential Domain of the Light Chain of Botulinum Neurotoxin Type A. Protein Expression and Purification 19:125-130 (2000).

Laurikkala, J., et al., Identification of a secreted BMP antagonist, ectodin, integrating BMP, FGF, and SHH signals from the tooth enamel knot Development Biology 264(1):91-105 (2003).

Marchler-Bauer, A., et al., COD: a curated Entrez database of conserved domain alignments, Nucleic Acids Research 31(1):383-387 (2003).

Stebbins, C.E., et al., Structure of the VHL-ElonginC-ElonginB Comples: Implications for VHL Tumor Suppressor Function, Science Magazine, 284:455-461 (Apr. 16, 1999).

Wood, R.E., et al., Jaw involvement in slcerosteosis: a case report, Dentomaxillofac. Radiol. 17:145-148 (1988).

Balemans, W., et al., Lack of Association Between the SOST Gene and Bone Mineral Density in Perimenopausal Women: Analysis of Five Polymorphisms, Bone, 31(4):515-519 (Oct. 2002).

Ebisawa, T., et al., Characterization of bone morphogenetic protein-6 signaling pathways in osteoblast differentiation, Journal of Cell Science 112:3519-3527 (1999).

Groppe, J., et al., Structural basis of BMP signaling inhibition by the cystine knot protein Noggin, Nature 420:636-642 (Dec. 12, 2002).

Jena, N. et al., BMP7 Null Mutation in Mice: Developmental Defects in Skeleton, Kidney, and Eye, Experimental Cell Research 230:28-37 (1997).

Karsenty, G., et al., Reaching a Genetic and Molecular Undrstanding of Skeletal Development 2:389-406 (Apr. 2002).

Katagiri, T., et al., Skeletal Abnormalities in Doubly Heterozygous Bmp4 and Bmp7 Mice, Developmental Genetics 22:340-348 (1998).

Patel, KS., et al., Regulation of Bone Formation and Vision by LRP5, The New England Journal of Medicine 346(20):1572-1574 (May 16, 2002).

Reddi, A.H., Interplay between bone morphogenetic proteins and cognate binding proteins in bone and cartilage development: noggin, choridin and DAN, commentary available online http://arthritis-research.com/content/3/1/001.

Schweizer, L., et al., Wnt/Wingless signaling through β-catenin requires the function of both LRP/Arrow and frizzied, classes of receptors, BMC Cell Biology research article available at http://www.biomedcentral.com/1471-2121/4/4.

Solloway, M.J., et al., Mice Lacking Bmp8 Function, Developmental Genetics 22321-339 (1998).

Winkler, D.G., et al., Osteocyte control of bone formation via sclerostin, a novel BMP antagonist, The European Molecular Biology Organization Journal 22(23):6287-6276 (2003).

Kusu, N. et al. Sclerostin is a novel secreted osteoclast-derived bone morphogenetic protein antagonist with unique ligand specificity. J Biol Chem 278, 24113-7 (2003).

Sasai, Y. et al. Xenopus chordin: a novel dorsalizing factor activated by organizer-specific homeobox genes. Cell 79, 779-90 (1994).

Hsu, D. R., Economides, A. N., Wang, X., Eimon, P. M. & Harland, R. M. The Xenopus dorsalizing factor Gremlin identifies a novel family of secreted proteins that antagonize BMP activities. Mol Cell 1, 673-83, (1998).

Stanley, E. et al. DAN is a secreted glycoprotein related to *Xenopus cerberus*. Mech Dev 77, 173-84 (1998).

Yokouchi, Y., Vogan, K. J., Pearse, R. V., 2nd & Tabin, C. J. Antagonistic signaling by Caronte, a novel Cerberus-related gene, establishes left-right asymmetric gene expression. Cell 98, 573-83 (1999).

Abreu, J. G., Ketpura, N. I., Reversade, B. & De Robertis, E. M. Connective-tissue growth factor (CTGF) modulates cell signalling by BMP and TGF-beta. Nat Cell Biol. 4, 599-604 (2002).

Fullwood, P. et al. X linked exudative vitreoretinopathy: clinical features and genetic linkage analysis. Br J Ophthalmol. 77, 168-70 (1993).

Aberg, T. et al. Phenotypic changes in dentition of Runx2 homozygote-null mutant mice. J Histochem Cytochem 52, 131-9 (2004).

Karsenty, G. Minireview: transcriptional control of osteoblast differentiation. Endocrinology 142, 2731-3 (2001).

Sevetson, B., Taylor, S. & Pan, Y. Cbfal/RUNX2 directs specific expression of the sclerosteosis gene (SOST). J Biol Chem (2004).

Gall, C., Lauterborn, J. & Guthrie, K. in Autoradiography and Correlative Imaging (ed. W. E. Stumpf and H. F. Solomon) 379-399 (Academic Press, San Diego, 1995).

Kronenberg, H. M. Twist genes regulate runx2 and bone formation. Dev Cell 6,3 17-8 (2004).

Benzing et al., "Wnt Signaling in Polycystic Kidney Disease", J. American Society of Nephrology, 18: 1389-1398 (2007).

Ellies et al., "Bone Density Ligand, Sclerostin, Directly Interacts With LRP5 but Not LRP5G171V To Modulate Wnt Activity", J. Bone and Mineral Research, 21: 1738-1749 (2006).

Kuure, "Kidney Induction: Control by Notch, Wnt and GDNF/Ret Signaling", Helsinki University Biomedical Dissertations No. 90 (2007).

Semenov et al., "SOST Is a Ligand for LRP5/LRP6 and a Wnt Signaling Inhibitor", J. Biol. Chem. 280 (29): 26770-5 (2005).

Tanaka et al., "Expression of BMP-7 and USAG-1 (a BMP antagonist) in kidney development and injury", Kidney International, 73:181-191 (2008).

Yanagita et al., "Uterine sensitization-associated gene-1 (USAG-1), a novel BMP antagonist expressed in the kidney, accelerates tubular injury", J. Clinical Investigation, 116:70-79 (2006).

* cited by examiner

FIG. 1

SEQUENCE LISTING

<160> NUMBER OF SEQ ID NOS: 217

<210> SEQ ID NO 1
<211> LENGTH: 4131
<212> TYPE: DNA
<213> ORGANISM: Human

<400> SEQUENCE: 1

| | | | | | |
|---|---|---|---|---|---:|
| atgggggccg | tcctgaggag | cctcctggcc | tgcagcttct | gtgtgctcct | gagagcggcc | 60 |
| cctttgttgc | tttatgcaaa | cagacgggac | ttgcgattgg | ttgatgctac | aaatggcaaa | 120 |
| gagaatgcta | cgattgtagt | tggaggcttg | aggatgcag | ctgcggtgga | ctttgtgttt | 180 |
| agtcatggct | tgatatactg | gagtgatgtc | agcgaagaag | ccattaaacg | aacagaattt | 240 |
| aacaaaactg | agagtgtgca | gaatgttgtt | gtttctggat | tattgtcccc | cgatgggctg | 300 |
| gcatgtgatt | ggcttggaga | aaaattgtac | tggacagatt | ctgaaactaa | tcggattgaa | 360 |
| gtttctaatt | tagatggatc | tttacgaaaa | gttttatttt | ggcaagagtt | ggatcaaccc | 420 |
| agagctattg | ccttagatcc | ttcaagtggg | ttcatgtact | ggacagactg | gggagaagtg | 480 |
| ccaaagatag | aacgtgctgg | aatggatggt | tcaagtcgct | tcattataat | aaacagtgaa | 540 |
| atttactggc | aaatggact | gactttggat | tatgaagaac | aaaagcttta | ttgggcagat | 600 |
| gcaaaactta | atttcatcca | caatcaaat | ctggatggaa | caaatcggca | ggcagtggtt | 660 |
| aaaggttccc | ttccacatcc | ttttgccttg | acgttatttg | aggacatatt | gtactggact | 720 |
| gactggagca | cacactccat | tttggcttgc | aacaagtata | ctggtgaggg | tctgcgtgaa | 780 |
| atccattctg | acatcttctc | tcccatggat | atacatgcct | tcagccaaca | gaggcagcca | 840 |
| aatgccacaa | atccatgtgg | aattgacaat | gggggttgtt | cccatttgtg | tttgatgtct | 900 |
| ccagtcaagc | ttttttatca | gtgtgcttgc | cccactgggg | tcaaactcct | ggagaatgga | 960 |
| aaaacctgca | agatggtgc | cacagaatta | ttgcttttag | ctcgaaggac | agacttgaga | 1020 |
| cgcatttctt | tggatacacc | agattttaca | gacattgttc | tgcagttaga | agacatccgt | 1080 |
| catgccattg | ccatagatta | cgatcctgtg | gaaggctaca | tctactggac | tgatgatgaa | 1140 |
| gtgagggcca | tacgccgttc | atttatagat | ggatctggca | gtcagtttgt | ggtcactgct | 1200 |
| caaattgccc | atcctgatgg | tattgctgtg | gactgggttg | cacgaaatct | ttattggaca | 1260 |
| gacactggca | ctgatcgaat | agaagtgaca | aggctcaatg | ggaccatgag | gaagatcttg | 1320 |
| atttcagagg | acttagagga | accccgggct | attgtgttag | atcccatggt | tgggtacatg | 1380 |
| tattggactg | actggggaga | aattccgaaa | attgagcgag | cagctctgga | tggttctgac | 1440 |
| cgtgtagtat | tggttaacac | ttctcttggt | tggccaaatg | gttagccttt | ggattatgat | 1500 |
| gaaggcaaaa | tatactgggg | agatgccaaa | acagacaaga | ttgaggttat | gaatactgat | 1560 |
| ggcactggga | gacgagtact | agtggaagac | aaaattcctc | acatatttgg | atttactttg | 1620 |
| ttgggtgact | atgtttactg | gactgactgg | cagaggcgta | gcattgaaag | agttcataaa | 1680 |
| cgaagtgcag | agagggaagt | gatcatagat | cagctgcctg | acctcatggg | cctaaaggct | 1740 |
| acaaatgttc | atcgagtgat | tggttccaac | ccctgtgctg | aggaaaacgg | gggatgtagc | 1800 |
| catctctgcc | tctatagacc | tcagggcctt | cgctgtgctt | gccctattgg | ctttgaactc | 1860 |
| atcagtgaca | tgaagacctg | cattgtccca | gaggctttcc | ttttgttttc | acggagagca | 1920 |
| gatatcagac | gaatttctct | ggaaacaaac | aataataatg | tggctattcc | actcactggt | 1980 |
| gtcaaagaag | cttctgcttt | ggattttgat | gtgacagaca | accgaattta | ttggactgat | 2040 |

```
atatcactca agaccatcag cagagccttt atgaatggca gtgcactgga acatgtggta    2100
gaattcggct tagattatcc agaaggcatg gcagtagact ggcttgggaa gaacttgtac    2160
tgggcagaca caggaacgaa tcgaattgag gtgtcaaagt tggatgggca gcaccgacaa    2220
gttttggtgt ggaaagacct agatagtccc agagctctcg cgttggaccc tgccgaagga    2280
tttatgtatt ggactgaatg gggtggaaaa cctaagatag acagagctgc aatggatgga    2340
agtgaacgta ctaccttagt tccaaatgtg gggcgggcaa acggcctaac tattgattat    2400
gctaaaagga ggctttattg gacagacctg gacaccaact aatagaatc ttcaaatatg    2460
cttgggctca accgtgaagt tatagcagat gacttgcctc atccttttgg cttaactcag    2520
taccaagatt atatctactg gacggactgg agccgacgca gcattgagcg tgccaacaaa    2580
accagtggcc aaaaccgcac catcattcag ggccatttgg attatgtgat ggacatcctc    2640
gtctttcact catctcgaca gtcagggtgg aatgaatgtg cttccagcaa tgggcactgc    2700
tcccacctct gcttggctgt gccagttggg ggttttgttt gtggatgccc tgcccactac    2760
tctcttaatg ctgacaacag gacttgtagt gctcctacga cttttcctgct cttcagtcaa    2820
aagagtgcca tcaaccgcat ggtgattgat gaacaacaga gccccgacat catccttccc    2880
atccacagcc ttcggaatgt ccgggccatt gactatgacc cactggacaa gcaactctat    2940
tggattgact cacgacaaaa catgatccga aaggcacaag aagatggcag ccagggcttt    3000
actgtggttg tgagctcagt tccgagtcag aacctggaaa tacaacccta tgacctcagc    3060
attgatattt cagccgcta catctactgg acttgtgagg ctaccaatgt cattaatgtg    3120
acaagattag atgggagatc agttggagtg gtgctgaaag gcgagcagga cagacctcga    3180
gccattgtgg taaacccaga gaagggtat atgtatttta ccaatcttca ggaaaggtct    3240
cctaaaattg aacgggctgc tttggatggg acagaacggg aggtcctctt tttcagtggc    3300
ttaagtaaac caattgcttt agcccttgat agcaggctgg gcaagctctt ttgggctgat    3360
tcagatctcc ggcgaattga aagcagtgat ctctcaggtg ctaaccggat agtattagaa    3420
gactccaata tcttgcagcc tgtgggactt actgtgtttg aaaactggct ctattggatt    3480
gataaacagc agcaaatgat tgaaaaaatt gacatgacag gtcgagaggg tagaaccaaa    3540
gtccaagctc gaattgccca gcttagtgac attcatgcag taaaggagct gaaccttcaa    3600
gaatacagac agcacccttg tgctcaggat aatggtggct gttcacatat ttgtcttgta    3660
aaggggatg gtactacaag gtgttcttgc cccatgcacc tggttctact tcaagatgag    3720
ctatcatgtg gagaacctcc aacatgttct cctcagcagt ttacttgttt cacgggggaa    3780
attgactgta tccctgtggc ttggcggtgc gatgggttta ctgaatgtga agaccacagt    3840
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgctttgttt aattgatcag ttccgctgtg ccaatggtca gtgcattgga    4020
aagcacaaga gtgtgatca taatgtggat tgcagtgaca agtcagatga actggattgt    4080
tatccgactg aagaaccagc accacaggcc accaatacag ttggttctgt t              4131

<210> SEQ ID NO 2
<211> LENGTH: 1377
<212> TYPE: PRT
<213> ORGANISM: Human

<400> SEQUENCE: 2
```

-continued

```
Met Gly Ala Val Leu Arg Ser Leu Leu Ala Cys Ser Phe Cys Val Leu
1               5                   10                  15

Leu Arg Ala Ala Pro Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
                100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
```

-continued

```
                420                 425                 430
Asn Gly Thr Met Arg Lys Ile Leu Ile Ser Glu Asp Leu Glu Pro
            435                 440                 445
Arg Ala Ile Val Leu Asp Pro Met Val Gly Tyr Met Tyr Trp Thr Asp
            450                 455                 460
Trp Gly Glu Ile Pro Lys Ile Glu Arg Ala Ala Leu Asp Gly Ser Asp
465                 470                 475                 480
Arg Val Val Leu Val Asn Thr Ser Leu Gly Trp Pro Asn Gly Leu Ala
                    485                 490                 495
Leu Asp Tyr Asp Glu Gly Lys Ile Tyr Trp Gly Asp Ala Lys Thr Asp
                500                 505                 510
Lys Ile Glu Val Met Asn Thr Asp Gly Thr Gly Arg Arg Val Leu Val
                515                 520                 525
Glu Asp Lys Ile Pro His Ile Phe Gly Phe Thr Leu Leu Gly Asp Tyr
            530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Asn Val His Arg Val Ile Gly Ser Asn Pro Cys
                580                 585                 590
Ala Glu Glu Asn Gly Gly Cys Ser His Leu Cys Leu Tyr Arg Pro Gln
            595                 600                 605
Gly Leu Arg Cys Ala Cys Pro Ile Gly Phe Glu Leu Ile Ser Asp Met
            610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Val Ala Ile
                    645                 650                 655
Pro Leu Thr Gly Val Lys Glu Ala Ser Ala Leu Asp Phe Asp Val Thr
                660                 665                 670
Asp Asn Arg Ile Tyr Trp Thr Asp Ile Ser Leu Lys Thr Ile Ser Arg
                675                 680                 685
Ala Phe Met Asn Gly Ser Ala Leu Glu His Val Val Glu Phe Gly Leu
            690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                    725                 730                 735
Gln His Arg Gln Val Leu Val Trp Lys Asp Leu Asp Ser Pro Arg Ala
                740                 745                 750
Leu Ala Leu Asp Pro Ala Glu Gly Phe Met Tyr Trp Thr Glu Trp Gly
            755                 760                 765
Gly Lys Pro Lys Ile Asp Arg Ala Ala Met Asp Gly Ser Glu Arg Thr
            770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                    805                 810                 815
Ser Ser Asn Met Leu Gly Leu Asn Arg Glu Val Ile Ala Asp Asp Leu
                820                 825                 830
Pro His Pro Phe Gly Leu Thr Gln Tyr Gln Asp Tyr Ile Tyr Trp Thr
            835                 840                 845
```

-continued

```
Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
930                 935                 940

Asn Arg Met Val Ile Asp Glu Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245
```

```
Cys Ser Pro Gln Gln Phe Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val
    1370                1375
```

<210> SEQ ID NO 3
<211> LENGTH: 4842
<212> TYPE: DNA
<213> ORGANISM: Human

<400> SEQUENCE: 3

| | | |
|---|---|---|
| atgggggccg tcctgaggag cctcctggcc tgcagcttct gtgtgctcct gagagcggcc | 60 |
| cctttgttgc tttatgcaaa cagacgggac ttgcgattgg ttgatgctac aaatggcaaa | 120 |
| gagaatgcta cgattgtagt tggaggcttg gaggatgcag ctgcggtgga ctttgtgttt | 180 |
| agtcatggct tgatatactg gagtgatgtc agcgaagaag ccattaaacg aacagaattt | 240 |
| aacaaaactg agagtgtgca gaatgttgtt gtttctggat tattgtcccc cgatgggctg | 300 |
| gcatgtgatt ggcttggaga aaaattgtac tggacagatt ctgaaactaa tcggattgaa | 360 |
| gtttctaatt tagatggatc tttacgaaaa gttttatttt ggcaagagtt ggatcaaccc | 420 |
| agagctattg ccttagatcc ttcaagtggg ttcatgtact ggacagactg gggagaagtg | 480 |
| ccaaagatag aacgtgctgg aatggatggt tcaagtcgct tcattataat aaacagtgaa | 540 |
| atttactggc caaatggact gactttggat tatgaagaac aaaagcttta ttgggcagat | 600 |
| gcaaaactta atttcatcca caatcaaat ctggatggaa caaatcggca ggcagtggtt | 660 |
| aaaggttccc ttccacatcc ttttgccttg acgttatttg aggacatatt gtactggact | 720 |
| gactggagca cacactccat tttggcttgc aacaagtata ctggtgaggg tctgcgtgaa | 780 |
| atccattctg acatcttctc tcccatggat atacatgcct cagccaaca gaggcagcca | 840 |
| aatgccacaa atccatgtgg aattgacaat ggggttgtt cccatttgtg tttgatgtct | 900 |
| ccagtcaagc ttttttatca gtgtgcttgc cccactgggg tcaaactcct ggagaatgga | 960 |
| aaaacctgca agatggtgc cacagaatta ttgcttttag ctcgaaggac agacttgaga | 1020 |
| cgcatttctt tggatacacc agattttaca gacattgttc tgcagttaga agacatccgt | 1080 |
| catgccattg ccatagatta cgatcctgtg gaaggctaca tctactggac tgatgatgaa | 1140 |
| gtgagggcca tacgccgttc atttatagat ggatctggca gtcagtttgt ggtcactgct | 1200 |
| caaattgccc atcctgatgg tattgctgtg gactgggttg cacgaaatct ttattggaca | 1260 |
| gacactggca ctgatcgaat agaagtgaca aggctcaatg gaccatgag gaagatcttg | 1320 |

```
atttcagagg acttagagga accccgggct attgtgttag atcccatggt tgggtacatg   1380
tattggactg actggggaga aattccgaaa attgagcgag cagctctgga tggttctgac   1440
cgtgtagtat tggttaacac ttctcttggt tggccaaatg gtttagcctt ggattatgat   1500
gaaggcaaaa tatactgggg agatgccaaa acagacaaga ttgaggttat gaatactgat   1560
ggcactggga gacgagtact agtggaagac aaaattcctc acatatttgg atttactttg   1620
ttgggtgact atgtttactg gactgactgg cagaggcgta gcattgaaag agttcataaa   1680
cgaagtgcag agagggaagt gatcatagat cagctgcctg acctcatggg cctaaaggct   1740
acaaatgttc atcgagtgat tggttccaac ccctgtgctg aggaaaacgg gggatgtagc   1800
catctctgcc tctatagacc tcagggcctt cgctgtgctt gcctattgg ctttgaactc    1860 atcagtgaca tgaagacctg cattgtccca gaggctttcc ttttgttttc acggagagca   1920
gatatcagac gaatttctct ggaaacaaac aataataatg tggctattcc actcactggt   1980
gtcaaagaag cttctgcttt ggattttgat gtgacagaca accgaattta ttggactgat   2040
atatcactca agaccatcag cagagccttt atgaatggca gtgcactgga acatgtggta   2100
gaattcggct tagattatcc agaaggcatg gcagtagact ggcttgggaa gaacttgtac   2160
tgggcagaca caggaacgaa tcgaattgag gtgtcaaagt tggatgggca gcaccgacaa   2220
gttttggtgt ggaaagacct agatagtccc agagctctcg cgttggaccc tgccgaagga   2280
tttatgtatt ggactgaatg gggtggaaaa cctaagatag acagagctgc aatggatgga   2340
agtgaacgta ctaccttagt tccaaatgtg gggcgggcaa acggcctaac tattgattat   2400
gctaaaagga ggctttattg gacagacctg gacaccaact aatagaaatc ttcaaatatg   2460
cttgggctca accgtgaagt tatagcagat gacttgcctc atccttttgg cttaactcag   2520
taccaagatt atatctactg gacggactgg agccgacgca gcattgagcg tgccaacaaa   2580
accagtggcc aaaaccgcac catcattcag ggccatttgg attatgtgat ggacatcctc   2640
gtctttcact catctcgaca gtcagggtgg aatgaatgtg cttccagcaa tgggcactgc   2700
tcccacctct gcttggctgt gccagttggg ggttttgttt gtggatgccc tgcccactac   2760
tctcttaatg ctgacaacag gacttgtagt gctcctacga cttttcctgct cttcagtcaa   2820 aagagtgcca tcaaccgcat ggtgattgat gaacaacaga gccccgacat catccttccc   2880
atccacagcc ttcggaatgt ccgggccatt gactatgacc cactggacaa gcaactctat   2940
tggattgact cacgacaaaa catgatccga aaggcacaag aagatggcag ccagggcttt   3000
actgtggttg tgagctcagt tccgagtcag aacctggaaa tacaacccta tgacctcagc   3060
attgatattt acagccgcta catctactgg acttgtgagg ctaccaatgt cattaatgtg   3120
acaagattag atgggagatc agttggagtg gtgctgaaag gcgagcagga cagacctcga   3180
gccattgtgg taaacccaga gaagggtat atgtatttta ccaatcttca ggaaaggtct    3240
cctaaaattg aacgggctgc tttggatggg acagaacggg aggtcctctt tttcagtggc   3300
ttaagtaaac caattgcttt agcccttgat agcaggctgg gcaagctctt tgggctgat    3360 tcagatctcc ggcgaattga aagcagtgat ctctcaggtg ctaaccggat agtattagaa   3420
gactccaata tcttgcagcc tgtgggactt actgtgtttg aaaactggct ctattggatt   3480
gataaacagc agcaaatgat tgaaaaaatt gacatgacag tcgagaggg tagaaccaaa   3540 gtccaagctc gaattgccca gcttagtgac attcatgcag taaaggagct gaaccttcaa   3600
gaatacagac agcacccttg tgctcaggat aatggtggct gttcacatat ttgtcttgta   3660
aagggggatg gtactacaag gtgttcttgc cccatgcacc tggttctact tcaagatgag   3720
```

-continued

```
ctatcatgtg gagaacctcc aacatgttct cctcagcagt ttacttgttt cacgggggaa    3780
attgactgta tccctgtggc ttggcggtgc gatgggttta ctgaatgtga agaccacagt    3840
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgctttgttt aattgatcag ttccgctgtg ccaatggtca gtgcattgga    4020
aagcacaaga gtgtgatca taatgtggat tgcagtgaca gtcagatga actggattgt    4080
tatccgactg aagaaccagc accacaggcc accaatacag ttggttctgt tattggcgta    4140
attgtcacca ttttgtgtc tggaactgta tactttatct gccagaggat gttgtgtcca    4200
cgtatgaagg gagatgggga aactatgact aatgactatg tagttcatgg accagcttct    4260
gtgcctcttg gttatgtgcc acacccaagt tctttgtcag gatctcttcc aggaatgtct    4320
cgaggtaaat caatgatcag ctccctcagt atcatggggg gaagcagtgg accccccctat    4380
gaccgagccc atgttacagg agcatcatca agtagttctt caagcaccaa aggcacttac    4440
ttccctgcaa ttttgaaccc tccaccatcc ccagccacag agcgatcaca ttacactatg    4500
gaatttggat attcttcaaa cagtccttcc actcataggt catacagcta caggccatat    4560
agctaccggc actttgcacc ccccaccaca ccctgcagca cagatgtttg tgacagtgac    4620
tatgctccta gtcggagaat gacctcagtg caacagcca agggctatac cagtgacttg    4680
aactatgatt cagaacctgt gccccccacct cccacacccc gaagccaata cttgtcagca    4740
gaggagaact atgaaagctg cccaccttct ccatacacag agaggagcta ttctcatcac    4800
ctctacccac cgccaccctc tccctgtaca gactcctcct ga                       4842
```

<210> SEQ ID NO 4
<211> LENGTH: 1613
<212> TYPE: PRT
<213> ORGANISM: Human

<400> SEQUENCE: 4

```
Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175
```

```
Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
            195                 200                 205

Ser Asn Leu Asp Gly Thr Asn Arg Gln Ala Val Val Lys Gly Ser Leu
            210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
            290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
            370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
            450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
            530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590
```

-continued

```
Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
        610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
        675                 680                 685

Ala Phe Met Asn Gly Ser Ala Leu Glu His Val Glu Phe Gly Leu
        690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
        740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
        770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
                820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
        850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
        900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
                980                 985                 990

Gln Glu Asp Gly Ser Gln Gly Phe  Thr Val Val Val Ser  Ser Val Pro
        995                 1000                1005

Ser Gln  Asn Leu Glu Ile Gln  Pro Tyr Asp Leu Ser  Ile Asp Ile
```

-continued

```
              1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410
```

```
Val Val His Gly Pro Ala Ser Val Pro Leu Gly Tyr Val Pro His
    1415                1420                1425
Pro Ser Ser Leu Ser Gly Ser Leu Pro Gly Met Ser Arg Gly Lys
    1430                1435                1440
Ser Met Ile Ser Ser Leu Ser Ile Met Gly Gly Ser Ser Gly Pro
    1445                1450                1455
Pro Tyr Asp Arg Ala His Val Thr Gly Ala Ser Ser Ser Ser Ser
    1460                1465                1470
Ser Ser Thr Lys Gly Thr Tyr Phe Pro Ala Ile Leu Asn Pro Pro
    1475                1480                1485
Pro Ser Pro Ala Thr Glu Arg Ser His Tyr Thr Met Glu Phe Gly
    1490                1495                1500
Tyr Ser Ser Asn Ser Pro Ser Thr His Arg Ser Tyr Ser Tyr Arg
    1505                1510                1515
Pro Tyr Ser Tyr Arg His Phe Ala Pro Pro Thr Thr Pro Cys Ser
    1520                1525                1530
Thr Asp Val Cys Asp Ser Asp Tyr Ala Pro Ser Arg Arg Met Thr
    1535                1540                1545
Ser Val Ala Thr Ala Lys Gly Tyr Thr Ser Asp Leu Asn Tyr Asp
    1550                1555                1560
Ser Glu Pro Val Pro Pro Pro Thr Pro Arg Ser Gln Tyr Leu
    1565                1570                1575
Ser Ala Glu Glu Asn Tyr Glu Ser Cys Pro Pro Ser Pro Tyr Thr
    1580                1585                1590
Glu Arg Ser Tyr Ser His His Leu Tyr Pro Pro Pro Ser Pro
    1595                1600                1605
Cys Thr Asp Ser Ser
    1610
```

```
<210> SEQ ID NO 5
<211> LENGTH: 4161
<212> TYPE: DNA
<213> ORGANISM: Human

<400> SEQUENCE: 5
atggaggcag cgccgcccgg gccgccgtgg ccgctgctgc tgctgctgct gctgctgctg      60
gcgctgtgcg gctgcccggc cccgccgcg gcctcgccgc tcctgctatt tgccaaccgc     120
cgggacgtac ggctggtgga cgccggcgga gtcaagctgg agtccaccat cgtggtcagc     180
ggcctggagg atgcggccgc agtggacttc cagtttttcca agggagccgt gtactggaca     240
gacgtgagcg aggaggccat caagcagacc tacctgaacc agacggggc cgccgtgcag     300
aacgtggtca tctccggcct ggtctctccc gacggcctcg cctgcgactg ggtgggcaag     360
aagctgtact ggacggactc agagaccaac cgcatcgagg tggccaacct caatggcaca     420
tcccggaagg tgctcttctg gcaggacctt gaccagccga gggccatcgc cttggacccc     480
gctcacgggt acatgtactg gacagactgg ggtgagacgc cccggattga gcgggcaggg     540
atggatggca gcacccggaa gatcattgtg gactcggaca tttactggcc caatggactg     600
accatcgacc tggaggagca gaagctctac tgggctgacg ccaagctcag cttcatccac     660
cgtgccaacc tggacggctc gttccggcag aaggtggtgg agggcagcct gacgcacccc     720
ttcgccctga cgctctccgg ggacactctg tactggacag actggcagac ccgctccatc     780
catgcctgca caagcgcac tgggggggaag aggaaggaga tcctgagtgc cctctactca     840
```

```
cccatggaca tccaggtgct gagccaggag cggcagcctt tcttccacac tcgctgtgag      900
gaggacaatg gcggctgctc ccacctgtgc ctgctgtccc caagcgagcc tttctacaca      960
tgcgcctgcc ccacgggtgt gcagctgcag gacaacggca ggacgtgtaa ggcaggagcc     1020
gaggaggtgc tgctgctggc ccggcggacg gacctacgga ggatctcgct ggacacgccg     1080
gactttaccg acatcgtgct gcaggtggac gacatccggc acgccattgc catcgactac     1140
gacccgctag agggctatgt ctactggaca gatgacgagg tgcgggccat ccgcagggcg     1200
tacctggacg ggtctggggc gcagacgctg gtcaacaccg agatcaacga ccccgatggc     1260
atcgcggtcg actgggtggc ccgaaacctc tactggaccg acacgggcac ggaccgcatc     1320
gaggtgacgc gcctcaacgg cacctcccgc aagatcctgg tgtcggagga cctggacgag     1380
ccccgagcca tcgcactgca ccccgtgatg ggcctcatgt actggacaga ctggggagag     1440
aaccctaaaa tcgagtgtgc caacttggat gggcaggagc ggcgtgtgct ggtcaatgcc     1500
tccctcgggt ggcccaacgg cctggccctg gacctgcagg aggggaagct ctactgggga     1560
gacgccaaga cagacaagat cgaggtgatc aatgttgatg ggacgaagag gcggaccctc     1620
ctggaggaca agctcccgca cattttcggg ttcacgctgc tgggggactt catctactgg     1680
actgactggc agcgccgcag catcgagcgg gtgcacaagg tcaaggccag ccgggacgtc     1740
atcattgacc agctgcccga cctgatgggg ctcaaagctg tgaatgtggc caaggtcgtc     1800
ggaaccaacc cgtgtgcgga caggaacggg gggtgcagcc acctgtgctt cttcacaccc     1860
cacgcaaccc ggtgtggctg ccccatcggc ctggagctgc tgagtgacat gaagacctgc     1920
atcgtgcctg aggccttctt ggtcttcacc agcagagccg ccatccacag gatctccctc     1980
gagaccaata caacgacgt ggccatcccg ctcacgggcg tcaaggaggc ctcagccctg     2040
gactttgatg tgtccaacaa ccacatctac tggacagacg tcagcctgaa gaccatcagc     2100
cgcgccttca tgaacgggag ctcggtggag cacgtggtgg agtttggcct tgactacccc     2160
gagggcatgg ccgttgactg gatgggcaag aacctctact gggccgacac tgggaccaac     2220
agaatcgaag tggcgcggct ggacgggcag ttccggcaag tcctcgtgtg gagggacttg     2280
gacaacccga ggtcgctggc cctggatccc accaagggct acatctactg gaccgagtgg     2340
ggcggcaagc cgaggatcgt gcgggccttc atggacggga ccaactgcat gacgctggtg     2400
gacaaggtgg gccgggccaa cgacctcacc attgactacg ctgaccagcg cctctactgg     2460
accgacctgg acaccaacat gatcgagtcg tccaacatgc tgggtcagga gcgggtcgtg     2520
attgccgacg atctcccgca cccgttcggt ctgacgcagt acagcgatta tatctactgg     2580
acagactgga tctgcacag cattgagcgg gccgacaaga ctagcggccg gaaccgcacc     2640
ctcatccagg gccacctgga cttcgtgatg gacatcctgg tgttccactc ctcccgccag     2700
gatggcctca atgactgtat gcacaacaac gggcagtgtg ggcagctgtg ccttgccatc     2760
cccggcggcc accgctgcgg ctgcgcctca cactacaccc tggaccccag cagccgcaac     2820
tgcagcccgc ccaccacctt cttgctgttc agccagaaat ctgccatcag tcggatgatc     2880
ccggacgacc agcacagccc ggatctcatc ctgcccctgc atggactgag gaacgtcaaa     2940
gccatcgact atgacccact ggacaagttc atctactggg tggatgggcg ccagaacatc     3000
aagcgagcca aggacgacgg gacccagccc tttgttttga cctctctgag ccaaggccaa     3060
aacccagaca ggcagcccca cgacctcagc atcgacatct acagccggac actgttctgg     3120
acgtgcgagg ccaccaatac catcaacgtc cacaggctga gcggggaagc catgggggtg     3180
gtgctgcgtg gggaccgcga caagcccagg gccatcgtcg tcaacgcgga gcgagggtac     3240
```

```
ctgtacttca ccaacatgca ggaccgggca gccaagatcg aacgcgcagc cctggacggc    3300
accgagcgcg aggtcctctt caccaccggc ctcatccgcc ctgtggccct ggtggtagac    3360
aacacactgg gcaagctgtt ctgggtggac gcggacctga gcgcattga gagctgtgac    3420 ctgtcagggg ccaaccgcct gaccctggag gacgccaaca tcgtgcagcc tctgggcctg    3480
accatccttg gcaagcatct ctactggatc gaccgccagc agcagatgat cgagcgtgtg    3540
gagaagacca ccggggacaa gcggactcgc atccagggcc gtgtcgccca cctcactggc    3600
atccatgcag tggaggaagt cagcctggag gagttctcag cccacccatg tgcccgtgac    3660
aatggtggct gctcccacat ctgtattgcc aagggtgatg ggacaccacg gtgctcatgc    3720
ccagtccacc tcgtgctcct gcagaacctg ctgacctgtg agagccgcc cacctgctcc    3780 ccggaccagt ttgcatgtgc cacaggggag atcgactgta tccccggggc ctggcgctgt    3840
gacggctttc ccgagtgcga tgaccagagc gacgaggagg ctgccccgt gtgctccgcc    3900 gcccagttcc cctgcgcgcg gggtcagtgt gtggacctgc gcctgcgctg cgacggcgag    3960
gcagactgtc aggaccgctc agacgaggcg gactgtgacg ccatctgcct gcccaaccag    4020
ttccggtgtg cgagcggcca gtgtgtcctc atcaaacagc agtgcgactc cttccccgac    4080
tgtatcgacg gctccgacga gctcatgtgt gaaatcacca gccgccctc agacgacagc    4140 ccggcccaca gcagtgccat c                                              4161
```

<210> SEQ ID NO 6
<211> LENGTH: 1383
<212> TYPE: PRT
<213> ORGANISM: Human

<400> SEQUENCE: 6

```
Met Glu Ala Ala Pro Gly Pro Pro Trp Pro Leu Leu Leu Leu
1               5                   10                  15

Leu Leu Leu Ala Leu Cys Gly Cys Pro Ala Pro Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205
```

-continued

```
Leu Tyr Trp Ala Asp Ala Lys Leu Ser Phe Ile His Arg Ala Asn Leu
    210                 215                 220
Asp Gly Ser Phe Arg Gln Lys Val Val Glu Gly Ser Leu Thr His Pro
225                 230                 235                 240
Phe Ala Leu Thr Leu Ser Gly Asp Thr Leu Tyr Trp Thr Asp Trp Gln
                245                 250                 255
Thr Arg Ser Ile His Ala Cys Asn Lys Arg Thr Gly Gly Lys Arg Lys
            260                 265                 270
Glu Ile Leu Ser Ala Leu Tyr Ser Pro Met Asp Ile Gln Val Leu Ser
        275                 280                 285
Gln Glu Arg Gln Pro Phe Phe His Thr Arg Cys Glu Glu Asp Asn Gly
    290                 295                 300
Gly Cys Ser His Leu Cys Leu Leu Ser Pro Ser Glu Pro Phe Tyr Thr
305                 310                 315                 320
Cys Ala Cys Pro Thr Gly Val Gln Leu Gln Asp Asn Gly Arg Thr Cys
                325                 330                 335
Lys Ala Gly Ala Glu Glu Val Leu Leu Leu Ala Arg Arg Thr Asp Leu
            340                 345                 350
Arg Arg Ile Ser Leu Asp Thr Pro Asp Phe Thr Asp Ile Val Leu Gln
        355                 360                 365
Val Asp Asp Ile Arg His Ala Ile Ala Ile Asp Tyr Asp Pro Leu Glu
    370                 375                 380
Gly Tyr Val Tyr Trp Thr Asp Asp Glu Val Arg Ala Ile Arg Arg Ala
385                 390                 395                 400
Tyr Leu Asp Gly Ser Gly Ala Gln Thr Leu Val Asn Thr Glu Ile Asn
                405                 410                 415
Asp Pro Asp Gly Ile Ala Val Asp Trp Val Ala Arg Asn Leu Tyr Trp
            420                 425                 430
Thr Asp Thr Gly Thr Asp Arg Ile Glu Val Thr Arg Leu Asn Gly Thr
        435                 440                 445
Ser Arg Lys Ile Leu Val Ser Glu Asp Leu Asp Glu Pro Arg Ala Ile
    450                 455                 460
Ala Leu His Pro Val Met Gly Leu Met Tyr Trp Thr Asp Trp Gly Glu
465                 470                 475                 480
Asn Pro Lys Ile Glu Cys Ala Asn Leu Asp Gly Gln Glu Arg Arg Val
                485                 490                 495
Leu Val Asn Ala Ser Leu Gly Trp Pro Asn Gly Leu Ala Leu Asp Leu
            500                 505                 510
Gln Glu Gly Lys Leu Tyr Trp Gly Asp Ala Lys Thr Asp Lys Ile Glu
        515                 520                 525
Val Ile Asn Val Asp Gly Thr Lys Arg Arg Thr Leu Leu Glu Asp Lys
    530                 535                 540
Leu Pro His Ile Phe Gly Phe Thr Leu Leu Gly Asp Phe Ile Tyr Trp
545                 550                 555                 560
Thr Asp Trp Gln Arg Arg Ser Ile Glu Arg Val His Lys Val Lys Ala
                565                 570                 575
Ser Arg Asp Val Ile Ile Asp Gln Leu Pro Asp Leu Met Gly Leu Lys
            580                 585                 590
Ala Val Asn Val Ala Lys Val Val Gly Thr Asn Pro Cys Ala Asp Arg
        595                 600                 605
Asn Gly Gly Cys Ser His Leu Cys Phe Phe Thr Pro His Ala Thr Arg
    610                 615                 620
```

-continued

```
Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
            645                 650                 655

Arg Ile Ser Leu Glu Thr Asn Asn Asp Val Ala Ile Pro Leu Thr
        660                 665                 670

Gly Val Lys Glu Ala Ser Ala Leu Asp Phe Asp Val Ser Asn Asn His
            675                 680                 685

Ile Tyr Trp Thr Asp Val Ser Leu Lys Thr Ile Ser Arg Ala Phe Met
690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
            725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
        755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
            805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
            885                 890                 895

Ser Ser Arg Gln Asp Gly Leu Asn Asp Cys Met His Asn Asn Gly Gln
        900                 905                 910

Cys Gly Gln Leu Cys Leu Ala Ile Pro Gly Gly His Arg Cys Gly Cys
        915                 920                 925

Ala Ser His Tyr Thr Leu Asp Pro Ser Ser Arg Asn Cys Ser Pro Pro
930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
            965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
            995                 1000                1005

Gln Pro Phe Val Leu Thr Ser Leu Ser Gln Gly Gln Asn Pro Asp
    1010                1015                1020

Arg Gln Pro His Asp Leu Ser Ile Asp Ile Tyr Ser Arg Thr Leu
    1025                1030                1035

Phe Trp Thr Cys Glu Ala Thr Asn Thr Ile Asn Val His Arg Leu
```

|  |  |  |  |  |  |  |  |  |  |
|---|---|---|---|---|---|---|---|---|---|
|  | 1040 |  |  | 1045 |  |  | 1050 |  |  |
| Ser | Gly | Glu | Ala | Met | Gly | Val | Val | Leu | Arg | Gly | Asp | Arg | Asp | Lys |
| 1055 | | | | | 1060 | | | | | 1065 | | | | |
| Pro | Arg | Ala | Ile | Val | Val | Asn | Ala | Glu | Arg | Gly | Tyr | Leu | Tyr | Phe |
| 1070 | | | | | 1075 | | | | | 1080 | | | | |
| Thr | Asn | Met | Gln | Asp | Arg | Ala | Ala | Lys | Ile | Glu | Arg | Ala | Ala | Leu |
| 1085 | | | | | 1090 | | | | | 1095 | | | | |
| Asp | Gly | Thr | Glu | Arg | Glu | Val | Leu | Phe | Thr | Thr | Gly | Leu | Ile | Arg |
| 1100 | | | | | 1105 | | | | | 1110 | | | | |
| Pro | Val | Ala | Leu | Val | Val | Asp | Asn | Thr | Leu | Gly | Lys | Leu | Phe | Trp |
| 1115 | | | | | 1120 | | | | | 1125 | | | | |
| Val | Asp | Ala | Asp | Leu | Lys | Arg | Ile | Glu | Ser | Cys | Asp | Leu | Ser | Gly |
| 1130 | | | | | 1135 | | | | | 1140 | | | | |
| Ala | Asn | Arg | Leu | Thr | Leu | Glu | Asp | Ala | Asn | Ile | Val | Gln | Pro | Leu |
| 1145 | | | | | 1150 | | | | | 1155 | | | | |
| Gly | Leu | Thr | Ile | Leu | Gly | Lys | His | Leu | Tyr | Trp | Ile | Asp | Arg | Gln |
| 1160 | | | | | 1165 | | | | | 1170 | | | | |
| Gln | Gln | Met | Ile | Glu | Arg | Val | Glu | Lys | Thr | Thr | Gly | Asp | Lys | Arg |
| 1175 | | | | | 1180 | | | | | 1185 | | | | |
| Thr | Arg | Ile | Gln | Gly | Arg | Val | Ala | His | Leu | Thr | Gly | Ile | His | Ala |
| 1190 | | | | | 1195 | | | | | 1200 | | | | |
| Val | Glu | Glu | Val | Ser | Leu | Glu | Glu | Phe | Ser | Ala | His | Pro | Cys | Ala |
| 1205 | | | | | 1210 | | | | | 1215 | | | | |
| Arg | Asp | Asn | Gly | Gly | Cys | Ser | His | Ile | Cys | Ile | Ala | Lys | Gly | Asp |
| 1220 | | | | | 1225 | | | | | 1230 | | | | |
| Gly | Thr | Pro | Arg | Cys | Ser | Cys | Pro | Val | His | Leu | Val | Leu | Leu | Gln |
| 1235 | | | | | 1240 | | | | | 1245 | | | | |
| Asn | Leu | Leu | Thr | Cys | Gly | Glu | Pro | Pro | Thr | Cys | Ser | Pro | Asp | Gln |
| 1250 | | | | | 1255 | | | | | 1260 | | | | |
| Phe | Ala | Cys | Ala | Thr | Gly | Glu | Ile | Asp | Cys | Ile | Pro | Gly | Ala | Trp |
| 1265 | | | | | 1270 | | | | | 1275 | | | | |
| Arg | Cys | Asp | Gly | Phe | Pro | Glu | Cys | Asp | Asp | Gln | Ser | Asp | Glu | Glu |
| 1280 | | | | | 1285 | | | | | 1290 | | | | |
| Gly | Cys | Pro | Val | Cys | Ser | Ala | Ala | Gln | Phe | Pro | Cys | Ala | Arg | Gly |
| 1295 | | | | | 1300 | | | | | 1305 | | | | |
| Gln | Cys | Val | Asp | Leu | Arg | Leu | Arg | Cys | Asp | Gly | Glu | Ala | Asp | Cys |
| 1310 | | | | | 1315 | | | | | 1320 | | | | |
| Gln | Asp | Arg | Ser | Asp | Glu | Ala | Asp | Cys | Asp | Ala | Ile | Cys | Leu | Pro |
| 1325 | | | | | 1330 | | | | | 1335 | | | | |
| Asn | Gln | Phe | Arg | Cys | Ala | Ser | Gly | Gln | Cys | Val | Leu | Ile | Lys | Gln |
| 1340 | | | | | 1345 | | | | | 1350 | | | | |
| Gln | Cys | Asp | Ser | Phe | Pro | Asp | Cys | Ile | Asp | Gly | Ser | Asp | Glu | Leu |
| 1355 | | | | | 1360 | | | | | 1365 | | | | |
| Met | Cys | Glu | Ile | Thr | Lys | Pro | Pro | Ser | Asp | Asp | Ser | Pro | Ala | His |
| 1370 | | | | | 1375 | | | | | 1380 | | | | |

<210> SEQ ID NO 7
<211> LENGTH: 4161
<212> TYPE: DNA
<213> ORGANISM: Mouse

<400> SEQUENCE: 7

```
atggaggcag cgccgcccgg gccgccgtgg ccgctgctgc tgctgctgct gctgctgctg      60
gcgctgtgcg gctgcccggc cccgccgcg gcctcgccgc tcctgctatt tgccaaccgc     120
```

```
cgggacgtac ggctggtgga cgccggcgga gtcaagctgg agtccaccat cgtggtcagc    180
ggcctggagg atgcggccgc agtggacttc cagtttttcca agggagccgt gtactggaca    240
gacgtgagcg aggaggccat caagcagacc tacctgaacc agacggggc cgccgtgcag     300 aacgtggtca tctccggcct ggtctctccc gacggcctcg cctgcgactg ggtgggcaag    360
aagctgtact ggacggactc agagaccaac cgcatcgagg tggccaacct caatggcaca    420
tcccggaagg tgctcttctg gcaggacctt gaccagccga gggccatcgc cttggacccc    480
gctcacgggt acatgtactg gacagactgg ggtgagacgc cccggattga gcgggcaggg    540
atggatggca gcacccggaa gatcattgtg gactcggaca tttactggcc caatggactg    600
accatcgacc tggaggagca gaagctctac tgggctgacg ccaagctcag cttcatccac    660
cgtgccaacc tggacggctc gttccggcag aaggtggtgg agggcagcct gacgcacccc    720
ttcgccctga cgctctccgg ggacactctg tactggacag actggcagac ccgctccatc    780
catgcctgca acaagcgcac tggggggaag aggaaggaga tcctgagtgc cctctactca    840
cccatggaca tccaggtgct gagccaggag cggcagcctt tcttccacac tcgctgtgag    900
gaggacaatg gcggctgctc ccacctgtgc ctgctgtccc caagcgagcc tttctacaca    960
tgcgcctgcc ccacgggtgt gcagctgcag gacaacggca ggacgtgtaa ggcaggagcc    1020
gaggaggtgc tgctgctggc ccggcggacg gacctacgga ggatctcgct ggacacgccg    1080
gactttaccg acatcgtgct gcaggtggac gacatccggc acgccattgc catcgactac    1140
gacccgctag agggctatgt ctactggaca gatgacgagg tgcgggccat ccgcagggcg    1200
tacctggacg ggtctggggc gcagacgctg gtcaacaccg agatcaacga ccccgatggc    1260
atcgcggtcg actgggtggc ccgaaaactc tactggaccg acacgggcac ggaccgcatc    1320
gaggtgacgc gcctcaacgg cacctcccgc aagatcctgg tgtcggagga cctggacgag    1380
ccccgagcca tcgcactgca ccccgtgatg ggcctcatgt actggacaga ctggggagag    1440
aaccctaaaa tcgagtgtgc caacttggat gggcaggagc ggcgtgtgct ggtcaatgcc    1500
tccctcgggt ggcccaacgg cctggccctg gacctgcagg aggggaagct ctactgggga    1560
gacgccaaga cagacaagat cgaggtgatc aatgttgatg ggacgaagag gcggacccto    1620 ctggaggaca agctcccgca cattttcggg ttcacgctgc tgggggactt catctactgg    1680
actgactggc agcgccgcag catcgagcgg gtgcacaagg tcaaggccag ccgggacgtc    1740
atcattgacc agctgcccga cctgatgggg ctcaaagctg tgaatgtggc caaggtcgtc    1800
ggaaccaacc cgtgtgcgga caggaacggg gggtgcagcc acctgtgctt cttcacaccc    1860
cacgcaaccc ggtgtggctg ccccatcggc ctggagctgc tgagtgacat gaagacctgc    1920
atcgtgcctg aggccttctt ggtcttcacc agcagagccg ccatccacag gatctccctc    1980
gagaccaata caacgacgt ggccatcccg ctcacgggcg tcaaggaggc ctcagccctg    2040
gactttgatg tgtccaacaa ccacatctac tggacagacg tcagcctgaa gaccatcagc    2100
cgcgccttca tgaacgggag ctcggtggag cacgtggtgg agtttggcct tgactacccc    2160
gagggcatgg ccgttgactg gatgggcaag aacctctact gggccgacac tgggaccaac    2220
agaatcgaag tggcgcggct ggacgggcag ttccggcaag tcctcgtgtg gagggacttg    2280
gacaacccga ggtcgctggc cctggatccc accaagggct acatctactg gaccgagtgg    2340
ggcggcaagc cgaggatcgt gcgggccttc atggacggga ccaactgcat gacgctggtg    2400
gacaaggtgg gccgggccaa cgacctcacc attgactacg ctgaccagcg cctctactgg    2460
```

-continued

```
accgacctgg acaccaacat gatcgagtcg tccaacatgc tgggtcagga gcgggtcgtg    2520
attgccgacg atctcccgca cccgttcggt ctgacgcagt acagcgatta tatctactgg    2580
acagactgga atctgcacag cattgagcgg gccgacaaga ctagcggccg gaaccgcacc    2640
ctcatccagg gccacctgga cttcgtgatg gacatcctgg tgttccactc ctcccgccag    2700
gatggcctca atgactgtat gcacaacaac gggcagtgtg ggcagctgtg ccttgccatc    2760 cccgcggcc accgctgcgg ctgcgcctca cactacaccc tggaccccag cagccgcaac    2820
tgcagcccgc ccaccacctt cttgctgttc agccagaaat ctgccatcag tcggatgatc    2880
ccggacgacc agcacagccc ggatctcatc ctgcccctgc atggactgag gaacgtcaaa    2940
gccatcgact atgacccact ggacaagttc atctactggg tggatgggcg ccagaacatc    3000
aagcgagcca aggacgacgg gacccagccc tttgttttga cctctctgag ccaaggccaa    3060
aacccagaca ggcagcccca cgacctcagc atcgacatct acagccggac actgttctgg    3120
acgtgcgagg ccaccaatac catcaacgtc cacaggctga gcggggaagc catgggggtg    3180
gtgctgcgtg gggaccgcga caagcccagg gccatcgtcg tcaacgcgga gcgagggtac    3240
ctgtacttca ccaacatgca ggaccgggca gccaagatcg aacgcgcagc cctggacggc    3300
accgagcgcg aggtcctctt caccaccggc ctcatccgcc ctgtggccct ggtggtagac    3360
aacacactgg gcaagctgtt ctgggtggac gcggacctga gcgcattga gctgtgac    3420 ctgtcagggg ccaaccgcct gaccctggag gacgccaaca tcgtgcagcc tctgggcctg    3480
accatccttg gcaagcatct ctactggatc gaccgccagc agcagatgat cgagcgtgtg    3540
gagaagacca ccggggacaa gcggactcgc atccagggcc gtgtcgccca cctcactggc    3600
atccatgcag tggaggaagt cagcctggag gagttctcag cccacccatg tgcccgtgac    3660
aatggtggct gctcccacat ctgtattgcc aagggtgatg ggacaccacg gtgctcatgc    3720
ccagtccacc tcgtgctcct gcagaacctg ctgacctgtg agagccgcc cacctgctcc    3780 ccggaccagt ttgcatgtgc cacaggggag atcgactgta tccccgggc ctggcgctgt    3840 gacggctttc ccgagtgcga tgaccagagc gacgaggagg ctgccccgt gtgctccgcc    3900 gcccagttcc cctgcgcgcg gggtcagtgt gtggacctgc cctgcgctg cgacggcgag    3960 gcagactgtc aggaccgctc agacgaggcg gactgtgacg ccatctgcct gcccaaccag    4020
ttccggtgtg cgagcggcca gtgtgtcctc atcaaacagc agtgcgactc cttccccgac    4080
tgtatcgacg gctccgacga gctcatgtgt gaaatcacca agccgccctc agacgacagc    4140
ccggcccaca gcagtgccat c                                            4161
```

<210> SEQ ID NO 8
<211> LENGTH: 4842
<212> TYPE: PRT
<213> ORGANISM: Mouse

<400> SEQUENCE: 8

```
Ala Thr Gly Gly Gly Gly Cys Cys Gly Thr Gly Cys Thr Gly Ala
 1               5                   10                  15

Gly Gly Ala Gly Cys Cys Thr Cys Cys Thr Gly Gly Cys Cys Thr Gly
                20                  25                  30

Cys Ala Gly Cys Thr Thr Cys Thr Gly Cys Gly Thr Gly Cys Thr Gly
                35                  40                  45

Cys Thr Gly Ala Gly Ala Gly Cys Gly Gly Cys Cys Cys Thr Thr
            50                  55                  60

Thr Gly Thr Thr Gly Cys Thr Thr Thr Ala Thr Gly Cys Ala Ala Ala
```

-continued

```
65                  70                  75                  80

Cys Ala Gly Ala Cys Gly Gly Gly Ala Cys Thr Thr Gly Ala Gly Ala
                85                  90                  95

Thr Thr Gly Gly Thr Thr Gly Ala Thr Gly Cys Thr Ala Cys Ala Ala
            100                 105                 110

Ala Thr Gly Gly Cys Ala Ala Ala Gly Ala Gly Ala Ala Thr Gly Cys
        115                 120                 125

Ala Ala Cys Gly Ala Thr Thr Gly Thr Ala Gly Thr Thr Gly Gly Ala
    130                 135                 140

Gly Gly Cys Thr Thr Gly Gly Ala Gly Gly Ala Thr Gly Cys Ala Gly
145                 150                 155                 160

Cys Thr Gly Cys Gly Gly Thr Gly Gly Ala Cys Thr Thr Thr Gly Thr
                165                 170                 175
Gly Thr Thr Thr Gly Gly Thr Cys Ala Thr Gly Gly Cys Thr Thr Gly
            180                 185                 190

Ala Thr Ala Thr Ala Cys Thr Gly Gly Ala Gly Thr Gly Ala Thr Gly
        195                 200                 205

Thr Cys Ala Gly Cys Gly Ala Ala Gly Ala Ala Gly Cys Cys Ala Thr
    210                 215                 220

Thr Ala Ala Ala Cys Gly Ala Ala Cys Ala Gly Ala Ala Thr Thr Thr
225                 230                 235                 240

Ala Ala Cys Ala Ala Ala Ala Gly Thr Gly Ala Ala Ala Gly Thr Gly
                245                 250                 255

Thr Ala Cys Ala Gly Ala Ala Thr Gly Thr Thr Gly Thr Thr Gly Thr
            260                 265                 270

Thr Thr Cys Thr Gly Gly Ala Thr Thr Ala Thr Thr Gly Thr Cys Cys
        275                 280                 285

Cys Cys Gly Gly Ala Thr Gly Gly Gly Cys Thr Gly Gly Cys Ala Thr
    290                 295                 300

Gly Thr Gly Ala Thr Thr Gly Gly Cys Thr Thr Gly Gly Ala Gly Ala
305                 310                 315                 320

Ala Ala Ala Ala Thr Thr Gly Thr Ala Cys Thr Gly Gly Ala Cys Ala
                325                 330                 335

Gly Ala Thr Thr Cys Thr Gly Ala Ala Ala Cys Thr Ala Ala Thr Cys
            340                 345                 350

Gly Thr Ala Thr Thr Gly Ala Ala Gly Thr Thr Thr Cys Thr Ala Ala
        355                 360                 365

Thr Thr Thr Ala Gly Ala Thr Gly Gly Ala Thr Cys Thr Thr Thr Ala
    370                 375                 380

Cys Gly Ala Ala Ala Ala Gly Thr Thr Thr Thr Ala Thr Thr Thr Thr
385                 390                 395                 400

Gly Gly Cys Ala Ala Gly Ala Gly Thr Thr Gly Gly Ala Thr Cys Ala
                405                 410                 415

Ala Cys Cys Cys Ala Gly Ala Gly Cys Thr Ala Thr Thr Gly Cys Cys
            420                 425                 430

Thr Thr Ala Gly Ala Thr Cys Cys Ala Thr Cys Ala Ala Gly Thr Gly
        435                 440                 445

Gly Gly Thr Thr Cys Ala Thr Gly Thr Ala Cys Thr Gly Gly Ala Cys
    450                 455                 460

Ala Gly Ala Cys Thr Gly Gly Gly Gly Ala Gly Ala Ala Gly Thr Gly
465                 470                 475                 480

Cys Cys Ala Ala Ala Gly Ala Thr Ala Gly Ala Ala Cys Gly Gly Gly
                485                 490                 495
```

-continued

Cys Thr Gly Gly Gly Ala Thr Gly Gly Ala Thr Gly Cys Thr Cys
            500                 505                 510
Ala Ala Gly Thr Cys Gly Cys Thr Thr Cys Gly Thr Ala Thr Ala
            515                 520                 525
Ala Thr Ala Ala Ala Cys Ala Cys Gly Gly Ala Gly Ala Thr Thr Thr
            530                 535                 540
Ala Cys Thr Gly Gly Cys Cys Ala Ala Cys Gly Gly Ala Cys Thr
545                 550                 555                 560
Gly Ala Cys Thr Cys Thr Gly Gly Ala Thr Thr Ala Thr Cys Ala Gly
            565                 570                 575
Gly Ala Gly Cys Gly Gly Ala Ala Gly Cys Thr Thr Ala Cys Thr
            580                 585                 590
Gly Gly Gly Cys Cys Gly Ala Thr Gly Cys Ala Ala Ala Cys Thr
            595                 600                 605
Thr Ala Ala Thr Thr Thr Cys Ala Thr Cys Cys Ala Thr Ala Ala Ala
            610                 615                 620
Thr Cys Ala Ala Ala Cys Cys Thr Gly Gly Ala Thr Gly Gly Ala Ala
625                 630                 635                 640
Cys Ala Ala Ala Cys Cys Gly Gly Cys Ala Gly Gly Cys Ala Gly Thr
            645                 650                 655
Gly Gly Thr Thr Ala Ala Ala Gly Gly Thr Thr Cys Cys Cys Thr Thr
            660                 665                 670
Cys Cys Ala Cys Ala Thr Cys Cys Thr Thr Thr Gly Cys Cys Thr
            675                 680                 685
Thr Gly Ala Cys Gly Thr Thr Ala Thr Thr Thr Gly Ala Gly Gly Ala
            690                 695                 700
Cys Ala Cys Ala Thr Thr Gly Thr Ala Cys Thr Gly Gly Ala Cys Thr
705                 710                 715                 720
Gly Ala Cys Thr Gly Gly Ala Ala Thr Ala Cys Ala Cys Ala Cys Thr
            725                 730                 735
Cys Thr Ala Thr Thr Thr Thr Gly Gly Cys Thr Thr Gly Cys Ala Ala
            740                 745                 750
Cys Ala Ala Ala Thr Ala Thr Ala Cys Thr Gly Gly Cys Gly Ala Gly
            755                 760                 765
Gly Gly Thr Cys Thr Gly Cys Gly Thr Gly Ala Ala Ala Thr Thr Cys
            770                 775                 780
Ala Thr Thr Cys Thr Ala Ala Cys Ala Thr Cys Thr Thr Cys Thr Cys
785                 790                 795                 800
Thr Cys Cys Cys Ala Thr Gly Gly Ala Thr Ala Thr Cys Ala Thr
            805                 810                 815
Gly Cys Thr Thr Thr Cys Ala Gly Cys Cys Ala Ala Cys Ala Gly Ala
            820                 825                 830
Gly Gly Cys Ala Gly Cys Cys Ala Ala Ala Thr Gly Cys Thr Ala Cys
            835                 840                 845
Ala Ala Ala Thr Cys Cys Ala Thr Gly Thr Gly Gly Ala Ala Thr Thr
            850                 855                 860
Gly Ala Thr Ala Ala Thr Gly Gly Thr Gly Gly Thr Gly Thr Gly Thr Thr
865                 870                 875                 880
Cys Cys Cys Ala Thr Thr Gly Thr Gly Thr Thr Thr Gly Ala Thr
            885                 890                 895
Gly Thr Cys Thr Cys Cys Ala Gly Thr Cys Ala Ala Gly Cys Cys Thr
            900                 905                 910

-continued

```
Thr Thr Thr Thr Ala Thr Cys Ala Gly Thr Gly Thr Gly Cys Thr Thr
        915                 920                 925

Gly Cys Cys Cys Ala Ala Cys Thr Gly Gly Gly Gly Thr Cys Ala Ala
    930                 935                 940

Gly Cys Thr Gly Ala Thr Gly Gly Ala Gly Ala Ala Thr Gly Gly Ala
945                 950                 955                 960

Ala Ala Gly Ala Cys Cys Thr Gly Cys Ala Ala Ala Gly Ala Thr Gly
                965                 970                 975

Gly Thr Gly Cys Cys Ala Cys Thr Gly Ala Ala Cys Thr Ala Thr Thr
            980                 985                 990

Gly Cys Thr Gly Thr Thr Ala Gly  Cys Cys Cys Gly Ala  Cys Gly Gly
        995                 1000                1005

Ala Cys  Ala Gly Ala Cys Thr  Thr Gly Ala Gly Gly  Cys Gly Ala
    1010                1015                1020

Ala Thr  Thr Thr Cys Thr Thr  Thr Gly Gly Ala Thr  Ala Cys Ala
    1025                1030                1035

Cys Cys  Cys Gly Ala Thr Thr  Thr Thr Ala Cys Thr  Gly Ala Cys
    1040                1045                1050

Ala Thr  Thr Gly Thr Thr Cys  Thr Gly Cys Ala Gly  Thr Thr Ala
    1055                1060                1065

Gly Ala  Ala Gly Ala Thr Ala  Thr Cys Cys Gly Gly  Cys Ala Thr
    1070                1075                1080

Gly Cys  Cys Ala Thr Thr Gly  Cys Cys Ala Thr Ala  Gly Ala Cys
    1085                1090                1095

Thr Ala  Thr Gly Ala Cys Cys  Cys Thr Gly Thr Ala  Gly Ala Ala
    1100                1105                1110

Gly Gly  Cys Thr Ala Cys Ala  Thr Ala Thr Ala Cys  Thr Gly Gly
    1115                1120                1125

Ala Cys  Ala Gly Ala Thr Gly  Ala Cys Gly Ala Ala  Gly Thr Gly
    1130                1135                1140

Ala Gly  Gly Gly Cys Thr Ala  Thr Cys Cys Gly Thr  Cys Gly Cys
    1145                1150                1155

Thr Cys  Cys Thr Thr Cys Ala  Thr Ala Gly Ala Thr  Gly Gly Ala
    1160                1165                1170

Thr Cys  Thr Gly Gly Cys Ala  Gly Thr Cys Ala Gly  Thr Thr Thr
    1175                1180                1185

Gly Thr  Gly Gly Thr Cys Ala  Cys Gly Gly Cys Cys  Cys Ala Gly
    1190                1195                1200

Ala Thr  Thr Gly Cys Thr Cys  Ala Thr Cys Cys Thr  Gly Ala Thr
    1205                1210                1215

Gly Gly  Thr Ala Thr Thr Gly  Cys Thr Gly Thr Thr  Gly Ala Cys
    1220                1225                1230

Thr Gly  Gly Gly Thr Thr Gly  Cys Ala Ala Gly Gly  Ala Ala Cys
    1235                1240                1245

Cys Thr  Gly Thr Ala Cys Thr  Gly Gly Ala Cys Ala  Gly Ala Cys
    1250                1255                1260

Ala Cys  Thr Gly Gly Cys Ala  Cys Gly Gly Ala Thr  Cys Gly Thr
    1265                1270                1275

Ala Thr  Ala Gly Ala Ala Gly  Thr Gly Ala Cys Ala  Ala Gly Gly
    1280                1285                1290

Cys Thr  Cys Ala Ala Thr Gly  Gly Gly Ala Cys Cys  Ala Thr Gly
    1295                1300                1305

Ala Gly  Gly Ala Ala Gly Ala  Thr Cys Thr Thr Gly  Ala Thr Thr
```

-continued

```
                1310                1315                1320
Thr Cys Ala Gly Ala Gly Gly Ala Cys Thr Thr Ala Gly Ala Gly
    1325                1330                1335
Gly Ala Gly Cys Cys Cys Cys Gly Gly Gly Cys Thr Ala Thr Cys
    1340                1345                1350
Gly Thr Gly Thr Thr Ala Gly Ala Thr Cys Cys Ala Thr Gly
    1355                1360                1365
Gly Thr Thr Gly Gly Gly Thr Ala Cys Ala Thr Gly Thr Ala Thr
    1370                1375                1380
Thr Gly Gly Ala Cys Ala Gly Ala Cys Thr Gly Gly Gly Ala
    1385                1390                1395
Gly Ala Ala Ala Thr Cys Cys Ala Ala Ala Ala Thr Ala
    1400                1405                1410
Gly Ala Gly Cys Gly Ala Gly Cys Thr Gly Cys Thr Cys Thr Gly
    1415                1420                1425
Gly Ala Cys Gly Gly Ala Thr Cys Thr Gly Ala Cys Cys Gly Ala
    1430                1435                1440
Gly Thr Ala Gly Thr Thr Cys Thr Thr Gly Thr Cys Ala Ala Cys
    1445                1450                1455
Ala Cys Thr Thr Cys Cys Thr Thr Gly Gly Thr Thr Gly Gly
    1460                1465                1470
Cys Cys Ala Ala Ala Cys Gly Gly Cys Thr Ala Gly Cys Cys
    1475                1480                1485
Cys Thr Gly Gly Ala Thr Thr Ala Thr Gly Ala Thr Gly Ala Ala
    1490                1495                1500
Gly Gly Cys Ala Cys Ala Ala Thr Ala Thr Ala Cys Thr Gly Gly
    1505                1510                1515
Gly Gly Ala Gly Ala Thr Gly Cys Cys Ala Ala Ala Cys Ala
    1520                1525                1530
Gly Ala Cys Ala Ala Ala Thr Thr Gly Ala Gly Gly Thr Thr
    1535                1540                1545
Ala Thr Gly Ala Ala Thr Ala Cys Cys Gly Ala Thr Gly Gly Cys
    1550                1555                1560
Ala Cys Cys Gly Gly Gly Ala Gly Gly Cys Gly Ala Gly Thr Gly
    1565                1570                1575
Cys Thr Gly Gly Thr Gly Gly Ala Ala Gly Ala Cys Ala Ala Gly
    1580                1585                1590
Ala Thr Cys Cys Cys Thr Cys Ala Cys Ala Thr Thr Thr
    1595                1600                1605
Gly Gly Gly Thr Thr Thr Ala Cys Cys Thr Thr Gly Cys Thr Gly
    1610                1615                1620
Gly Gly Thr Gly Ala Cys Thr Ala Thr Gly Thr Thr Ala Cys
    1625                1630                1635
Thr Gly Gly Ala Cys Thr Gly Ala Cys Thr Gly Gly Cys Ala Gly
    1640                1645                1650
Ala Gly Gly Cys Gly Gly Ala Gly Cys Thr Cys Gly Ala Gly
    1655                1660                1665
Ala Gly Ala Gly Thr Ala Cys Ala Cys Ala Ala Cys Gly Gly
    1670                1675                1680
Ala Gly Cys Gly Cys Ala Gly Ala Gly Ala Gly Gly Ala Ala
    1685                1690                1695
Gly Thr Cys Ala Thr Cys Ala Thr Ala Gly Ala Cys Cys Ala Gly
    1700                1705                1710
```

-continued

Cys Thr Gly Cys Cys Ala Gly Ala Cys Cys Ala Thr Gly
1715                1720                1725

Gly Gly Ala Cys Thr Gly Ala Ala Gly Gly Cys Cys Ala Cys Ala
1730                1735                1740

Ala Gly Thr Gly Thr Thr Cys Ala Cys Ala Gly Ala Gly Thr Cys
1745                1750                1755

Ala Thr Thr Gly Gly Thr Thr Cys Thr Ala Ala Cys Cys Cys Cys
1760                1765                1770

Thr Gly Thr Gly Cys Thr Gly Ala Gly Gly Ala Cys Ala Ala Thr
1775                1780                1785

Gly Gly Ala Gly Gly Ala Thr Gly Thr Ala Gly Cys Cys Ala Thr
1790                1795                1800

Cys Thr Thr Thr Gly Cys Cys Thr Gly Thr Ala Cys Ala Gly Gly
1805                1810                1815

Cys Cys Thr Cys Ala Gly Gly Gly Gly Cys Thr Thr Cys Gly Ala
1820                1825                1830

Thr Gly Cys Gly Cys Cys Thr Gly Thr Cys Cys Cys Ala Thr Thr
1835                1840                1845

Gly Gly Cys Thr Thr Thr Gly Ala Gly Cys Thr Cys Ala Thr Cys
1850                1855                1860

Gly Gly Thr Gly Ala Cys Ala Thr Gly Ala Ala Gly Ala Cys Ala
1865                1870                1875

Thr Gly Cys Ala Thr Thr Gly Thr Cys Cys Cys Cys Gly Ala Gly
1880                1885                1890

Gly Cys Thr Thr Thr Cys Cys Thr Thr Cys Thr Gly Thr Thr Cys
1895                1900                1905

Thr Cys Gly Ala Gly Gly Ala Gly Ala Gly Cys Gly Gly Ala Thr
1910                1915                1920

Ala Thr Cys Ala Gly Ala Cys Gly Cys Ala Thr Ala Thr Cys Thr
1925                1930                1935

Thr Thr Gly Gly Ala Ala Ala Cys Ala Ala Ala Cys Ala Ala Cys
1940                1945                1950

Ala Ala Cys Ala Ala Thr Gly Thr Gly Gly Cys Cys Ala Thr Thr
1955                1960                1965

Cys Cys Thr Cys Thr Cys Ala Cys Thr Gly Gly Thr Gly Thr Cys
1970                1975                1980

Ala Ala Ala Gly Ala Ala Gly Cys Cys Thr Cys Thr Gly Cys Thr
1985                1990                1995

Thr Thr Gly Gly Ala Thr Thr Thr Thr Gly Ala Thr Gly Thr Cys
2000                2005                2010

Ala Cys Ala Gly Ala Cys Ala Ala Cys Ala Gly Gly Ala Thr Thr
2015                2020                2025

Thr Ala Cys Thr Gly Gly Ala Cys Thr Gly Ala Thr Ala Thr Ala
2030                2035                2040

Thr Cys Ala Cys Thr Gly Ala Ala Gly Ala Cys Thr Ala Thr Thr
2045                2050                2055

Ala Gly Cys Ala Gly Ala Gly Cys Cys Thr Thr Thr Ala Thr Gly
2060                2065                2070

Ala Ala Thr Gly Gly Cys Ala Gly Thr Gly Cys Ala Cys Thr Gly
2075                2080                2085

Gly Ala Ala Cys Ala Thr Gly Thr Gly Gly Thr Ala Gly Ala Gly
2090                2095                2100

```
Thr Thr Thr Gly Gly Cys Thr Ala Gly Ala Thr Ala Thr
    2105                2110                2115

Cys Cys Ala Gly Ala Ala Gly Gly Cys Ala Thr Gly Gly Cys Ala
    2120                2125                2130

Gly Thr Gly Gly Ala Cys Thr Gly Gly Cys Thr Thr Gly Gly Gly
    2135                2140                2145

Ala Ala Gly Ala Ala Cys Thr Thr Ala Thr Ala Cys Thr Gly Gly
    2150                2155                2160

Gly Cys Ala Gly Ala Cys Ala Cys Ala Gly Gly Ala Ala Cys Ala
    2165                2170                2175

Ala Ala Thr Cys Gly Cys Ala Thr Thr Gly Ala Gly Gly Thr Ala
    2180                2185                2190

Thr Cys Ala Ala Ala Gly Thr Thr Gly Gly Ala Cys Gly Gly Ala
    2195                2200                2205

Cys Ala Gly Cys Ala Cys Cys Gly Ala Cys Ala Gly Gly Thr Thr
    2210                2215                2220

Thr Thr Gly Gly Thr Ala Thr Gly Gly Ala Ala Ala Gly Ala Cys
    2225                2230                2235

Cys Thr Thr Gly Ala Cys Ala Gly Thr Cys Cys Thr Cys Gly Ala
    2240                2245                2250

Gly Cys Thr Cys Thr Gly Gly Cys Ala Cys Thr Gly Gly Ala Thr
    2255                2260                2265

Cys Cys Thr Gly Cys Thr Gly Ala Ala Gly Gly Gly Thr Thr Thr
    2270                2275                2280

Ala Thr Gly Thr Ala Thr Thr Gly Gly Ala Cys Thr Gly Ala Gly
    2285                2290                2295

Thr Gly Gly Gly Gly Ala Gly Gly Cys Ala Ala Gly Cys Cys Thr
    2300                2305                2310

Ala Ala Gly Ala Thr Thr Gly Ala Cys Ala Gly Gly Gly Cys Thr
    2315                2320                2325

Gly Cys Thr Ala Thr Gly Gly Ala Thr Gly Gly Ala Ala Gly Thr
    2330                2335                2340

Gly Ala Ala Cys Gly Cys Ala Cys Thr Ala Cys Ala Thr Thr Ala
    2345                2350                2355

Gly Thr Thr Cys Cys Ala Ala Ala Thr Gly Thr Ala Gly Gly Cys
    2360                2365                2370

Cys Gly Ala Gly Cys Ala Ala Ala Thr Gly Gly Thr Cys Thr Cys
    2375                2380                2385

Ala Cys Cys Ala Thr Cys Gly Ala Cys Thr Ala Thr Gly Cys Thr
    2390                2395                2400

Ala Ala Ala Ala Gly Gly Cys Gly Gly Cys Thr Thr Thr Ala Cys
    2405                2410                2415

Thr Gly Gly Ala Cys Ala Gly Ala Cys Cys Thr Gly Gly Ala Cys
    2420                2425                2430

Ala Cys Thr Ala Ala Cys Cys Thr Ala Ala Thr Ala Gly Ala Ala
    2435                2440                2445

Thr Cys Cys Thr Cys Ala Gly Ala Thr Ala Thr Gly Cys Thr Cys
    2450                2455                2460

Gly Gly Ala Cys Thr Cys Ala Ala Cys Cys Gly Thr Gly Ala Ala
    2465                2470                2475

Gly Thr Thr Ala Thr Ala Gly Cys Ala Gly Ala Thr Gly Ala Cys
    2480                2485                2490

Thr Thr Gly Cys Cys Thr Cys Ala Thr Cys Cys Thr Thr Thr Thr
```

-continued

```
            2495                2500                2505
Gly Gly Cys Thr Thr Ala Ala Cys Thr Cys Ala  Gly Thr Ala Cys
        2510                2515                2520
Cys Ala Ala Gly Ala Thr Thr Ala Cys Ala Thr  Cys Thr Ala Cys
        2525                2530                2535
Thr Gly Gly Ala Cys Ala Gly Ala Cys Thr Gly  Gly Ala Gly Cys
        2540                2545                2550
Cys Gly Ala Cys Gly Cys Ala Gly Cys Ala Thr  Gly Ala Ala
        2555                2560                2565
Cys Gly Thr Gly Cys Cys Ala Ala Cys Ala Ala  Ala Cys Cys
        2570                2575                2580
Ala Gly Thr Gly Gly Cys Cys Ala Ala Ala Cys  Cys Gly Cys
        2585                2590                2595
Ala Cys Cys Ala Thr Cys Ala Thr Cys Cys Ala  Gly Gly Gly Cys
        2600                2605                2610
Cys Ala Thr Thr Thr Gly Gly Ala Cys Thr Ala  Thr Gly Thr Gly
        2615                2620                2625
Ala Thr Gly Gly Ala Cys Ala Thr Cys Cys Thr  Gly Gly Thr Cys
        2630                2635                2640
Thr Thr Cys Cys Ala Cys Thr Cys Thr Cys Cys  Cys Gly Gly
        2645                2650                2655
Cys Ala Gly Gly Cys Ala Gly Gly Thr Gly Gly  Gly Ala Ala Thr
        2660                2665                2670
Gly Ala Gly Thr Gly Thr Gly Cys Cys Thr Cys  Cys Ala Gly Cys
        2675                2680                2685
Ala Ala Cys Gly Gly Gly Cys Ala Cys Thr Gly  Cys Thr Cys Cys
        2690                2695                2700
Cys Ala Cys Cys Thr Cys Thr Gly Cys Thr Thr  Gly Gly Cys Thr
        2705                2710                2715
Gly Thr Gly Cys Cys Cys Gly Thr Cys Gly Gly  Ala Gly Gly Thr
        2720                2725                2730
Thr Thr Thr Gly Thr Gly Thr Gly Thr Gly Gly  Ala Thr Gly Cys
        2735                2740                2745
Cys Cys Thr Gly Cys Cys Cys Ala Cys Thr Ala  Cys Thr Cys Cys
        2750                2755                2760
Cys Thr Gly Ala Ala Thr Gly Cys Thr Gly Ala  Cys Ala Ala Cys
        2765                2770                2775
Ala Gly Gly Ala Cys Cys Thr Gly Cys Ala Gly  Thr Gly Cys Thr
        2780                2785                2790
Cys Cys Cys Ala Gly Cys Ala Cys Cys Thr Thr  Cys Cys Thr Gly
        2795                2800                2805
Cys Thr Cys Thr Thr Cys Ala Gly Thr Cys Ala  Gly Ala Ala Gly
        2810                2815                2820
Ala Gly Cys Gly Cys Cys Ala Thr Cys Ala Ala  Cys Cys Gly Cys
        2825                2830                2835
Ala Thr Gly Gly Thr Gly Ala Thr Thr Gly Ala  Thr Gly Ala Ala
        2840                2845                2850
Cys Ala Ala Cys Ala Gly Ala Gly Cys Cys Thr  Gly Ala Cys
        2855                2860                2865
Ala Thr Cys Ala Thr Cys Cys Thr Thr Cys Thr  Ala Thr Cys
        2870                2875                2880
Cys Ala Cys Ala Gly Cys Cys Thr Thr Cys Gly  Gly Ala Ala Cys
        2885                2890                2895
```

-continued

Gly Thr Cys Cys Gly Gly Gly Cys Cys Ala Thr Thr Gly Ala Cys
    2900                2905                2910

Thr Ala Thr Gly Ala Cys Cys Thr Thr Gly Gly Ala Cys
    2915                2920                2925

Ala Ala Gly Cys Ala Gly Cys Thr Cys Thr Ala Cys Thr Gly Gly
    2930                2935                2940

Ala Thr Thr Gly Ala Cys Thr Cys Thr Cys Gly Ala Cys Ala Ala
    2945                2950                2955

Ala Ala Cys Thr Cys Cys Ala Thr Ala Cys Gly Ala Ala Ala Gly
    2960                2965                2970

Gly Cys Ala Cys Ala Thr Gly Ala Ala Gly Ala Thr Gly Gly Thr
    2975                2980                2985

Gly Gly Cys Cys Ala Gly Gly Gly Thr Thr Thr Thr Ala Ala Thr
    2990                2995                3000

Gly Thr Ala Gly Thr Thr Gly Cys Ala Ala Ala Cys Thr Cys Gly
    3005                3010                3015

Gly Thr Cys Gly Cys Ala Ala Ala Thr Cys Ala Gly Ala Ala Cys
    3020                3025                3030

Cys Thr Thr Gly Ala Ala Ala Thr Ala Cys Ala Gly Cys Cys Cys
    3035                3040                3045

Thr Ala Thr Gly Ala Thr Cys Thr Cys Ala Gly Cys Ala Thr Thr
    3050                3055                3060

Gly Ala Thr Ala Thr Thr Thr Ala Thr Ala Gly Cys Cys Gly Thr
    3065                3070                3075

Thr Ala Cys Ala Thr Cys Thr Ala Cys Thr Gly Gly Ala Cys Cys
    3080                3085                3090

Thr Gly Thr Gly Ala Ala Gly Cys Thr Ala Cys Cys Ala Ala Thr
    3095                3100                3105

Gly Thr Cys Ala Thr Thr Gly Ala Thr Gly Thr Gly Ala Cys Gly
    3110                3115                3120

Ala Gly Ala Thr Thr Ala Gly Ala Thr Gly Gly Ala Cys Gly Ala
    3125                3130                3135

Thr Cys Ala Gly Thr Thr Gly Gly Ala Gly Thr Gly Gly Thr Thr
    3140                3145                3150

Cys Thr Ala Ala Ala Ala Gly Gly Cys Gly Ala Gly Cys Ala Ala
    3155                3160                3165

Gly Ala Cys Ala Gly Ala Cys Cys Thr Cys Gly Ala Gly Cys Cys
    3170                3175                3180

Ala Thr Thr Gly Thr Gly Gly Thr Ala Ala Ala Cys Cys Cys Cys
    3185                3190                3195

Gly Ala Gly Ala Ala Ala Gly Gly Gly Thr Ala Thr Ala Thr Gly
    3200                3205                3210

Thr Ala Thr Thr Thr Thr Ala Cys Cys Ala Ala Thr Cys Thr Thr
    3215                3220                3225

Cys Ala Gly Gly Ala Ala Ala Gly Ala Thr Cys Thr Cys Cys Thr
    3230                3235                3240

Ala Ala Ala Ala Thr Thr Gly Ala Ala Cys Gly Gly Gly Cys Thr
    3245                3250                3255

Gly Cys Ala Thr Thr Gly Gly Ala Thr Gly Gly Thr Ala Cys Ala
    3260                3265                3270

Gly Ala Ala Cys Gly Ala Gly Ala Gly Gly Thr Cys Cys Thr Cys
    3275                3280                3285

-continued

Thr Thr Thr Thr Thr Cys Ala Gly Thr Gly Cys Thr Thr Ala
3290             3295             3300

Ala Gly Thr Ala Ala Ala Cys Cys Ala Ala Thr Gly Cys Thr
3305             3310             3315

Thr Thr Gly Gly Cys Thr Cys Thr Thr Gly Ala Thr Ala Gly Cys
3320             3325             3330

Ala Ala Gly Cys Thr Gly Gly Gly Cys Ala Ala Gly Cys Thr Cys
3335             3340             3345

Thr Thr Cys Thr Gly Gly Gly Cys Thr Gly Ala Cys Thr Cys Ala
3350             3355             3360

Gly Ala Thr Cys Thr Cys Cys Gly Gly Cys Gly Ala Ala Thr Thr
3365             3370             3375

Gly Ala Ala Ala Gly Cys Ala Gly Thr Gly Ala Thr Cys Thr Cys
3380             3385             3390

Thr Cys Ala Gly Gly Thr Gly Cys Cys Ala Ala Cys Ala Gly Gly
3395             3400             3405

Ala Thr Cys Gly Thr Gly Cys Thr Ala Gly Ala Ala Gly Ala Cys
3410             3415             3420

Thr Cys Thr Ala Ala Thr Ala Thr Ala Thr Thr Ala Cys Ala Gly
3425             3430             3435

Cys Cys Thr Gly Thr Gly Gly Gly Cys Cys Thr Gly Ala Cys Cys
3440             3445             3450

Gly Thr Gly Thr Thr Thr Gly Ala Ala Ala Ala Cys Thr Gly Gly
3455             3460             3465

Cys Thr Cys Thr Ala Thr Thr Gly Gly Ala Thr Thr Gly Ala Thr
3470             3475             3480

Ala Ala Ala Cys Ala Gly Cys Ala Gly Cys Ala Gly Ala Thr Gly
3485             3490             3495

Ala Thr Thr Gly Ala Ala Ala Ala Ala Thr Thr Gly Ala Cys
3500             3505             3510

Ala Thr Gly Ala Cys Thr Gly Gly Thr Cys Gly Ala Gly Ala Ala
3515             3520             3525

Gly Gly Ala Ala Gly Ala Ala Cys Cys Ala Ala Gly Gly Thr Cys
3530             3535             3540

Cys Ala Gly Gly Cys Thr Cys Gly Ala Ala Thr Thr Gly Cys Thr
3545             3550             3555

Cys Ala Gly Cys Thr Gly Ala Gly Thr Gly Ala Cys Ala Thr Cys
3560             3565             3570

Cys Ala Thr Gly Cys Ala Gly Thr Ala Ala Gly Gly Ala Gly Gly
3575             3580             3585

Cys Thr Gly Ala Ala Cys Cys Thr Thr Cys Ala Gly Gly Ala Gly
3590             3595             3600

Thr Ala Cys Ala Gly Ala Cys Ala Gly Cys Ala Cys Cys Cys Thr
3605             3610             3615

Thr Gly Thr Gly Cys Cys Cys Ala Gly Gly Ala Thr Ala Ala Thr
3620             3625             3630

Gly Gly Thr Gly Gly Cys Thr Gly Thr Thr Cys Ala Cys Ala Thr
3635             3640             3645

Ala Thr Cys Thr Gly Cys Cys Thr Thr Gly Thr Ala Ala Ala Ala
3650             3655             3660

Gly Gly Ala Gly Ala Thr Gly Gly Thr Ala Cys Gly Ala Cys Ala
3665             3670             3675

Ala Gly Ala Thr Gly Cys Thr Cys Cys Thr Gly Cys Cys Cys Cys

-continued

```
                3680                3685                3690
Ala Thr  Gly Cys Ala Cys Thr  Thr Ala Gly Thr  Thr Cys Thr Gly
        3695                3700                3705
Cys Thr  Thr Cys Ala Gly Gly  Ala Thr Gly Ala  Gly Cys Thr Gly
        3710                3715                3720
Thr Cys  Cys Thr Gly Thr Gly  Gly Ala Gly Ala  Gly Cys Cys Thr
        3725                3730                3735
Cys Cys  Ala Ala Cys Gly Thr  Gly Thr Thr Cys  Thr Cys Cys Thr
        3740                3745                3750
Cys Ala  Gly Cys Ala Gly Thr  Thr Thr Ala Cys  Cys Thr Gly Cys
        3755                3760                3765
Thr Thr  Cys Ala Cys Thr Gly  Gly Gly Gly Ala  Cys Ala Thr Thr
        3770                3775                3780
Gly Ala  Cys Thr Gly Cys Ala  Thr Cys Cys Thr  Cys Gly Thr Gly
        3785                3790                3795
Gly Cys  Thr Thr Gly Gly Cys  Gly Gly Thr Gly  Thr Gly Ala Thr
        3800                3805                3810
Gly Gly  Gly Thr Thr Cys Ala  Cys Thr Gly Ala  Gly Thr Gly Cys
        3815                3820                3825
Gly Ala  Ala Gly Ala Cys Cys  Ala Cys Ala Gly  Cys Gly Ala Thr
        3830                3835                3840
Gly Ala  Ala Cys Thr Cys Ala  Ala Thr Gly Thr  Cys Thr Cys Cys
        3845                3850                3855
Gly Thr  Gly Thr Gly Cys Thr  Cys Ala Gly Ala  Gly Thr Cys Thr
        3860                3865                3870
Cys Ala  Gly Thr Thr Cys Cys  Ala Gly Thr Gly  Thr Gly Cys Cys
        3875                3880                3885
Ala Gly  Cys Gly Gly Gly Cys  Ala Gly Thr Gly  Cys Ala Thr Thr
        3890                3895                3900
Gly Ala  Thr Gly Gly Thr Gly  Cys Cys Cys Thr  Thr Cys Gly Ala
        3905                3910                3915
Thr Gly  Cys Ala Ala Thr Gly  Gly Cys Gly Ala  Thr Gly Cys Gly
        3920                3925                3930
Ala Ala  Cys Thr Gly Cys Cys  Ala Gly Gly Ala  Cys Ala Ala Ala
        3935                3940                3945
Thr Cys  Ala Gly Ala Thr Gly  Ala Gly Ala Ala  Gly Ala Ala Cys
        3950                3955                3960
Thr Gly  Thr Gly Ala Ala Gly  Thr Gly Cys Thr  Thr Gly Thr Thr
        3965                3970                3975
Thr Thr  Ala Ala Thr Thr Gly  Ala Thr Cys Ala  Gly Thr Thr Cys
        3980                3985                3990
Cys Gly  Cys Thr Gly Thr Gly  Cys Cys Ala Ala  Thr Gly Gly Thr
        3995                4000                4005
Cys Ala  Gly Thr Gly Cys Gly  Thr Thr Gly Gly  Ala Ala Ala Gly
        4010                4015                4020
Cys Ala  Cys Ala Ala Gly Ala  Ala Ala Thr Gly  Thr Gly Ala Cys
        4025                4030                4035
Cys Ala  Cys Ala Gly Thr Gly  Thr Gly Gly Ala  Cys Thr Gly Cys
        4040                4045                4050
Ala Gly  Thr Gly Ala Cys Ala  Gly Ala Thr Cys  Thr Gly Ala Cys
        4055                4060                4065
Gly Ala  Gly Cys Thr Gly Gly  Ala Cys Thr Gly  Thr Thr Ala Thr
        4070                4075                4080
```

-continued

```
Cys Cys Ala Ala Cys Thr Gly Ala Gly Ala Gly Cys Cys Ala
    4085                4090                4095
Gly Cys Ala Cys Cys Ala Cys Ala Ala Gly Cys Cys Ala Cys Cys
    4100                4105                4110
Ala Ala Cys Ala Cys Ala Gly Thr Thr Gly Gly Thr Thr Cys Cys
    4115                4120                4125
Gly Thr Thr Ala Thr Thr Gly Gly Ala Gly Thr Ala Ala Thr Thr
    4130                4135                4140
Gly Thr Cys Ala Cys Cys Ala Thr Thr Thr Thr Gly Thr Gly
    4145                4150                4155
Thr Cys Thr Gly Gly Ala Ala Cys Cys Ala Thr Ala Thr Ala Cys
    4160                4165                4170
Thr Thr Thr Ala Thr Cys Thr Gly Cys Cys Ala Gly Ala Gly Gly
    4175                4180                4185
Ala Thr Gly Cys Thr Gly Thr Gly Thr Cys Cys Thr Cys Gly Thr
    4190                4195                4200
Ala Thr Gly Ala Ala Gly Gly Ala Gly Ala Cys Gly Gly Gly
    4205                4210                4215
Gly Ala Gly Ala Cys Cys Ala Thr Gly Ala Cys Thr Ala Ala Cys
    4220                4225                4230
Gly Ala Cys Thr Ala Thr Gly Thr Gly Thr Thr Cys Ala Cys
    4235                4240                4245
Ala Gly Cys Cys Cys Gly Gly Cys Gly Thr Cys Thr Gly Thr Gly
    4250                4255                4260
Cys Cys Cys Cys Thr Thr Gly Thr Thr Ala Thr Gly Thr Thr
    4265                4270                4275
Cys Cys Thr Cys Ala Cys Cys Cys Ala Ala Gly Cys Thr Cys Thr
    4280                4285                4290
Cys Thr Cys Thr Cys Thr Gly Gly Ala Thr Cys Thr Cys Thr Thr
    4295                4300                4305
Cys Cys Ala Gly Gly Ala Ala Thr Gly Thr Cys Thr Cys Gly Ala
    4310                4315                4320
Gly Gly Cys Ala Ala Ala Thr Cys Ala Ala Thr Gly Ala Thr Cys
    4325                4330                4335
Ala Gly Thr Thr Cys Cys Cys Thr Cys Ala Gly Thr Ala Thr Cys
    4340                4345                4350
Ala Thr Gly Gly Gly Gly Gly Ala Ala Gly Cys Ala Gly Thr
    4355                4360                4365
Gly Gly Gly Cys Cys Cys Cys Cys Thr Ala Thr Gly Ala Thr
    4370                4375                4380
Cys Gly Ala Gly Cys Gly Cys Ala Cys Gly Thr Cys Ala Cys Gly
    4385                4390                4395
Gly Gly Ala Gly Cys Cys Thr Cys Cys Thr Cys Ala Ala Gly Cys
    4400                4405                4410
Ala Gly Thr Thr Cys Thr Thr Cys Cys Ala Gly Thr Ala Cys Cys
    4415                4420                4425
Ala Ala Ala Gly Gly Cys Ala Cys Thr Thr Ala Thr Thr Thr Cys
    4430                4435                4440
Cys Cys Thr Gly Cys Ala Ala Thr Thr Thr Thr Gly Ala Ala Cys
    4445                4450                4455
Cys Cys Ala Cys Cys Ala Cys Cys Ala Thr Cys Cys Cys Cys Thr
    4460                4465                4470
```

```
Gly Cys Cys Ala Cys Ala Gly Ala Ala Gly Ala     Thr Cys Cys
    4475            4480            4485
Cys Ala Thr Thr Ala Thr Ala Cys Cys Ala Thr Gly Gly Ala Ala
    4490            4495            4500
Thr Thr Thr Gly Gly Thr Thr Ala Thr Cys Thr     Thr Cys Cys
    4505            4510            4515
Ala Ala Cys Ala Gly Thr Cys Cys Thr Thr Cys Cys Ala Cys Ala
    4520            4525            4530
Cys Ala Thr Ala Gly Gly Thr Cys Cys Thr Ala Cys Ala Gly Cys
    4535            4540            4545
Thr Ala Thr Ala Gly Gly Cys Cys Gly Thr Ala Cys Ala Gly Cys
    4550            4555            4560
Thr Ala Cys Cys Gly Gly Cys Ala Cys Thr Thr Gly Gly Cys Ala
    4565            4570            4575
Cys Cys Gly Cys Cys Ala Cys Cys Ala Cys Ala Cys Cys Cys
    4580            4585            4590
Thr Gly Cys Ala Gly Cys Ala Cys Thr Gly Ala Thr Gly Thr Cys
    4595            4600            4605
Thr Gly Thr Gly Ala Cys Ala Gly Thr Gly Ala Cys Thr Ala Thr
    4610            4615            4620
Gly Cys Thr Cys Cys Thr Ala Gly Cys Cys Gly Gly Ala Gly Gly
    4625            4630            4635
Ala Thr Gly Ala Cys Cys Thr Cys Gly Gly Thr Gly Gly Cys Ala
    4640            4645            4650
Ala Cys Ala Gly Cys Cys Ala Ala Gly Gly Gly Cys Thr Ala Cys
    4655            4660            4665
Ala Cys Cys Ala Gly Thr Gly Ala Cys Gly Thr Gly Ala Ala Cys
    4670            4675            4680
Thr Ala Thr Gly Ala Cys Thr Cys Ala Gly Ala Ala Cys Cys Thr
    4685            4690            4695
Gly Thr Gly Cys Cys Cys Cys Ala Cys Cys Gly Cys Cys Cys
    4700            4705            4710
Ala Cys Ala Cys Cys Cys Cys Gly Ala Ala Gly Cys Cys Ala Gly
    4715            4720            4725
Thr Ala Cys Thr Thr Gly Thr Cys Ala Gly Cys Gly Gly Ala Gly
    4730            4735            4740
Gly Ala Gly Ala Ala Cys Thr Ala Thr Gly Ala Ala Ala Gly Cys
    4745            4750            4755
Thr Gly Cys Cys Cys Cys Cys Thr Thr Cys Cys Cys Cys Ala
    4760            4765            4770
Thr Ala Cys Ala Cys Gly Gly Ala Gly Ala Gly Ala Gly Thr
    4775            4780            4785
Thr Ala Cys Thr Cys Cys Ala Cys Cys Ala Cys Cys Thr Cys
    4790            4795            4800
Thr Ala Cys Cys Cys Gly Cys Ala Cys Cys Ala Cys Cys Cys
    4805            4810            4815
Thr Cys Cys Cys Cys Thr Gly Cys Ala Cys Gly Gly Ala Cys
    4820            4825            4830
Thr Cys Cys Thr Cys Cys Thr Gly Ala
    4835            4840

<210> SEQ ID NO 9
<211> LENGTH: 4842
<212> TYPE: DNA
```

<213> ORGANISM: Mouse

<400> SEQUENCE: 9

| | | | | | |
|---|---|---|---|---|---|
| atggggccg | tgctgaggag | cctcctggcc | tgcagcttct | gcgtgctgct | gagagcggcc | 60 |
| cctttgttgc | tttatgcaaa | cagacgggac | ttgagattgg | ttgatgctac | aaatggcaaa | 120 |
| gagaatgcaa | cgattgtagt | tggaggcttg | gaggatgcag | ctgcggtgga | ctttgtgttt | 180 |
| ggtcatggct | tgatatactg | gagtgatgtc | agcgaagaag | ccattaaacg | aacagaattt | 240 |
| aacaaaagtg | aaagtgtaca | gaatgttgtt | gtttctggat | tatttgtccc | ggatgggctg | 300 |
| gcatgtgatt | ggcttggaga | aaaattgtac | tggacagatt | ctgaaactaa | tcgtattgaa | 360 |
| gtttctaatt | tagatggatc | tttacgaaaa | gttttatttt | ggcaagagtt | ggatcaaccc | 420 |
| agagctattg | ccttagatcc | atcaagtggg | ttcatgtact | ggacagactg | gggagaagtg | 480 |
| ccaaagatag | aacgggctgg | gatggatggc | tcaagtcgct | tcgttataat | aaacacggag | 540 |
| atttactggc | aaacggact | gactctggat | tatcaggagc | ggaagcttta | ctgggccgat | 600 |
| gcaaaactta | atttcatcca | taaatcaaac | ctggatggaa | caaaccggca | ggcagtggtt | 660 |
| aaaggttccc | ttccacatcc | ttttgccttg | acgttatttg | aggacacatt | gtactggact | 720 |
| gactggaata | cacactctat | tttggcttgc | aacaaatata | ctggcgaggg | tctgcgtgaa | 780 |
| attcattcta | acatcttctc | tcccatggat | atacatgctt | tcagccaaca | gaggcagcca | 840 |
| aatgctacaa | atccatgtgg | aattgataat | ggtggttgtt | cccatttgtg | tttgatgtct | 900 |
| ccagtcaagc | cttttttatca | gtgtgcttgc | ccaactgggg | tcaagctgat | ggagaatgga | 960 |
| aagacctgca | aagatggtgc | cactgaacta | ttgctgttag | cccgacggac | agacttgagg | 1020 |
| cgaatttctt | tggatacacc | cgatttttact | gacattgttc | tgcagttaga | agatatccgg | 1080 |
| catgccattg | ccatagacta | tgaccctgta | gaaggctaca | tatactggac | agatgacgaa | 1140 |
| gtgagggcta | tccgtcgctc | cttcatagat | ggatctggca | gtcagtttgt | ggtcacggcc | 1200 |
| cagattgctc | atcctgatgg | tattgctgtt | gactgggttg | caaggaacct | gtactggaca | 1260 |
| gacactggca | cggatcgtat | agaagtgaca | aggctcaatg | gaccatgag | gaagatcttg | 1320 |
| atttcagagg | acttagagga | gccccgggct | atcgtgttag | atcccatggt | tgggtacatg | 1380 |
| tattggacag | actggggaga | aatcccaaaa | atagagcgag | ctgctctgga | cggatctgac | 1440 |
| cgagtagttc | ttgtcaacac | ttcccttggt | tggccaaacg | gcttagccct | ggattatgat | 1500 |
| gaaggcacaa | tatactgggg | agatgccaaa | acagacaaaa | ttgaggttat | gaataccgat | 1560 |
| ggcaccggga | ggcgagtgct | ggtggaagac | aagatccctc | acatatttgg | gtttaccttg | 1620 |
| ctgggtgact | atgtttactg | gactgactgg | cagaggcgga | gcatcgagag | agtacacaaa | 1680 |
| cggagcgcag | agagggaagt | catcatagac | cagctgccag | acctcatggg | actgaaggcc | 1740 |
| acaagtgttc | acagagtcat | tggttctaac | ccctgtgctg | aggacaatgg | aggatgtagc | 1800 |
| catctttgcc | tgtacaggcc | tcaggggctt | cgatgcgcct | gtcccattgg | ctttgagctc | 1860 |
| atcggtgaca | tgaagacatg | cattgtcccc | gaggctttcc | ttctgttctc | gaggagagcg | 1920 |
| gatatcagac | gcatatcttt | ggaaacaaac | aacaacaatg | tggccattcc | tctcactggt | 1980 |
| gtcaaagaag | cctctgcttt | ggattttgat | gtcacagaca | acaggattta | ctggactgat | 2040 |
| atatcactga | agactattag | cagagccttt | atgaatggca | gtgcactgga | acatgtggta | 2100 |
| gagtttggct | tagattatcc | agaaggcatg | gcagtggact | ggcttgggaa | gaacttatac | 2160 |
| tgggcagaca | caggaacaaa | tcgcattgag | gtatcaaagt | tggacggaca | gcaccgacag | 2220 |
| gttttggtat | ggaaagacct | tgacagtcct | cgagctctgg | cactggatcc | tgctgaaggg | 2280 |

-continued

```
tttatgtatt ggactgagtg gggaggcaag cctaagattg acagggctgc tatggatgga    2340
agtgaacgca ctacattagt tccaaatgta ggccgagcaa atggtctcac catcgactat    2400
gctaaaaggc ggctttactg gacagacctg gacactaacc taatagaatc ctcagatatg    2460
ctcggactca accgtgaagt tatagcagat gacttgcctc atccttttgg cttaactcag    2520
taccaagatt acatctactg gacagactgg agccgacgca gcattgaacg tgccaacaaa    2580
accagtggcc aaaaccgcac catcatccag ggccatttgg actatgtgat ggacatcctg    2640
gtcttccact cttcccggca ggcagggtgg aatgagtgtg cctccagcaa cgggcactgc    2700
tcccacctct gcttggctgt gcccgtcgga ggttttgtgt gtggatgccc tgcccactac    2760
tccctgaatg ctgacaacag gacctgcagt gctcccagca ccttcctgct cttcagtcag    2820
aagagcgcca tcaaccgcat ggtgattgat gaacaacaga gccctgacat catccttcct    2880
atccacagcc ttcggaacgt ccgggccatt gactatgacc cttggacaa gcagctctac    2940
tggattgact ctcgacaaaa ctccatacga aaggcacatg aagatggtgg ccagggtttt    3000
aatgtagttg caaactcggt cgcaaatcag aaccttgaaa tacagcccta tgatctcagc    3060
attgatattt atagccgtta catctactgg acctgtgaag ctaccaatgt cattgatgtg    3120
acgagattag atggacgatc agttggagtg gttctaaaag gcgagcaaga cagacctcga    3180
gccattgtgg taaaccccga gaagggtat atgtatttta ccaatcttca ggaaagatct    3240
cctaaaattg aacgggctgc attggatggt acagaacgag aggtcctctt tttcagtggc    3300
ttaagtaaac caattgcttt ggctcttgat agcaagctgg gcaagctctt ctgggctgac    3360
tcagatctcc ggcgaattga aagcagtgat ctctcaggtg ccaacaggat cgtgctagaa    3420
gactctaata tattacagcc tgtgggcctg accgtgtttg aaaactggct ctattggatt    3480
gataaacagc agcagatgat tgaaaaaatt gacatgactg tcgagaagg aagaaccaag    3540
gtccaggctc gaattgctca gctgagtgac atccatgcag taaaggagct gaaccttcag    3600
gagtacagac agcacccttg tgcccaggat aatggtggct gttcacatat ctgccttgta    3660
aaaggagatg gtacgacaag atgctcctgc cccatgcact tagttctgct tcaggatgag    3720
ctgtcctgtg gagagcctcc aacgtgttct cctcagcagt ttacctgctt cactggggac    3780
attgactgca tccctgtggc ttggcggtgt gatgggttca ctgagtgcga agaccacagc    3840
gatgaactca attgtcccgt gtgctcagag tctcagttcc agtgtgccag cgggcagtgc    3900
attgatggtg cccttcgatg caatggcgat gcgaactgcc aggacaaatc agatgagaag    3960
aactgtgaag tgctttgttt aattgatcag ttccgctgtg ccaatggtca gtgcgttgga    4020
aagcacaaga atgtgaccca cagtgtggac tgcagtgaca gatctgacga gctgactgt    4080
tatccaactg aggagccagc accacaagcc accaacacag ttggttccgt tattggagta    4140
attgtcacca tttttgtgtc tggaaccata tactttatct gccagaggat gctgtgtcct    4200
cgtatgaagg gagacgggga gaccatgact aacgactatg tggttcacag cccggcgtct    4260
gtgcccttg gttatgttcc tcacccaagc tctctctctg gatctcttcc aggaatgtct    4320
cgaggcaaat caatgatcag ttccctcagt atcatggggg aagcagtgg gccccctat    4380
gatcgagcgc acgtcacggg agcctcctca agcagttctt ccagtaccaa aggcactat    4440
ttccctgcaa ttttgaaccc accaccatcc cctgccacag aaagatccca ttataccatg    4500
gaatttggtt attcttccaa cagtccttcc acacataggt cctacagcta taggccgtac    4560
agctaccggc actttgcacc gcccaccaca ccctgcagca ctgatgtctg tgacagtgac    4620
```

```
tatgctccta gccggaggat gacctcggtg gcaacagcca agggctacac cagtgacgtg      4680
aactatgact cagaacctgt gcccccaccg cccacaccc gaagccagta cttgtcagcg       4740
gaggagaact atgaaagctg cccccttcc ccatacacgg agaggagtta ctcccaccac       4800
ctctacccgc caccccctc cccctgcacg gactcctcct ga                          4842
```

<210> SEQ ID NO 10
<211> LENGTH: 1613
<212> TYPE: PRT
<213> ORGANISM: Mouse

<400> SEQUENCE: 10

```
Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Gly His Gly Leu
        50                  55                  60

Ile Tyr Trp Ser Asp Val Ser Glu Glu Ala Ile Lys Arg Thr Glu Phe
65              70                  75                  80

Asn Lys Ser Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
                100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145             150                 155                 160

Pro Lys Ile Glu Arg Ala Gly Met Asp Gly Ser Ser Arg Phe Val Ile
                165                 170                 175

Ile Asn Thr Glu Ile Tyr Trp Pro Asn Gly Leu Thr Leu Asp Tyr Gln
            180                 185                 190

Glu Arg Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Thr Leu Tyr Trp Thr
225             230                 235                 240

Asp Trp Asn Thr His Ser Ile Leu Ala Cys Asn Lys Tyr Thr Gly Glu
                245                 250                 255

Gly Leu Arg Glu Ile His Ser Asn Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Met Glu Asn Gly
305             310                 315                 320

Lys Thr Cys Lys Asp Gly Ala Thr Glu Leu Leu Leu Leu Ala Arg Arg
                325                 330                 335
```

```
Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
                420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Thr Ile Tyr Trp Gly Asp Ala Lys Thr Asp
                500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Ser Val His Arg Val Ile Gly Ser Asn Pro Cys
                580                 585                 590

Ala Glu Asp Asn Gly Gly Cys Ser His Leu Cys Leu Tyr Arg Pro Gln
            595                 600                 605

Gly Leu Arg Cys Ala Cys Pro Ile Gly Phe Glu Leu Ile Gly Asp Met
    610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
            690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
```

-continued

```
                755                 760                 765
Gly Lys Pro Lys Ile Asp Arg Ala Ala Met Asp Gly Ser Glu Arg Thr
    770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asp Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
    850                 855                 860
Asn Arg Thr Ile Ile Gln Gly His Leu Asp Tyr Val Met Asp Ile Leu
865                 870                 875                 880
Val Phe His Ser Ser Arg Gln Ala Gly Trp Asn Glu Cys Ala Ser Ser
                885                 890                 895
Asn Gly His Cys Ser His Leu Cys Leu Ala Val Pro Val Gly Gly Phe
            900                 905                 910
Val Cys Gly Cys Pro Ala His Tyr Ser Leu Asn Ala Asp Asn Arg Thr
        915                 920                 925
Cys Ser Ala Pro Ser Thr Phe Leu Leu Phe Ser Gln Lys Ser Ala Ile
    930                 935                 940
Asn Arg Met Val Ile Asp Glu Gln Gln Ser Pro Asp Ile Ile Leu Pro
945                 950                 955                 960
Ile His Ser Leu Arg Asn Val Arg Ala Ile Asp Tyr Asp Pro Leu Asp
                965                 970                 975
Lys Gln Leu Tyr Trp Ile Asp Ser Arg Gln Asn Ser Ile Arg Lys Ala
            980                 985                 990
His Glu Asp Gly Gly Gln Gly Phe Asn Val Val Ala Asn Ser Val Ala
        995                 1000                1005
Asn Gln Asn Leu Glu Ile Gln Pro Tyr Asp Leu Ser Ile Asp Ile
    1010                1015                1020
Tyr Ser Arg Tyr Ile Tyr Trp Thr Cys Glu Ala Thr Asn Val Ile
    1025                1030                1035
Asp Val Thr Arg Leu Asp Gly Arg Ser Val Gly Val Val Leu Lys
    1040                1045                1050
Gly Glu Gln Asp Arg Pro Arg Ala Ile Val Val Asn Pro Glu Lys
    1055                1060                1065
Gly Tyr Met Tyr Phe Thr Asn Leu Gln Glu Arg Ser Pro Lys Ile
    1070                1075                1080
Glu Arg Ala Ala Leu Asp Gly Thr Glu Arg Glu Val Leu Phe Phe
    1085                1090                1095
Ser Gly Leu Ser Lys Pro Ile Ala Leu Ala Leu Asp Ser Lys Leu
    1100                1105                1110
Gly Lys Leu Phe Trp Ala Asp Ser Asp Leu Arg Arg Ile Glu Ser
    1115                1120                1125
Ser Asp Leu Ser Gly Ala Asn Arg Ile Val Leu Glu Asp Ser Asn
    1130                1135                1140
Ile Leu Gln Pro Val Gly Leu Thr Val Phe Glu Asn Trp Leu Tyr
    1145                1150                1155
Trp Ile Asp Lys Gln Gln Gln Met Ile Glu Lys Ile Asp Met Thr
    1160                1165                1170
```

-continued

```
Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Asp Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Val Gly Lys His Lys Lys Cys Asp His Ser Val Asp Cys Ser Asp
    1340                1345                1350

Arg Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Ile Tyr Phe Ile Cys Gln Arg Met Leu
    1385                1390                1395

Cys Pro Arg Met Lys Gly Asp Gly Glu Thr Met Thr Asn Asp Tyr
    1400                1405                1410

Val Val His Ser Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Val Asn Tyr Asp
    1550                1555                1560
```

```
Ser Glu Pro Val Pro Pro Pro Thr Pro Arg Ser Gln Tyr Leu
    1565            1570            1575

Ser Ala Glu Glu Asn Tyr Glu Ser Cys Pro Ser Pro Tyr Thr
    1580            1585            1590

Glu Arg Ser Tyr Ser His His Leu Tyr Pro Pro Pro Ser Pro
    1595            1600            1605

Cys Thr Asp Ser Ser
    1610

<210> SEQ ID NO 11
<211> LENGTH: 4161
<212> TYPE: DNA
<213> ORGANISM: Mouse

<400> SEQUENCE: 11
atggaaacgg cgccgacccg ggcccctccg ccgccgccgc cgccgctgct gctgctggtg     60
ctgtactgca gcttggtccc cgccgcggcc tcaccgctcc tgttgtttgc aaccgccgg    120 gatgtgcggc tagtggatgc cggcggagtg aagctggagt ccaccattgt ggccagtggc    180
ctggaggatg cagctgctgt agacttccag ttctccaagg gtgctgtgta ctggacagat    240
gtgagcgagg aggccatcaa acagacctac ctgaaccaga ctggagctgc tgcacagaac    300
attgtcatct cggccctcgt gtcacctgat ggcctggcct gtgactgggt ggcaagaag    360 ctgtactgga cggactccga gaccaaccgc attgaggttg ccaacctcaa tgggacgtcc    420
cgtaaggttc tcttctggca ggacctggac cagccaaggg ccattgccct ggatcctgca    480
catgggtaca tgtactggac tgactggggg aagcacccc ggatcgagcg gcagggatg    540 gatggcagta cccggaagat cattgtagac tccgacattt actggcccaa tgggctgacc    600
atcgacctgg aggaacagaa gctgtactgg gccgatgcca agctcagctt catccaccgt    660
gccaacctgg acggtccctt ccggcagaag gtggtggagg cagcctcac tcacccttt    720 gccctgacac tctctgggga cacactctac tggacagact ggcagaccg ctccatccac    780 gcctgcaaca gtggacagg ggagcagagg aaggagatcc ttagtgctct gtactcaccc    840
atggacatcc aagtgctgag ccaggagcgg cagcctccct tccacacacc atgcgaggag    900
gacaacggtg ctgttcccca cctgtgcctg ctgtccccga gggagccttt ctactcctgt    960
gcctgcccca ctggtgtgca gttgcaggac aatggcaaga cgtgcaagac aggggctgag   1020
gaagtgctgc tgctggctcg gaggacagac ctgaggagga tctctctgga caccctgac   1080 ttcacagaca tagtgctgca ggtgggcgac atccggcatg ccattgccat tgactacgat   1140
cccctggagg gctacgtgta ctggaccgat gatgaggtgc gggctatccg cagggcgtac   1200
ctagatggct caggtgcgca gacacttgtg aacactgaga tcaatgaccc cgatggcatt   1260
gctgtggact gggtcgcccg gaacctctac tggacagata caggcactga cagaattgag   1320
gtgactcgcc tcaacggcac ctcccgaaag atcctggtat ctgaggacct ggacgaaccg   1380
cgagccattg tgttgcaccc tgtgatgggc ctcatgtact ggacagactg gggggagaac   1440
cccaaaatcg aatgcgccaa cctagatggg agagatcggc atgtcctggt gaacacctcc   1500
cttgggtggc ccaatggact ggccctggac ctgcaggagg gcaagctgta ctgggggat   1560 gccaaaactg ataaaatcga ggtgatcaac atagacggga caaagcggaa gaccctgctt   1620
gaggacaagc tcccacacat ttttgggttc acactgctgg gggacttcat ctactggacc   1680
gactggcaga gacgcagtat tgaaagggtc cacaaggtca aggccagccg ggatgtcatc   1740
attgatcaac tccccgacct gatgggactc aaagccgtga atgtggccaa ggttgtcgga   1800
```

```
accaacccat gtgcggatgg aaatggaggg tgcagccatc tgtgcttctt cacccacgt    1860
gccaccaagt gtggctgccc cattggcctg gagctgttga gtgacatgaa gacctgcata   1920
atccccgagg ccttcctggt attcaccagc agagccacca tccacaggat ctccctggag   1980
actaacaaca acgatgtggc tatcccactc acgggtgtca agaggcctc tgcactggac    2040
tttgatgtgt ccaacaatca catctactgg actgatgtta gcctcaagac gatcagccga   2100
gccttcatga atgggagctc agtggagcac gtgattgagt ttggcctcga ctaccctgaa   2160
ggaatggctg tggactggat gggcaagaac ctctattggg cggacacagg gaccaacagg   2220
attgaggtgg cccggctgga tgggcagttc cggcaggtgc ttgtgtggag agaccttgac   2280
aaccccaggt ctctggctct ggatcctact aaaggctaca tctactggac tgagtggggt   2340
ggcaagccaa ggattgtgcg ggccttcatg gatgggacca attgtatgac actggtagac   2400
aaggtgggcc gggccaacga cctcaccatt gattatgccg accagcgact gtactggact   2460
gacctggaca ccaacatgat tgagtcttcc aacatgctgg gtcaggagcg catggtgata   2520
gctgacgatc tgccctaccc gtttggcctg actcaatata gcgattacat ctactggact   2580
gactggaacc tgcatagcat tgaacgggcg acaagacca gtgggcggaa ccgcaccctc    2640
atccagggtc acctgacttt cgtcatggac atcctggtgt tccactcctc ccgtcaggat   2700
ggcctcaacg actgcgtgca cagcaatggc cagtgtgggc agctgtgcct cgccatcccc   2760
ggaggccacc gctgtggctg tgcttcacac tacacgctgg accccagcag ccgcaactgc   2820
agcccgccct ccaccttctt gctgttcagc cagaaatttg ccatcagccg gatgatcccc   2880
gatgaccagc tcagcccgga ccttgtccta ccccttcatg ggctgaggaa cgtcaaagcc   2940
atcaactatg acccgctgga caagttcatc tactgggtgg acgggcgcca gaacatcaag   3000
agggccaagg acgacggtac ccagccctcc atgctgacct ctcccagcca aagcctgagc   3060
ccagacagac agccacacga cctcagcatt gacatctaca gccggacact gttctggacc   3120
tgtgaggcca ccaacactat caatgtccac cggctggatg gggatgccat gggagtggtg   3180
cttgaggggg accgtgacaa gccaagggcc attgctgtca atgctgagcg agggtacatg   3240
tactttacca acatgcagga ccatgctgcc aagatcgagc gagcctccct ggatggcaca   3300
gagcgggagg tcctcttcac cacaggcctc atccgtcccg tggcccttgt ggtggacaat   3360
gctctgggca agctcttctg ggtggatgcc gacctaaagc gaatcgaaag ctgtgacctc   3420
tctggggcca accgcctgac cctggaagat gccaacatcg tacagccagt aggtctgaca   3480
gtgctgggca ggcacctcta ctggatcgac cgccagcagc agatgatcga gcgcgtggag   3540
aagaccactg gggacaagcg gactagggtt cagggccgtg tcacccacct gacaggcatc   3600
catgccgtgg aggaagtcag cctggaggag ttctcagccc atccttgtgc ccgagacaat   3660
ggcggctgct cccacatctg tatcgccaag ggtgatggaa caccgcgctg ctcgtgccct   3720
gtccacctgg tgctcctgca gaacctgctg acttgtggtg agcctcctac ctgctcccct   3780
gatcagtttg catgtaccac tggtgagatc gactgcatcc ccggagcctg cgctgtgac   3840
ggcttccctg agtgtgctga ccagagtgat gaagaaggct gcccagtgtg ctccgcctct   3900
cagttcccct gcgctcgagg ccagtgtgtg gacctgcgt tacgctgcga cggtgaggcc    3960
gactgccagg atcgctctga tgaagctaac tgcgatgctg tctgtctgcc caatcagttc   4020
cggtgcacca gcggccagtg tgtcctcatc aagcaacagt gtgactcctt ccccgactgt   4080
gctgatgggt ctgatgagct catgtgtgaa atcaacaagc caccctctga tgacatccca   4140
```
gcccacagca gtgccattgg g        4161

<210> SEQ ID NO 12
<211> LENGTH: 1384
<212> TYPE: PRT
<213> ORGANISM: Mouse

<400> SEQUENCE: 12

```
Met Glu Thr Ala Pro Thr Arg Ala Pro Pro Pro Pro Pro Pro Pro Leu
1               5                   10                  15

Leu Leu Leu Val Leu Tyr Cys Ser Leu Val Pro Ala Ala Ala Ser Pro
                20                  25                  30

Leu Leu Leu Phe Ala Asn Arg Arg Asp Val Arg Leu Val Asp Ala Gly
            35                  40                  45

Gly Val Lys Leu Glu Ser Thr Ile Val Ala Ser Gly Leu Glu Asp Ala
    50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                85                  90                  95

Ala Ala Gln Asn Ile Val Ile Ser Gly Leu Val Ser Pro Asp Gly Leu
                100                 105                 110

Ala Cys Asp Trp Val Gly Lys Lys Leu Tyr Trp Thr Asp Ser Glu Thr
            115                 120                 125

Asn Arg Ile Glu Val Ala Asn Leu Asn Gly Thr Ser Arg Lys Val Leu
    130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Glu Ala Pro Arg Ile Glu
                165                 170                 175

Arg Ala Gly Met Asp Gly Ser Thr Arg Lys Ile Ile Val Asp Ser Asp
                180                 185                 190

Ile Tyr Trp Pro Asn Gly Leu Thr Ile Asp Leu Glu Glu Gln Lys Leu
            195                 200                 205

Tyr Trp Ala Asp Ala Lys Leu Ser Phe Ile His Arg Ala Asn Leu Asp
    210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
                245                 250                 255

Arg Ser Ile His Ala Cys Asn Lys Trp Thr Gly Glu Gln Arg Lys Glu
                260                 265                 270

Ile Leu Ser Ala Leu Tyr Ser Pro Met Asp Ile Gln Val Leu Ser Gln
            275                 280                 285

Glu Arg Gln Pro Pro Phe His Thr Pro Cys Glu Glu Asp Asn Gly Gly
    290                 295                 300

Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                325                 330                 335

Thr Gly Ala Glu Glu Val Leu Leu Leu Ala Arg Arg Thr Asp Leu Arg
                340                 345                 350

Arg Ile Ser Leu Asp Thr Pro Asp Phe Thr Asp Ile Val Leu Gln Val
            355                 360                 365
```

-continued

```
Gly Asp Ile Arg His Ala Ile Ala Ile Asp Tyr Asp Pro Leu Glu Gly
    370                 375                 380

Tyr Val Tyr Trp Thr Asp Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
                405                 410                 415

Pro Asp Gly Ile Ala Val Asp Trp Val Ala Arg Asn Leu Tyr Trp Thr
            420                 425                 430

Asp Thr Gly Thr Asp Arg Ile Glu Val Thr Arg Leu Asn Gly Thr Ser
        435                 440                 445

Arg Lys Ile Leu Val Ser Glu Asp Leu Asp Glu Pro Arg Ala Ile Val
    450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                485                 490                 495

Val Asn Thr Ser Leu Gly Trp Pro Asn Gly Leu Ala Leu Asp Leu Gln
            500                 505                 510

Glu Gly Lys Leu Tyr Trp Gly Asp Ala Lys Thr Asp Lys Ile Glu Val
        515                 520                 525

Ile Asn Ile Asp Gly Thr Lys Arg Lys Thr Leu Leu Glu Asp Lys Leu
    530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590

Val Asn Val Ala Lys Val Val Gly Thr Asn Pro Cys Ala Asp Gly Asn
        595                 600                 605

Gly Gly Cys Ser His Leu Cys Phe Phe Thr Pro Arg Ala Thr Lys Cys
    610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
        675                 680                 685

Tyr Trp Thr Asp Val Ser Leu Lys Thr Ile Ser Arg Ala Phe Met Asn
    690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
            740                 745                 750

Val Leu Val Trp Arg Asp Leu Asp Asn Pro Arg Ser Leu Ala Leu Asp
        755                 760                 765

Pro Thr Lys Gly Tyr Ile Tyr Trp Thr Glu Trp Gly Gly Lys Pro Arg
    770                 775                 780

Ile Val Arg Ala Phe Met Asp Gly Thr Asn Cys Met Thr Leu Val Asp
```

-continued

```
            785                 790                 795                 800
Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
                820                 825                 830

Leu Gly Gln Glu Arg Met Val Ile Ala Asp Asp Leu Pro Tyr Pro Phe
                835                 840                 845

Gly Leu Thr Gln Tyr Ser Asp Tyr Ile Tyr Trp Thr Asp Trp Asn Leu
            850                 855                 860

His Ser Ile Glu Arg Ala Asp Lys Thr Ser Gly Arg Asn Arg Thr Leu
865                 870                 875                 880

Ile Gln Gly His Leu Asp Phe Val Met Asp Ile Leu Val Phe His Ser
                885                 890                 895

Ser Arg Gln Asp Gly Leu Asn Asp Cys Val His Ser Asn Gly Gln Cys
                900                 905                 910

Gly Gln Leu Cys Leu Ala Ile Pro Gly Gly His Arg Cys Gly Cys Ala
                915                 920                 925

Ser His Tyr Thr Leu Asp Pro Ser Ser Arg Asn Cys Ser Pro Pro Ser
            930                 935                 940

Thr Phe Leu Leu Phe Ser Gln Lys Phe Ala Ile Ser Arg Met Ile Pro
945                 950                 955                 960

Asp Asp Gln Leu Ser Pro Asp Leu Val Leu Pro Leu His Gly Leu Arg
                965                 970                 975

Asn Val Lys Ala Ile Asn Tyr Asp Pro Leu Asp Lys Phe Ile Tyr Trp
            980                 985                 990

Val Asp Gly Arg Gln Asn Ile Lys Arg Ala Lys Asp Asp Gly Thr Gln
            995                 1000                1005

Pro Ser Met Leu Thr Ser Pro Ser Gln Ser Leu Ser Pro Asp Arg
        1010                1015                1020

Gln Pro His Asp Leu Ser Ile Asp Ile Tyr Ser Arg Thr Leu Phe
        1025                1030                1035

Trp Thr Cys Glu Ala Thr Asn Thr Ile Asn Val His Arg Leu Asp
        1040                1045                1050

Gly Asp Ala Met Gly Val Val Leu Arg Gly Asp Arg Asp Lys Pro
        1055                1060                1065

Arg Ala Ile Ala Val Asn Ala Glu Arg Gly Tyr Met Tyr Phe Thr
        1070                1075                1080

Asn Met Gln Asp His Ala Ala Lys Ile Glu Arg Ala Ser Leu Asp
        1085                1090                1095

Gly Thr Glu Arg Glu Val Leu Phe Thr Thr Gly Leu Ile Arg Pro
        1100                1105                1110

Val Ala Leu Val Val Asp Asn Ala Leu Gly Lys Leu Phe Trp Val
        1115                1120                1125

Asp Ala Asp Leu Lys Arg Ile Glu Ser Cys Asp Leu Ser Gly Ala
        1130                1135                1140

Asn Arg Leu Thr Leu Glu Asp Ala Asn Ile Val Gln Pro Val Gly
        1145                1150                1155

Leu Thr Val Leu Gly Arg His Leu Tyr Trp Ile Asp Arg Gln Gln
        1160                1165                1170

Gln Met Ile Glu Arg Val Glu Lys Thr Thr Gly Asp Lys Arg Thr
        1175                1180                1185

Arg Val Gln Gly Arg Val Thr His Leu Thr Gly Ile His Ala Val
        1190                1195                1200
```

Glu Glu Val Ser Leu Glu Glu Phe Ser Ala His Pro Cys Ala Arg
    1205                1210                1215

Asp Asn Gly Gly Cys Ser His Ile Cys Ile Ala Lys Gly Asp Gly
    1220                1225                1230

Thr Pro Arg Cys Ser Cys Pro Val His Leu Val Leu Leu Gln Asn
    1235                1240                1245

Leu Leu Thr Cys Gly Glu Pro Pro Thr Cys Ser Pro Asp Gln Phe
    1250                1255                1260

Ala Cys Thr Thr Gly Glu Ile Asp Cys Ile Pro Gly Ala Trp Arg
    1265                1270                1275

Cys Asp Gly Phe Pro Glu Cys Ala Asp Gln Ser Asp Glu Glu Gly
    1280                1285                1290

Cys Pro Val Cys Ser Ala Ser Gln Phe Pro Cys Ala Arg Gly Gln
    1295                1300                1305

Cys Val Asp Leu Arg Leu Arg Cys Asp Gly Glu Ala Asp Cys Gln
    1310                1315                1320

Asp Arg Ser Asp Glu Ala Asn Cys Asp Ala Val Cys Leu Pro Asn
    1325                1330                1335

Gln Phe Arg Cys Thr Ser Gly Gln Cys Val Leu Ile Lys Gln Gln
    1340                1345                1350

Cys Asp Ser Phe Pro Asp Cys Ala Asp Gly Ser Asp Glu Leu Met
    1355                1360                1365

Cys Glu Ile Asn Lys Pro Pro Ser Asp Asp Ile Pro Ala His Ser
    1370                1375                1380

Ser

<210> SEQ ID NO 13
<211> LENGTH: 4845
<212> TYPE: DNA
<213> ORGANISM: Mouse

<400> SEQUENCE: 13

| | |
|---|---|
| atggaaacgg cgccgacccg ggcccctccg ccgccgccgc cgccgctgct gctgctggtg | 60 |
| ctgtactgca gcttggtccc cgccgcggcc tcaccgctcc tgttgtttgc caaccgccgg | 120 |
| gatgtgcggc tagtggatgc cggcggagtg aagctggagt ccaccattgt ggccagtggc | 180 |
| ctggaggatg cagctgctgt agacttccag ttctccaagg gtgctgtgta ctggacagat | 240 |
| gtgagcgagg aggccatcaa acagacctac ctgaaccaga ctggagctgc tgcacagaac | 300 |
| attgtcatct cgggcctcgt gtcacctgat ggcctggcct gtgactgggt tggcaagaag | 360 |
| ctgtactgga cggactccga gaccaaccgc attgaggttg ccaacctcaa tgggacgtcc | 420 |
| cgtaaggttc tcttctggca ggacctggac cagccaaggg ccattgccct ggatcctgca | 480 |
| catgggtaca tgtactggac tgactggggg gaagcacccc ggatcgagcg ggcagggatg | 540 |
| gatggcagta cccggaagat cattgtagac tccgacattt actggcccaa tgggctgacc | 600 |
| atcgacctgg aggaacagaa gctgtactgg gccgatgcca agctcagctt catccaccgt | 660 |
| gccaacctgg acggctcctt ccggcagaag gtggtggagg cagcctcac tcacccttt | 720 |
| gccctgacac tctctgggga cactctctac tggacagact ggcagacccg ctccatccac | 780 |
| gcctgcaaca gtggacaggg gagcagagg aaggagatcc ttagtgctct gtactcaccc | 840 |
| atggacatcc aagtgctgag ccaggagcgg cagcctccct ccacacacc atgcgaggag | 900 |
| gacaacggtg gctgttccca cctgtgcctg ctgtccccga gggagccttt ctactcctgt | 960 |

```
gcctgcccca ctggtgtgca gttgcaggac aatggcaaga cgtgcaagac aggggctgag   1020
gaagtgctgc tgctggctcg gaggacagac ctgaggagga tctctctgga cacccctgac   1080
ttcacagaca tagtgctgca ggtgggcgac atccggcatg ccattgccat tgactacgat   1140
cccctggagg gctacgtgta ctggaccgat gatgaggtgc gggctatccg cagggcgtac   1200
ctagatggct caggtgcgca gacacttgtg aacactgaga tcaatgaccc cgatggcatt   1260
gctgtggact gggtcgcccg gaacctctac tggacagata caggcactga cagaattgag   1320
gtgactcgcc tcaacggcac ctcccgaaag atcctggtat ctgaggacct ggacgaaccg   1380
cgagccattg tgttgcaccc tgtgatgggc ctcatgtact ggacagactg gggggagaac   1440
cccaaaatcg aatgcgccaa cctagatggg agagatcggc atgtcctggt gaacacctcc   1500
cttgggtggc ccaatggact ggccctggac ctgcaggagg gcaagctgta ctgggggggat   1560 gccaaaactg ataaaatcga ggtgatcaac atagacggga caaagcggaa gaccctgctt   1620
gaggacaagc tcccacacat tttttgggttc acactgctgg gggacttcat ctactggacc   1680
gactggcaga gacgcagtat tgaaaggggtc cacaaggtca aggccagccg ggatgtcatc   1740
attgatcaac tccccgacct gatgggactc aaagccgtga atgtggccaa ggttgtcgga   1800
accaacccat gtgcggatgg aaatggaggg tgcagccatc tgtgcttctt caccccacgt   1860
gccaccaagt gtgctgccc cattggcctg gagctgttga gtgacatgaa gacctgcata   1920
atccccgagg ccttcctggt attcaccagc agagccacca tccacaggat ctccctggag   1980
actaacaaca cgatgtggc tatcccactc acgggtgtca agaggcctc tgcactggac   2040 tttgatgtgt ccaacaatca catctactgg actgatgtta gcctcaagac gatcagccga   2100
gccttcatga atgggagctc agtggagcac gtgattgagt ttggcctcga ctaccctgaa   2160
ggaatggctg tggactggat gggcaagaac ctctattggg cggacacagg gaccaacagg   2220
attgaggtgg cccggctgga tgggcagttc cggcaggtgc ttgtgtggag agaccttgac   2280
aaccccaggt ctctggctct ggatcctact aaaggctaca tctactggac tgagtggggt   2340
ggcaagccaa ggattgtgcg ggccttcatg gatgggacca attgtatgac actggtagac   2400
aaggtgggcc gggccaacga cctcaccatt gattatgccg accagcgact gtactggact   2460
gacctggaca ccaacatgat tgagtcttcc aacatgctgg gtcaggagcg catggtgata   2520
gctgacgatc tgccctaccc gttggcctg actcaatata gcgattacat ctactggact   2580
gactggaacc tgcatagcat tgaacgggcg gacaagacca gtgggcggaa ccgcacccctc   2640 atccagggtc acctggactt cgtcatggac atcctggtgt tccactcctc ccgtcaggat   2700
ggcctcaacg actgcgtgca cagcaatggc cagtgtgggc agctgtgcct cgccatcccc   2760
ggaggccacc gctgtggctg tgcttcacac tacacgctgg accccagcag ccgcaactgc   2820
agccccgcct ccaccttctt gctgttcagc cagaaatttg ccatcagccg gatgatcccc   2880
gatgaccagc tcagcccgga ccttgtccta ccccttcatg ggctgaggaa cgtcaaagcc   2940
atcaactatg acccgctgga caagttcatc tactgggtgg acgggcgcca gaacatcaag   3000
agggccaagg acgacggtac ccagcccctcc atgctgacct ctcccagcca aagcctgagc   3060
ccagacagac agccacacga cctcagcatt gacatctaca gccggacact gttctggacc   3120
tgtgaggcca ccaacactat caatgtccac cggctggatg gggatgccat gggagtggtg   3180
cttcgagggg accgtgacaa gccaaggggcc attgctgtca atgctgagcg agggtacatg   3240
tactttacca acatgcagga ccatgctgcc aagatcgagc gagcctccct ggatggcaca   3300
gagcgggagg tcctcttcac cacaggcctc atccgtcccg tggcccttgt ggtggacaat   3360
```

```
gctctgggca agctcttctg ggtggatgcc gacctaaagc gaatcgaaag ctgtgacctc    3420
tctggggcca accgcctgac cctggaagat gccaacatcg tacagccagt aggtctgaca    3480
gtgctgggca ggcacctcta ctggatcgac cgccagcagc agatgatcga gcgcgtggag    3540
aagaccactg gggacaagcg gactagggtt cagggccgtg tcacccacct gacaggcatc    3600
catgccgtgg aggaagtcag cctggaggag ttctcagccc atccttgtgc ccagacaat    3660 ggcggctgct cccacatctg tatcgccaag ggtgatggaa caccgcgctg ctcgtgccct    3720
gtccacctgg tgctcctgca gaacctgctg acttgtggtg agcctcctac ctgctcccct    3780
gatcagtttg catgtaccac tggtgagatc gactgcatcc ccggagcctg cgctgtgac    3840 ggcttccctg agtgtgctga ccagagtgat gaagaaggct gcccagtgtg ctccgcctct    3900
cagttcccct gcgctcgagg ccagtgtgtg gacctgcggt tacgctgcga cggtgaggcc    3960
gactgccagg atcgctctga tgaagctaac tgcgatgctg tctgtctgcc caatcagttc    4020
cggtgcacca gcggccagtg tgtcctcatc aagcaacagt gtgactcctt ccccgactgt    4080
gctgatgggt ctgatgagct catgtgtgaa atcaacaagc caccctctga tgacatccca    4140
gcccacagca gtgccattgg gcccgtcatt ggtatcatcc tctccctctt cgtcatgggc    4200
ggggtctact ttgtctgcca gcgtgtgatg tgccagcgct acacaggggc cagtgggccc    4260
tttccccacg agtatgttgg tggagcccct catgtgcctc tcaacttcat agccccaggt    4320
ggctcacagc acggtccctt cccaggcatc ccgtgcagca agtccgtgat gagctccatg    4380
agcctggtgg gggggcgcgg cagcgtgccc ctctatgacc ggaatcacgt cactggggcc    4440
tcatccagca gctcgtccag cacaaaggcc acactatatc cgccgatcct gaacccaccc    4500
ccgtccccgg ccacagaccc ctctctctac aacgtggacg tgttttattc ttcaggcatc    4560
ccggccaccg ctagaccata caggccctac gtcattcgag gtatggcacc cccaacaaca    4620
ccgtgcagca cagatgtgtg tgacagtgac tacagcatca gtcgctggaa gagcagcaaa    4680
tactacctgg acttgaattc ggactcagac ccctacccc cccgcccac ccccacagc    4740 cagtacctat ctgcagagga cagctgccca ccctcaccag gcactgagag gagttactgc    4800
cacctcttcc cgcccccacc gtcccctgc acggactcgt cctga    4845
```

<210> SEQ ID NO 14
<211> LENGTH: 1614
<212> TYPE: PRT
<213> ORGANISM: Mouse

<400> SEQUENCE: 14

```
Met Glu Thr Ala Pro Thr Arg Ala Pro Pro Pro Pro Pro Pro Leu
1               5                  10                  15

Leu Leu Val Leu Tyr Cys Ser Leu Val Pro Ala Ala Ala Ser Pro
            20                  25                  30

Leu Leu Leu Phe Ala Asn Arg Arg Asp Val Arg Leu Val Asp Ala Gly
            35                  40                  45

Gly Val Lys Leu Glu Ser Thr Ile Val Ala Ser Gly Leu Glu Asp Ala
        50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                    85                  90                  95

Ala Ala Gln Asn Ile Val Ile Ser Gly Leu Val Ser Pro Asp Gly Leu
                100                 105                 110
```

```
Ala Cys Asp Trp Val Gly Lys Lys Leu Tyr Trp Thr Asp Ser Glu Thr
        115                 120                 125

Asn Arg Ile Glu Val Ala Asn Leu Asn Gly Thr Ser Arg Lys Val Leu
        130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Ala Pro Arg Ile Glu
                165                 170                 175

Arg Ala Gly Met Asp Gly Ser Thr Arg Lys Ile Ile Val Asp Ser Asp
                180                 185                 190

Ile Tyr Trp Pro Asn Gly Leu Thr Ile Asp Leu Glu Glu Gln Lys Leu
        195                 200                 205

Tyr Trp Ala Asp Ala Lys Leu Ser Phe Ile His Arg Ala Asn Leu Asp
        210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
                245                 250                 255

Arg Ser Ile His Ala Cys Asn Lys Trp Thr Gly Glu Gln Arg Lys Glu
                260                 265                 270

Ile Leu Ser Ala Leu Tyr Ser Pro Met Asp Ile Gln Val Leu Ser Gln
        275                 280                 285

Glu Arg Gln Pro Pro Phe His Thr Pro Cys Glu Glu Asp Asn Gly Gly
        290                 295                 300

Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                325                 330                 335

Thr Gly Ala Glu Glu Val Leu Leu Leu Ala Arg Arg Thr Asp Leu Arg
                340                 345                 350

Arg Ile Ser Leu Asp Thr Pro Asp Phe Thr Asp Ile Val Leu Gln Val
        355                 360                 365

Gly Asp Ile Arg His Ala Ile Ala Ile Asp Tyr Asp Pro Leu Glu Gly
        370                 375                 380

Tyr Val Tyr Trp Thr Asp Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
                405                 410                 415

Pro Asp Gly Ile Ala Val Asp Trp Val Ala Arg Asn Leu Tyr Trp Thr
                420                 425                 430

Asp Thr Gly Thr Asp Arg Ile Glu Val Thr Arg Leu Asn Gly Thr Ser
        435                 440                 445

Arg Lys Ile Leu Val Ser Glu Asp Leu Asp Glu Pro Arg Ala Ile Val
        450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                485                 490                 495

Val Asn Thr Ser Leu Gly Trp Pro Asn Gly Leu Ala Leu Asp Leu Gln
        500                 505                 510

Glu Gly Lys Leu Tyr Trp Gly Asp Ala Lys Thr Asp Lys Ile Glu Val
        515                 520                 525
```

-continued

```
Ile Asn Ile Asp Gly Thr Lys Arg Lys Thr Leu Leu Glu Asp Lys Leu
    530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590

Val Asn Val Ala Lys Val Val Gly Thr Asn Pro Cys Ala Asp Gly Asn
        595                 600                 605

Gly Gly Cys Ser His Leu Cys Phe Phe Thr Pro Arg Ala Thr Lys Cys
    610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
        675                 680                 685

Tyr Trp Thr Asp Val Ser Leu Lys Thr Ile Ser Arg Ala Phe Met Asn
    690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
            740                 745                 750

Val Leu Val Trp Arg Asp Leu Asp Asn Pro Arg Ser Leu Ala Leu Asp
        755                 760                 765

Pro Thr Lys Gly Tyr Ile Tyr Trp Thr Glu Trp Gly Gly Lys Pro Arg
    770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
            820                 825                 830

Leu Gly Gln Glu Arg Met Val Ile Ala Asp Asp Leu Pro Tyr Pro Phe
        835                 840                 845

Gly Leu Thr Gln Tyr Ser Asp Tyr Ile Tyr Trp Thr Asp Trp Asn Leu
    850                 855                 860

His Ser Ile Glu Arg Ala Asp Lys Thr Ser Gly Arg Asn Arg Thr Leu
865                 870                 875                 880

Ile Gln Gly His Leu Asp Phe Val Met Asp Ile Leu Val Phe His Ser
                885                 890                 895

Ser Arg Gln Asp Gly Leu Asn Asp Cys Val His Ser Asn Gly Gln Cys
            900                 905                 910

Gly Gln Leu Cys Leu Ala Ile Pro Gly Gly His Arg Cys Gly Cys Ala
        915                 920                 925

Ser His Tyr Thr Leu Asp Pro Ser Ser Arg Asn Cys Ser Pro Pro Ser
    930                 935                 940

Thr Phe Leu Leu Phe Ser Gln Lys Phe Ala Ile Ser Arg Met Ile Pro
```

-continued

```
              945                 950                 955                 960
Asp Asp Gln Leu Ser Pro Asp Leu Val Leu Pro Leu His Gly Leu Arg
              965                 970                 975
Asn Val Lys Ala Ile Asn Tyr Asp Pro Leu Asp Lys Phe Ile Tyr Trp
              980                 985                 990
Val Asp Gly Arg Gln Asn Ile Lys Arg Ala Lys Asp Asp Gly Thr Gln
              995                 1000                1005
Pro Ser Met Leu Thr Ser Pro Ser Gln Ser Leu Ser Pro Asp Arg
    1010                1015                1020
Gln Pro His Asp Leu Ser Ile Asp Ile Tyr Ser Arg Thr Leu Phe
    1025                1030                1035
Trp Thr Cys Glu Ala Thr Asn Thr Ile Asn Val His Arg Leu Asp
    1040                1045                1050
Gly Asp Ala Met Gly Val Val Leu Arg Gly Asp Arg Asp Lys Pro
    1055                1060                1065
Arg Ala Ile Ala Val Asn Ala Glu Arg Gly Tyr Met Tyr Phe Thr
    1070                1075                1080
Asn Met Gln Asp His Ala Ala Lys Ile Glu Arg Ala Ser Leu Asp
    1085                1090                1095
Gly Thr Glu Arg Glu Val Leu Phe Thr Thr Gly Leu Ile Arg Pro
    1100                1105                1110
Val Ala Leu Val Val Asp Asn Ala Leu Gly Lys Leu Phe Trp Val
    1115                1120                1125
Asp Ala Asp Leu Lys Arg Ile Glu Ser Cys Asp Leu Ser Gly Ala
    1130                1135                1140
Asn Arg Leu Thr Leu Glu Asp Ala Asn Ile Val Gln Pro Val Gly
    1145                1150                1155
Leu Thr Val Leu Gly Arg His Leu Tyr Trp Ile Asp Arg Gln Gln
    1160                1165                1170
Gln Met Ile Glu Arg Val Glu Lys Thr Thr Gly Asp Lys Arg Thr
    1175                1180                1185
Arg Val Gln Gly Arg Val Thr His Leu Thr Gly Ile His Ala Val
    1190                1195                1200
Glu Glu Val Ser Leu Glu Glu Phe Ser Ala His Pro Cys Ala Arg
    1205                1210                1215
Asp Asn Gly Gly Cys Ser His Ile Cys Ile Ala Lys Gly Asp Gly
    1220                1225                1230
Thr Pro Arg Cys Ser Cys Pro Val His Leu Val Leu Leu Gln Asn
    1235                1240                1245
Leu Leu Thr Cys Gly Glu Pro Pro Thr Cys Ser Pro Asp Gln Phe
    1250                1255                1260
Ala Cys Thr Thr Gly Glu Ile Asp Cys Ile Pro Gly Ala Trp Arg
    1265                1270                1275
Cys Asp Gly Phe Pro Glu Cys Ala Asp Gln Ser Asp Glu Glu Gly
    1280                1285                1290
Cys Pro Val Cys Ser Ala Ser Gln Phe Pro Cys Ala Arg Gly Gln
    1295                1300                1305
Cys Val Asp Leu Arg Leu Arg Cys Asp Gly Glu Ala Asp Cys Gln
    1310                1315                1320
Asp Arg Ser Asp Glu Ala Asn Cys Asp Ala Val Cys Leu Pro Asn
    1325                1330                1335
Gln Phe Arg Cys Thr Ser Gly Gln Cys Val Leu Ile Lys Gln Gln
    1340                1345                1350
```

```
Cys Asp Ser Phe Pro Asp Cys Ala Asp Gly Ser Asp Glu Leu Met
    1355                1360                1365

Cys Glu Ile Asn Lys Pro Pro Ser Asp Asp Ile Pro Ala His Ser
    1370                1375                1380

Ser Ala Ile Gly Pro Val Ile Gly Ile Ile Leu Ser Leu Phe Val
    1385                1390                1395

Met Gly Gly Val Tyr Phe Val Cys Gln Arg Val Met Cys Gln Arg
    1400                1405                1410

Tyr Thr Gly Ala Ser Gly Pro Phe Pro His Glu Tyr Val Gly Gly
    1415                1420                1425

Ala Pro His Val Pro Leu Asn Phe Ile Ala Pro Gly Gly Ser Gln
    1430                1435                1440

His Gly Pro Phe Pro Gly Ile Pro Cys Ser Lys Ser Val Met Ser
    1445                1450                1455

Ser Met Ser Leu Val Gly Gly Arg Gly Ser Val Pro Leu Tyr Asp
    1460                1465                1470

Arg Asn His Val Thr Gly Ala Ser Ser Ser Ser Ser Ser Ser Thr
    1475                1480                1485

Lys Ala Thr Leu Tyr Pro Pro Ile Leu Asn Pro Pro Pro Ser Pro
    1490                1495                1500

Ala Thr Asp Pro Ser Leu Tyr Asn Val Asp Val Phe Tyr Ser Ser
    1505                1510                1515

Gly Ile Pro Ala Thr Ala Arg Pro Tyr Arg Pro Tyr Val Ile Arg
    1520                1525                1530

Gly Met Ala Pro Pro Thr Thr Pro Cys Ser Thr Asp Val Cys Asp
    1535                1540                1545

Ser Asp Tyr Ser Ile Ser Arg Trp Lys Ser Ser Lys Tyr Tyr Leu
    1550                1555                1560

Asp Leu Asn Ser Asp Ser Asp Pro Tyr Pro Pro Pro Thr Pro
    1565                1570                1575

His Ser Gln Tyr Leu Ser Ala Glu Asp Ser Cys Pro Pro Ser Pro
    1580                1585                1590

Gly Thr Glu Arg Ser Tyr Cys His Leu Phe Pro Pro Pro Pro Ser
    1595                1600                1605

Pro Cys Thr Asp Ser Ser
    1610

<210> SEQ ID NO 15
<211> LENGTH: 14
<212> TYPE: PRT
<213> ORGANISM: Human

<400> SEQUENCE: 15

Glu Asn Asn Lys Thr Met Asn Arg Ala Glu Asn Gly Gly Arg
1               5                   10

<210> SEQ ID NO 16
<211> LENGTH: 16
<212> TYPE: PRT
<213> ORGANISM: Human

<400> SEQUENCE: 16

His Pro Phe Glu Thr Lys Asp Val Ser Glu Tyr Ser Cys Arg Glu Leu
1               5                   10                  15

<210> SEQ ID NO 17
```

```
<211> LENGTH: 17
<212> TYPE: PRT
<213> ORGANISM: Human

<400> SEQUENCE: 17

Arg Glu Leu His Phe Thr Arg Tyr Val Thr Asp Gly Pro Cys Arg Ser
1               5                   10                  15

Ala

<210> SEQ ID NO 18
<211> LENGTH: 12
<212> TYPE: PRT
<213> ORGANISM: Human

<400> SEQUENCE: 18

Leu Cys Pro Gly Gly Glu Ala Pro Arg Ala Arg Lys
1               5                   10

<210> SEQ ID NO 19
<211> LENGTH: 615
<212> TYPE: DNA
<213> ORGANISM: Mouse

<400> SEQUENCE: 19
atgcagccct cactagcccc gtgcctcatc tgcctacttg tgcacgctgc cttctgtgct      60
gtggagggcc aggggtggca agccttcagg aatgatgcca cagaggtcat cccagggctt     120
ggagagtacc ccgagcctac tcctgagaac aaccagacca tgaaccgggc ggagaatggt     180
ggcagacctc cccaccatcc ctatgacgcc aaagatgtgt ccgagtacag ctgccgcgag     240
ctgcactaca cccgcttcct gacagacggc ccatgccgca cgccaagcc ggtcaccgag      300 ttggtgtgct ccggccagtg cggccccgcg cggctgctgc caacgccat cgggcgcgtg      360 aagtggtggc gcccgaacgg accggatttc cgctgcatcc cggatcgcta ccgcgcgcag     420
cgggtgcagc tgctgtgccc cggggggcgcg gcgccacgct cgcgcaaggt gcgtctggtg     480
gcctcgtgca gtgcaagcg ccccacccgc ttccacaacc agtcggagct caaggacttc     540
gggccggaga ccgcgcggcc gcagaagggt cgcaagccgc ggcccggcgc ccggggagcc     600
aaagccaacc aggcg                                                     615

<210> SEQ ID NO 20
<211> LENGTH: 203
<212> TYPE: PRT
<213> ORGANISM: Mouse

<400> SEQUENCE: 20

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
                20                  25                  30

Ala Thr Glu Val Ile Pro Gly Leu Gly Glu Tyr Pro Glu Pro Pro
            35                  40                  45

Glu Asn Asn Gln Thr Met Asn Arg Ala Glu Asn Gly Gly Arg Pro Pro
        50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
```

-continued

```
                    100                 105                 110
Leu Pro Asn Ala Ile Gly Arg Val Lys Trp Trp Arg Pro Asn Gly Pro
            115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn
        195                 200

<210> SEQ ID NO 21
<211> LENGTH: 203
<212> TYPE: PRT
<213> ORGANISM: Artificial
<220> FEATURE:
<223> OTHER INFORMATION: Wise/SOST Peptides

<400> SEQUENCE: 21

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn
        195                 200

<210> SEQ ID NO 22
<211> LENGTH: 14
<212> TYPE: PRT
<213> ORGANISM: Artificial
<220> FEATURE:
<223> OTHER INFORMATION: Wise/SOST Peptides

<400> SEQUENCE: 22
```

```
Leu Asn Asn Lys Thr Met Asn Arg Ala Glu Asn Gly Gly Arg
1               5                   10
```

<210> SEQ ID NO 23
<211> LENGTH: 14
<212> TYPE: PRT
<213> ORGANISM: Artificial
<220> FEATURE:
<223> OTHER INFORMATION: Wise/SOST Peptides

<400> SEQUENCE: 23

```
Ser Ser Asn Ser Thr Met Asn Gln Ala Arg Asn Gly Gly Arg
1               5                   10
```

<210> SEQ ID NO 24
<211> LENGTH: 14
<212> TYPE: PRT
<213> ORGANISM: Artificial
<220> FEATURE:
<223> OTHER INFORMATION: Wise/SOST Peptides

<400> SEQUENCE: 24

```
Ala Asn Ser Ser Ala Leu Asn Gln Ala Arg Asn Gly Gly Arg
1               5                   10
```

<210> SEQ ID NO 25
<211> LENGTH: 14
<212> TYPE: PRT
<213> ORGANISM: Artificial
<220> FEATURE:
<223> OTHER INFORMATION: Wise/SOST Peptides

<400> SEQUENCE: 25

```
Ala Asn Ser Ser Thr Leu Asn Gln Ala Arg Asn Gly Gly Arg
1               5                   10
```

<210> SEQ ID NO 26
<211> LENGTH: 14
<212> TYPE: PRT
<213> ORGANISM: Artificial
<220> FEATURE:
<223> OTHER INFORMATION: Wise/SOST Peptides

<400> SEQUENCE: 26

```
Ser Ser Ser Asn Gly Gly Asn Arg Ala Lys Ser Gly Gly Arg
1               5                   10
```

<210> SEQ ID NO 27
<211> LENGTH: 14
<212> TYPE: PRT
<213> ORGANISM: Artificial
<220> FEATURE:
<223> OTHER INFORMATION: Wise/SOST Peptides

<400> SEQUENCE: 27

```
Ala Ser Ser Asn Ala Gly Asn Arg Ala Lys Ser Gly Ala Arg
1               5                   10
```

<210> SEQ ID NO 28
<211> LENGTH: 14
<212> TYPE: PRT
<213> ORGANISM: Artificial
<220> FEATURE:
<223> OTHER INFORMATION: Wise/SOST Peptides

<400> SEQUENCE: 28

```
Ser Asn Asn Asn Thr Met Asn Gln Ala Lys His Gly Gly Arg
```

```
<210> SEQ ID NO 29
<211> LENGTH: 14
<212> TYPE: PRT
<213> ORGANISM: Artificial
<220> FEATURE:
<223> OTHER INFORMATION: Wise/SOST Peptides

<400> SEQUENCE: 29

Glu Asn Asn Gln Thr Met Asn Arg Ala Glu Asn Gly Gly Arg
1               5                   10

<210> SEQ ID NO 30
<211> LENGTH: 16
<212> TYPE: PRT
<213> ORGANISM: Artificial
<220> FEATURE:
<223> OTHER INFORMATION: Wise/SOST Peptides

<400> SEQUENCE: 30

His Pro Phe Glu Thr Lys Asp Ala Ser Glu Tyr Ser Cys Arg Glu Leu
1               5                   10                  15

<210> SEQ ID NO 31
<211> LENGTH: 16
<212> TYPE: PRT
<213> ORGANISM: Artificial
<220> FEATURE:
<223> OTHER INFORMATION: Wise/SOST Peptides

<400> SEQUENCE: 31

His Pro Tyr Asp Ala Lys Gly Val Ser Glu Tyr Ser Cys Arg Glu Leu
1               5                   10                  15

<210> SEQ ID NO 32
<211> LENGTH: 16
<212> TYPE: PRT
<213> ORGANISM: Artificial
<220> FEATURE:
<223> OTHER INFORMATION: Wise/SOST Peptides

<400> SEQUENCE: 32

His Pro Tyr Asp Thr Lys Asp Val Ser Glu Tyr Ser Cys Arg Glu Leu
1               5                   10                  15

<210> SEQ ID NO 33
<211> LENGTH: 16
<212> TYPE: PRT
<213> ORGANISM: Artificial
<220> FEATURE:
<223> OTHER INFORMATION: Wise/SOST Peptides

<400> SEQUENCE: 33

Gln Ala Pro Asp Pro Asn Asp Val Ser Asp Phe Ser Cys Arg Glu Met
1               5                   10                  15

<210> SEQ ID NO 34
<211> LENGTH: 16
<212> TYPE: PRT
<213> ORGANISM: Artificial
<220> FEATURE:
<223> OTHER INFORMATION: Wise/SOST Peptides

<400> SEQUENCE: 34

Thr Gly Leu Asp Arg Asn Thr Arg Val Gln Val Gly Cys Arg Glu Leu
1               5                   10                  15
```

```
<210> SEQ ID NO 35
<211> LENGTH: 16
<212> TYPE: PRT
<213> ORGANISM: Artificial
<220> FEATURE:
<223> OTHER INFORMATION: Wise/SOST Peptides

<400> SEQUENCE: 35

Thr Gly Leu Asp Arg Asn Ser Arg Val Gln Val Gly Cys Arg Glu Leu
1               5                   10                  15

<210> SEQ ID NO 36
<211> LENGTH: 16
<212> TYPE: PRT
<213> ORGANISM: Artificial
<220> FEATURE:
<223> OTHER INFORMATION: Wise/SOST Peptides

<400> SEQUENCE: 36

Thr Gly Ser Asp Arg Asn Asn Arg Val Gln Val Gly Cys Arg Glu Leu
1               5                   10                  15

<210> SEQ ID NO 37
<211> LENGTH: 16
<212> TYPE: PRT
<213> ORGANISM: Artificial
<220> FEATURE:
<223> OTHER INFORMATION: Wise/SOST Peptides

<400> SEQUENCE: 37

Ser Ala Met Asp Arg Thr Asn Pro His Gln Val Gly Cys Arg Glu Leu
1               5                   10                  15

<210> SEQ ID NO 38
<211> LENGTH: 16
<212> TYPE: PRT
<213> ORGANISM: Artificial
<220> FEATURE:
<223> OTHER INFORMATION: Wise/SOST Peptides

<400> SEQUENCE: 38

Ser Ala Leu Asp Arg Thr Asn His His Gln Val Gly Cys Arg Glu Leu
1               5                   10                  15

<210> SEQ ID NO 39
<211> LENGTH: 16
<212> TYPE: PRT
<213> ORGANISM: Artificial
<220> FEATURE:
<223> OTHER INFORMATION: Wise/SOST Peptides

<400> SEQUENCE: 39

Thr Ser Ser Val Thr Tyr Ser Ala Ser Glu Leu Ser Cys Arg Glu Leu
1               5                   10                  15

<210> SEQ ID NO 40
<211> LENGTH: 16
<212> TYPE: PRT
<213> ORGANISM: Artificial
<220> FEATURE:
<223> OTHER INFORMATION: Wise/SOST Peptides

<400> SEQUENCE: 40

Thr Ser Thr Val Ser Tyr Ser Ala Ser Glu Leu Ser Cys Arg Glu Leu
1               5                   10                  15
```

```
<210> SEQ ID NO 41
<211> LENGTH: 17
<212> TYPE: PRT
<213> ORGANISM: Artificial
<220> FEATURE:
<223> OTHER INFORMATION: Wise/SOST Peptides

<400> SEQUENCE: 41

Arg Glu Leu Arg Ser Thr Lys Tyr Ile Ser Asp Gly Gln Cys Thr Ser
1               5                   10                  15

Ile

<210> SEQ ID NO 42
<211> LENGTH: 16
<212> TYPE: PRT
<213> ORGANISM: Artificial
<220> FEATURE:
<223> OTHER INFORMATION: Wise/SOST Peptodes

<400> SEQUENCE: 42

Lys Thr Gln Pro Leu Lys Gln Thr Ile His Glu Asp Gly Cys Asn Ser
1               5                   10                  15

<210> SEQ ID NO 43
<211> LENGTH: 17
<212> TYPE: PRT
<213> ORGANISM: Artificial
<220> FEATURE:
<223> OTHER INFORMATION: Wise/SOST Peptides

<400> SEQUENCE: 43

Arg Glu Leu Arg Ser Thr Arg Tyr Val Thr Asp Gly Ser Cys Arg Ser
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Wise/SOST Peptides

<400> SEQUENCE: 44

Arg Glu Met Arg Ile Thr Arg Tyr Val Thr Glu Gly Pro Cys Arg Ser
1               5                   10                  15

Leu

<210> SEQ ID NO 45
<211> LENGTH: 17
<212> TYPE: PRT
<213> ORGANISM: Artificial
<220> FEATURE:
<223> OTHER INFORMATION: Wise/SOST Peptides

<400> SEQUENCE: 45

Arg Glu Leu His Tyr Thr Arg Phe Leu Thr Asp Gly Pro Cys Arg Ser
1               5                   10                  15

Ala

<210> SEQ ID NO 46
<211> LENGTH: 15
<212> TYPE: PRT
<213> ORGANISM: Artificial
<220> FEATURE:
```

<223> OTHER INFORMATION: Wise/SOST Peptides

<400> SEQUENCE: 46

Glu Leu Val Cys Ser Gly Gln Cys Gly Pro Ala Arg Leu Leu Pro
1               5                   10                  15

<210> SEQ ID NO 47
<211> LENGTH: 15
<212> TYPE: PRT
<213> ORGANISM: Artificial
<220> FEATURE:
<223> OTHER INFORMATION: Wise/SOST Peptides

<400> SEQUENCE: 47

Glu Leu Val Cys Ser Gly Gln Cys Val Pro Ser His Leu Leu Pro
1               5                   10                  15

<210> SEQ ID NO 48
<211> LENGTH: 15
<212> TYPE: PRT
<213> ORGANISM: Artificial
<220> FEATURE:
<223> OTHER INFORMATION: Wise/SOST Peptides

<400> SEQUENCE: 48

Glu Leu Val Cys Ser Gly Gln Cys Leu Pro Ala His Leu Met Pro
1               5                   10                  15

<210> SEQ ID NO 49
<211> LENGTH: 15
<212> TYPE: PRT
<213> ORGANISM: Artificial
<220> FEATURE:
<223> OTHER INFORMATION: Wise/SOST Peptides

<400> SEQUENCE: 49

Glu Leu Val Cys Thr Gly Gln Cys Leu Pro Ala Gln Met Leu Pro
1               5                   10                  15

<210> SEQ ID NO 50
<211> LENGTH: 15
<212> TYPE: PRT
<213> ORGANISM: Artificial
<220> FEATURE:
<223> OTHER INFORMATION: Wise/SOST Peptides

<400> SEQUENCE: 50

Glu Leu Val Cys Ala Gly Glu Cys Leu Pro Leu Pro Ile Leu Pro
1               5                   10                  15

<210> SEQ ID NO 51
<211> LENGTH: 15
<212> TYPE: PRT
<213> ORGANISM: Artificial
<220> FEATURE:
<223> OTHER INFORMATION: Wise/SOST Peptides

<400> SEQUENCE: 51

Glu Leu Val Cys Ala Gly Glu Cys Leu Pro Leu Pro Leu Leu Pro
1               5                   10                  15

<210> SEQ ID NO 52
<211> LENGTH: 15
<212> TYPE: PRT
<213> ORGANISM: Artificial
<220> FEATURE:
<223> OTHER INFORMATION: Wise/SOST Peptides

```
<400> SEQUENCE: 52

Glu Leu Val Cys Ala Gly Glu Cys Leu Pro Leu Pro Val Leu Pro
1               5                   10                  15

<210> SEQ ID NO 53
<211> LENGTH: 15
<212> TYPE: PRT
<213> ORGANISM: Artificial
<220> FEATURE:
<223> OTHER INFORMATION: Wise/SOST Peptides

<400> SEQUENCE: 53

Glu Leu Val Cys Ser Gly Gln Cys Gly Pro Ala Arg Leu Leu Pro
1               5                   10                  15

<210> SEQ ID NO 54
<211> LENGTH: 15
<212> TYPE: PRT
<213> ORGANISM: Artificial
<220> FEATURE:
<223> OTHER INFORMATION: Wise/SOST Peptides

<400> SEQUENCE: 54

Glu Leu Val Cys Ala Gly Glu Cys Leu Pro Leu Ser Val Leu Pro
1               5                   10                  15

<210> SEQ ID NO 55
<211> LENGTH: 15
<212> TYPE: PRT
<213> ORGANISM: Artificial
<220> FEATURE:
<223> OTHER INFORMATION: Wise/SOST Peptides

<400> SEQUENCE: 55

Glu Leu Val Cys Ser Gly Gln Cys Gly Pro Ala Arg Leu Leu Pro
1               5                   10                  15

<210> SEQ ID NO 56
<211> LENGTH: 21
<212> TYPE: PRT
<213> ORGANISM: Artificial
<220> FEATURE:
<223> OTHER INFORMATION: Wise/SOST Peptides

<400> SEQUENCE: 56

Asn Ala Ile Gly Arg Gly Lys Trp Trp Arg Pro Ser Gly Pro Asp Phe
1               5                   10                  15

Arg Cys Ile Pro Asp
            20

<210> SEQ ID NO 57
<211> LENGTH: 25
<212> TYPE: PRT
<213> ORGANISM: Artificial
<220> FEATURE:
<223> OTHER INFORMATION: Wise/SOST Peptides

<400> SEQUENCE: 57

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 58
```

-continued

```
<211> LENGTH: 25
<212> TYPE: PRT
<213> ORGANISM: Artificial
<220> FEATURE:
<223> OTHER INFORMATION: Wise Peptides

<400> SEQUENCE: 58

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 59
<211> LENGTH: 21
<212> TYPE: PRT
<213> ORGANISM: Artificial
<220> FEATURE:
<223> OTHER INFORMATION: Wise Peptides

<400> SEQUENCE: 59

Asn Ala Ile Gly Arg Gly Lys Trp Trp Arg Pro Ser Gly Pro Asp Phe
1               5                   10                  15

Arg Cys Ile Pro Asp
            20

<210> SEQ ID NO 60
<211> LENGTH: 25
<212> TYPE: PRT
<213> ORGANISM: Artificial
<220> FEATURE:
<223> OTHER INFORMATION: Wise Peptides

<400> SEQUENCE: 60

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 61
<211> LENGTH: 25
<212> TYPE: PRT
<213> ORGANISM: Artificial
<220> FEATURE:
<223> OTHER INFORMATION: Wise/SOST Peptides

<400> SEQUENCE: 61

Asn Trp Ile Gly Gly Gly Tyr Gly Thr Lys Tyr Trp Ser Arg Arg Gly
1               5                   10                  15

Ser Gln Glu Trp Arg Cys Val Asn Asp
            20                  25

<210> SEQ ID NO 62
<211> LENGTH: 24
<212> TYPE: PRT
<213> ORGANISM: Artificial
<220> FEATURE:
<223> OTHER INFORMATION: Wise/SOST Peptides

<400> SEQUENCE: 62

Asn Trp Ile Gly Gly Tyr Gly Lys Lys Ser Trp Asn Arg Arg Asn Ser
1               5                   10                  15

Gln Glu Trp Arg Cys Val Asn Asp
            20
```

```
<210> SEQ ID NO 63
<211> LENGTH: 21
<212> TYPE: PRT
<213> ORGANISM: Artificial
<220> FEATURE:
<223> OTHER INFORMATION: Wise/SOST Peptides

<400> SEQUENCE: 63

Asn Thr Ile Gly Arg Gly Lys Trp Trp Arg Ser Asn Thr Ser Glu Tyr
1               5                   10                  15

Arg Cys Ile Pro Ala
            20

<210> SEQ ID NO 64
<211> LENGTH: 21
<212> TYPE: PRT
<213> ORGANISM: Artificial
<220> FEATURE:
<223> OTHER INFORMATION: Wise/SOST Peptides

<400> SEQUENCE: 64

Asn Thr Ile Gly Arg Ala Lys Trp Trp Arg Ser Ser Thr Ser Glu Tyr
1               5                   10                  15

Arg Cys Val Pro Ala
            20

<210> SEQ ID NO 65
<211> LENGTH: 21
<212> TYPE: PRT
<213> ORGANISM: Artificial
<220> FEATURE:
<223> OTHER INFORMATION: Wise/SOST Peptides

<400> SEQUENCE: 65

Asn Ser Ile Gly Arg Gly Lys Trp Trp Arg Gln Asn Ser Pro Asp Tyr
1               5                   10                  15

Arg Cys Ile Pro Ala
            20

<210> SEQ ID NO 66
<211> LENGTH: 21
<212> TYPE: PRT
<213> ORGANISM: Artificial
<220> FEATURE:
<223> OTHER INFORMATION: Wise/SOST Peptides

<400> SEQUENCE: 66

Asn Ala Ile Gly Arg Val Lys Trp Trp Arg Pro Asn Gly Pro Asp Phe
1               5                   10                  15

Arg Cys Ile Pro Asp
            20

<210> SEQ ID NO 67
<211> LENGTH: 21
<212> TYPE: PRT
<213> ORGANISM: Artificial
<220> FEATURE:
<223> OTHER INFORMATION: Wise/SOST Peptides

<400> SEQUENCE: 67

Asn Ala Ile Gly Arg Gly Lys Trp Trp Arg Pro Ser Gly Pro Asp Phe
1               5                   10                  15

Arg Cys Ile Pro Asp
            20
```

```
<210> SEQ ID NO 68
<211> LENGTH: 13
<212> TYPE: PRT
<213> ORGANISM: Artificial
<220> FEATURE:
<223> OTHER INFORMATION: Wise/SOST Peptides

<400> SEQUENCE: 68

Leu Leu Cys Pro Gly Gly Ala Ala Pro Arg Ala Arg Lys
1               5                   10

<210> SEQ ID NO 69
<211> LENGTH: 13
<212> TYPE: PRT
<213> ORGANISM: Artificial
<220> FEATURE:
<223> OTHER INFORMATION: Wise/SOST Peptides

<400> SEQUENCE: 69

Leu Leu Cys Pro Gly Gly Glu Ala Pro Arg Ala Arg Lys
1               5                   10

<210> SEQ ID NO 70
<211> LENGTH: 12
<212> TYPE: PRT
<213> ORGANISM: Artificial
<220> FEATURE:
<223> OTHER INFORMATION: Wise/SOST Peptides

<400> SEQUENCE: 70

Leu Gln Cys Gln Asp Gly Ser Thr Arg Thr Tyr Lys
1               5                   10

<210> SEQ ID NO 71
<211> LENGTH: 12
<212> TYPE: PRT
<213> ORGANISM: Artificial
<220> FEATURE:
<223> OTHER INFORMATION: Wise/SOST Peptides

<400> SEQUENCE: 71

Leu Gln Cys Glu Asp Gly Thr Thr Arg Thr Tyr Lys
1               5                   10

<210> SEQ ID NO 72
<211> LENGTH: 12
<212> TYPE: PRT
<213> ORGANISM: Artificial
<220> FEATURE:
<223> OTHER INFORMATION: Wise/SOST Peptides

<400> SEQUENCE: 72

Leu Gln Cys Pro Asn Gly Asn Thr Arg Thr Tyr Lys
1               5                   10

<210> SEQ ID NO 73
<211> LENGTH: 12
<212> TYPE: PRT
<213> ORGANISM: Artificial
<220> FEATURE:
<223> OTHER INFORMATION: Wise/SOST Peptides

<400> SEQUENCE: 73

Leu Arg Cys Pro Asn Gly Asn Thr Arg Thr Tyr Lys
1               5                   10
```

```
<210> SEQ ID NO 74
<211> LENGTH: 12
<212> TYPE: PRT
<213> ORGANISM: Artificial
<220> FEATURE:
<223> OTHER INFORMATION: Wise/SOST Peptides

<400> SEQUENCE: 74

Met Ala Cys Pro Glu Asp Glu Thr Arg Thr Tyr Lys
1               5                   10

<210> SEQ ID NO 75
<211> LENGTH: 13
<212> TYPE: PRT
<213> ORGANISM: Artificial
<220> FEATURE:
<223> OTHER INFORMATION: Wise/SOST Peptides

<400> SEQUENCE: 75

Leu Leu Cys Pro Gly Gly Ala Ala Pro Arg Ser Arg Lys
1               5                   10

<210> SEQ ID NO 76
<211> LENGTH: 11
<212> TYPE: PRT
<213> ORGANISM: Artificial
<220> FEATURE:
<223> OTHER INFORMATION: Wise/SOST Peptides

<400> SEQUENCE: 76

Asp Thr Gly Thr Asp Arg Ile Glu Val Thr Arg
1               5                   10

<210> SEQ ID NO 77
<211> LENGTH: 11
<212> TYPE: PRT
<213> ORGANISM: Artificial
<220> FEATURE:
<223> OTHER INFORMATION: Wise/SOST Peptides

<400> SEQUENCE: 77

Asp Thr Val Thr Asp Arg Ile Glu Val Cys Arg
1               5                   10

<210> SEQ ID NO 78
<211> LENGTH: 11
<212> TYPE: PRT
<213> ORGANISM: Artificial
<220> FEATURE:
<223> OTHER INFORMATION: Wise/SOST Peptides
<220> FEATURE:
<221> NAME/KEY: misc_feature
<222> LOCATION: (4)..(4)
<223> OTHER INFORMATION: Xaa can be any naturally occurring amino acid

<400> SEQUENCE: 78

Asp Thr Val Xaa Asp Arg Ile Glu Val Cys Arg
1               5                   10

<210> SEQ ID NO 79
<211> LENGTH: 11
<212> TYPE: PRT
<213> ORGANISM: Artificial
<220> FEATURE:
<223> OTHER INFORMATION: Wise/SOST Peptides

<400> SEQUENCE: 79

Asp Ala Gly Thr Asp Arg Ile Glu Val Ala Asn
```

```
<210> SEQ ID NO 80
<211> LENGTH: 11
<212> TYPE: PRT
<213> ORGANISM: Artificial
<220> FEATURE:
<223> OTHER INFORMATION: Wise/SOST Peptides

<400> SEQUENCE: 80

Asp Ala Gly Thr Asp Arg Ile Glu Val Ala Asn
1               5                   10

<210> SEQ ID NO 81
<211> LENGTH: 11
<212> TYPE: PRT
<213> ORGANISM: Artificial
<220> FEATURE:
<223> OTHER INFORMATION: Wise/SOST Peptides

<400> SEQUENCE: 81

Asn Lys Ile Thr Gln Thr Ile Glu Ile Ile Arg
1               5                   10

<210> SEQ ID NO 82
<211> LENGTH: 11
<212> TYPE: PRT
<213> ORGANISM: Artificial
<220> FEATURE:
<223> OTHER INFORMATION: Wise/SOST Peptides

<400> SEQUENCE: 82

Asp Arg Gly Arg Ser Leu Ile Glu Gly Ser Asp
1               5                   10

<210> SEQ ID NO 83
<211> LENGTH: 546
<212> TYPE: DNA
<213> ORGANISM: Dog

<400> SEQUENCE: 83
atgcagctct ctcttgctct gtgtctcgtc tgcttgctgg tgcatgcagc cttccgtgca      60
gtggagggcc aggggtggca ggccttcaag aacgatgcca cagaaatcat ccccgagctg     120
ggcgagtacc ccgagcctcc accagagctg agaacaaca agaccatgaa ccggggcggag     180 aacggagggc ggccccctca ccatcccttt gagaccaaag acgcatccga gtacagctgc     240
cgcgagctgc acttcacccg ctacgtgacg gacgggccgt gccgcagcgc caagccggtc     300
accgagctgg tgtgctcggg ccagtgcggc ccgcgcgcc tgctgcccaa cgccatcggc     360
cgcggcaagt ggtggcgccc gagcgggccc gacttccgct gcatccccga ccgctaccgc     420
gcgcagcggg tgcagctgct gttgcgcctg gtggcctcgt gcaagtgcaa gcgactcacc     480
cgcttccaca accagtccga gctcaaggac ttcgggcccg aggccgcgcg gccgcagaag     540
ggccga                                                                546

<210> SEQ ID NO 84
<211> LENGTH: 642
<212> TYPE: DNA
<213> ORGANISM: Chimp

<400> SEQUENCE: 84
atgcagctcc cactggccct gtgtctcgtc tgcctgctgg tacacacagc cttccgtgta      60
```

```
gtggagggcc aggggtggca ggcgttcaag aatgatgcca cggaaatcat ccccgagctc      120
ggagagtacc ccgagcctcc accggagctg gagaacaaca agaccatgaa ccgggcggag      180
aacggagggc ggcctcccca ccaccccttt gagaccaaag acgtgtccga gtacagctgc      240
cgcgagctgc acttcacccg ctacgtgacc gatgggccgt gccgcagcgc caagccggtc      300
accgagctgg tgtgctccgg ccagtgcggc ccggcgcgcc tgctgcccaa cgccatcggc      360
cgcggcaagt ggtggcgacc tagtgggccc gacttccgct gcatcccga ccgctaccgc      420 gcgcagcgcg tgcagctgct gtgtccggt ggtgcggcgc cgcgcgcgcg caaggtgcgc      480
ctggtggcct cgtgcaagtg caagcgcctc acccgcttcc acaaccagtc ggagctcaag      540
gacttcggga ccgaggccgc tcggccgcag aagggccgga agccgcggcc ccgcgcccgg      600
agcgccaaag ccaaccaggc cgagctggag aacgcctact ag                       642
```

`<210>` SEQ ID NO 85
`<211>` LENGTH: 13
`<212>` TYPE: PRT
`<213>` ORGANISM: Chick

`<400>` SEQUENCE: 85

```
Ser Asn Asn Asn Thr Met Asn Gln Ala Lys Gly Gly Arg
1               5                   10
```

`<210>` SEQ ID NO 86
`<211>` LENGTH: 15
`<212>` TYPE: PRT
`<213>` ORGANISM: Chick

`<400>` SEQUENCE: 86

```
Ala Pro Asp Pro Asn Asp Val Ser Asp Phe Ser Cys Arg Glu Met
1               5                   10                  15
```

`<210>` SEQ ID NO 87
`<211>` LENGTH: 27
`<212>` TYPE: PRT
`<213>` ORGANISM: Chick

`<400>` SEQUENCE: 87

```
Arg Glu Met Arg Ile Thr Arg Tyr Val Thr Glu Gly Pro Cys Arg Ser
1               5                   10                  15

Leu Lys Pro Val Lys Glu Leu Val Cys Ser Gly
            20                  25
```

`<210>` SEQ ID NO 88
`<211>` LENGTH: 641
`<212>` TYPE: DNA
`<213>` ORGANISM: Chick

`<400>` SEQUENCE: 88

```
atgcagatct cctgggctgt gtgctctgtc tgcgtcctca tccaaatcgc atcccgggca       60
ctggagggtg gcaagtgttc aaaaatgatg cgacagaaat catccccgag atcaccgaaa      120
acacagagac cccaatggag cagatttaca gcaacaacaa cacgatgaac caggcaaagc      180 acggggaag gcacatacag caagctccgg accctaatga tgtctccgac ttcagctgca      240
gagagatgcg catcacccgc tacgtgacgg aggggccgtg ccgcagcctg aagcccgtga      300
aggagctggt gtgctcgggg cagtgcgtcc atcccacct cctgcccaac tccatcggca      360
gagggaagtg gtgtgaggcag aactccccgg attaccgctg catccggct cacacccgca      420 cgcagcgcat ccagatggcg tgtcccgagg atgagactcg gacttacaaa ttccgagctg      480
```

```
tcacagcctg caaatgcaag cgctacactc ggtaccacaa ccagtccgag ctgaaggact    540
ttgggaagga gccctccagg cagcagaaga acaagaagtc gcgtctgtcc cgagccagga    600
gcagcaaacc gaaccagcac gagctggaaa acgcctatta g                        641

<210> SEQ ID NO 89
<211> LENGTH: 555
<212> TYPE: DNA
<213> ORGANISM: Fugu

<400> SEQUENCE: 89
tggaaggtgc tgaagaacga cgccacagag attttaccgg actaccggga gcggagtccg     60
cacgagccga tgacgcaggc ggcgaacagc agcagtaacg gcgggaaccg cgcgaagagc    120
ggcgggagaa gcacgagctc ggtgacctac agtgcctcgg agctgagctg cagggagctg    180
cgttccaccc gctacgtcac cgatggatct tgccgcagcg ccaaacccat caaggagctg    240
gtgtgctcgg gccagtgcct gccagcgcac ctcatgccca acaccatcgg ccgcggcaag    300
tggtggcgga gcaacacctc ggagtaccgc tgcatcccgg ctcactccag gaccaggagg    360
atccagctgc agtgccccaa cggcaacact cggacttaca aaatccgcat agtgacctcc    420
tgcaagtgta gcggttcag gctcaccac aaccagtcgg aggccaagga ggtcctgagg     480
aggcagcgga gcaagaagcg cacgtctcaa ggacggagca aaaacaacac gcctttgatt    540
gacaattcat actga                                                    555

<210> SEQ ID NO 90
<211> LENGTH: 618
<212> TYPE: DNA
<213> ORGANISM: Mouse
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t

<400> SEQUENCE: 90
atgcttcctc ctgccattca tctctctctc attcccctgc tctgcatcct gatgagaaac     60
tgtttggctt ttaaaaatga tgccacagaa atcctttatt cacatgtggt taaacctgtc    120
ccggcacacc ccagcagcaa cagcaccctg aatcaagcca ggaatggagg caggcatttc    180
agtagcactg gactggatcg aaacagtcga gttcaagtgg gctgcaggga actgcggtcc    240
accaaataca tttcggacgg ccagtgcacc agcatcagcc ctntgaagga gctggtgtgc    300
gcgggcgagt gcttgcccct gccggtgctt cccaactgga tcggaggagg ctatggaaca    360
aagtactgga gccggaggag ctntcaggag tggcggtgtg tcaacgacaa gacgcgcacc    420
cagaggatcc agctgcagtg tcaggacggc agcacgcgca cctacaaaat caccgtggtc    480
acggcgtgca gtgcaagag gtacacccgt cagcacaacg agtccagcca caactttgaa    540
agcgtgtcgc ccgccaagcc cgcccagcac cacagagagc ggaagagagc cagcaaatcc    600
agcaagcaca gtctgagc                                                 618

<210> SEQ ID NO 91
<211> LENGTH: 14
<212> TYPE: PRT
<213> ORGANISM: Mouse
```

```
<400> SEQUENCE: 91

Ser Ser Asn Ser Thr Leu Asn Gln Ala Arg Asn Gly Gly Arg
1               5                   10

<210> SEQ ID NO 92
<211> LENGTH: 621
<212> TYPE: DNA
<213> ORGANISM: Human

<400> SEQUENCE: 92
atgcttcctc ctgccattca tctctctctc attcccctgc tctgcatcct gatgaaaaac      60
tgtttggctt ttaaaaatga tgccacagaa atcctttatt cacatgtggt taaacctgtt     120
tcagcacacc ccagcagcaa cagcaccttg aatcaagcca ggaatggagg caggcacttc     180
agtagcacgg gactggatcg aaatagtcga gttcaagtgg gctgcaggga actgcggtcc     240
accaaataca tctcggatgg ccagtgcacc agcatcagcc ctctgaagga gctggtgtgc     300
gcgggtgagt gcttgcccct gccagtgctt cccaactgga tcggaggagg ctacggaaca     360
aagtactgga gccggagggg ctcccaggag tggcggtgtg tcaacgacaa gacgcgcacc     420
cagagaatcc agctgcagtg tcaggacggc agcacacgca cctacaaaat caccgtggtc     480
acagcgtgca gtgcaagag gtacacccgg cagcacaacg agtccagcca caactttgaa      540
agcgtgtctc ccgccaagcc cgcccagcac acagagagc ggaagagagc cagcaaatcc      600
agcaagcaca gtctgagcta g                                               621

<210> SEQ ID NO 93
<211> LENGTH: 15
<212> TYPE: PRT
<213> ORGANISM: Human

<400> SEQUENCE: 93

Pro Ser Ser Asn Ser Thr Leu Asn Gln Ala Arg Asn Gly Gly Arg
1               5                   10                  15

<210> SEQ ID NO 94
<211> LENGTH: 642
<212> TYPE: DNA
<213> ORGANISM: Xenopus Leavis

<400> SEQUENCE: 94
atggttgtct caaggctcca gtgctgcatg ctctaccttg cgtgtattct catagaaagc      60
tgcgtgtctt ttaagaatga cgctacagaa atcctgtatt cccacgtgga taaacatatc     120
caagatagtg caaacagcag cacctgaat caggctagaa atggaggaag aaatgctgca      180
aactctgcac tggacagaac aaatcaccat caggttggat gcagagagct gagatctacc     240
aagtacatct cggatggaca gtgcaccagt atccagcctt tgaaagaact ggtctgtgct     300
ggagagtgtc ttcctctttc tattttggcc cactggatcg ggggtggcta cgggctgaaa     360
tattggagtc gaagaagttc ccaggaatgg agatgtgtca atgacaagac ccgcactcag     420
cgtatccagt tacagtgtga ggatggcact actagaaacct acaaagtcac agtggttact    480
tcctgcaagt gcaagagata caccagacag cacaatgaat ccagccataa ctaccaagga     540
gcttctccca ttaaaccgt tcactctcac caacatcatc actccaccaa caaccgtgat      600
aagaaaagac taatcaagat gtccaagcac attcctagct ag                        642

<210> SEQ ID NO 95
<211> LENGTH: 14
```

<212> TYPE: PRT
<213> ORGANISM: Xenopus Leavis

<400> SEQUENCE: 95

Arg Ser Thr Lys Tyr Ile Ser Asp Gly Gln Cys Thr Ser Ile
1               5                   10

<210> SEQ ID NO 96
<211> LENGTH: 642
<212> TYPE: DNA
<213> ORGANISM: Xenopus tropicalis

<400> SEQUENCE: 96

```
atggtcgtct caaggctcca atgctgcatg ttatactttg catgcatttt catagaaagc      60
tgcatgtctt ttaagaacga tgccacagaa atcctgtatt cccatgtgga taaaaacatc     120
caagagagtg ccaacagcag tgccctgaac caggctagga atggaggaag acacacggct     180
aactctgcca tggacaggac aaatccccat caagttggat gcaggagct gagatctaca      240
aagtacatct cagatgggca gtgcaccagt atccagcctt gaaagaact ggtctgtgct      300
ggagagtgtc ttcctcttcc tattttgccc aactggatcg gggtggcta tgggctgaag      360
tactggagtc ggagaagctc tcaggaatgg agatgtgtca atgacaagac tcgcactcag     420
cgtatccagt gcagtgtga ggatggcacg actagaacct acaaagtcac ggtggtaact      480
tcctgcaagt gcagaggta caccaggcag cacaacgaat ccagccataa ctacgaagga      540
gcttctccaa tgaaacccat tcactctctc aacatcatc actcccacca caaccgtgat      600
aagaaaagac taatcaagat gtccaagcac attcctagct ag                        642
```

<210> SEQ ID NO 97
<211> LENGTH: 621
<212> TYPE: DNA
<213> ORGANISM: Chick

<400> SEQUENCE: 97

```
atgcttctct ccgccattca cttctacggc ttactcctag cttgcacctt cacgagaagc      60
tactcggctt tcaagaacga tgccactgag atactttatt cccacgtcgt taaacctgcc     120
cctgcgagcc cgagcagcaa cagcacgttg aaccaagcca ggaacggagg gaggcactac     180
gccggcacgg gctccgaccg taacaatcgc gttcaagttg gctgccggga actgcgatct     240
accaagtaca tctcagacgg ccagtgcacc agcatcaatc ccctgaagga gctggtgtgt     300
gctggcgaat gcctcccctt gccgctcctg cccaactgga ttggaggagg ttatggaacc     360
aagtactgga gcagacggag ctcgcaagag tggagatgtg tcaatgacaa aactcgcacc     420
cagaggatcc agctgcagtg ccaggatgga agtataagaa cctacaaaat aactgtggtc     480
acggcctgca gtgcaagcg ataccaccagg cagcacaacg agtccagcca caactttgag     540
ggaacctctc aagcaaagcc tgtccagcat cacaaagaga gaaaaagagc cagtaaatcc     600
agcaaacata gtacaagtta g                                                621
```

<210> SEQ ID NO 98
<211> LENGTH: 15
<212> TYPE: PRT
<213> ORGANISM: Chick

<400> SEQUENCE: 98

Gly Ser Asp Arg Asn Asn Arg Val Gln Val Gly Cys Arg Glu Leu
1               5                   10                  15

<210> SEQ ID NO 99
<211> LENGTH: 621
<212> TYPE: DNA
<213> ORGANISM: Dog

<400> SEQUENCE: 99

| | | | | | |
|---|---|---|---|---|---|
| atgcttcctc | ctgccattca | tctctctctc | attcccctgc | tctgcatcct | gatgaaaaac | 60 |
| tgtttggctt | ttaaaaatga | tgccacagaa | atcctttatt | cacatgtggt | taaacctgtt | 120 |
| tcagcacacc | ccagcagcaa | cagcaccttg | aatcaagcca | ggaatggagg | caggcacttc | 180 |
| agtagcacgg | gactggatcg | aaatagtcga | gttcaagtgg | gctgcaggga | actgcggtcc | 240 |
| accaaataca | tctcggatgg | ccagtgcacc | agcatcagcc | ctctgaagga | gctggtgtgc | 300 |
| gcgggtgagt | gcttgccctt | gccagtgctt | cccaactgga | tcggaggagg | ctacggaaca | 360 |
| aagtactgga | gccggagggg | ctcccaggag | tggcggtgtg | tcaacgacaa | gacgcgcacc | 420 |
| cagagaatcc | agctgcagtg | tcaggacggc | agcacacgca | cctacaaaat | caccgtggtc | 480 |
| acagcgtgca | agtgcaagag | gtacacccgg | cagcacaacg | agtccagcca | caactttgaa | 540 |
| agcgtgtctc | ccgccaagcc | cgcccagcac | acagagagc | ggaagagagc | cagcaaatcc | 600 |
| agcaagcaca | gtctgagcta | g | | | | 621 |

<210> SEQ ID NO 100
<211> LENGTH: 625
<212> TYPE: DNA
<213> ORGANISM: Rat

<400> SEQUENCE: 100

| | | | | | |
|---|---|---|---|---|---|
| atgcttcctc | ctgccattca | tctctctctc | attcccctgc | tctgcatcct | gatgaaaaac | 60 |
| tgtttggctt | ttaaaaatga | tgccacagaa | atcctttatt | cacatgtggt | taaacctgtt | 120 |
| tcagcacacc | ccagcagcaa | cagcaccttg | aatcaagcca | ggaatggagg | caggcacttc | 180 |
| agtagcacgg | gactggatcg | aaatagtcga | gttcaagtgg | gctgcaggga | actgcggtcc | 240 |
| accaaataca | tctcggatgg | ccagtgcacc | agcatcagcc | ctctgaagga | gctggtgtgc | 300 |
| gcgggtgagt | gcttgccctt | gccagtgctt | cccaactgga | tcggaggagg | ctacggaaca | 360 |
| aagtactgga | gccggaggag | ctcccaggag | tggcggtgtg | tcaacgacaa | gacgcgcacc | 420 |
| cagagaatcc | agctgcagtg | tcaggacggc | agcacacgca | cctacaaaat | caccgtggtc | 480 |
| acagcgtgca | agtgcaagag | gtacacccgg | cagcacaacg | agtccagcca | caactttgaa | 540 |
| agcgtgtctc | ccgccaagcc | cgcccagcac | acagagagc | ggaagagagc | cagcaaatcc | 600 |
| agcaagcaca | gtctgagcta | gagct | | | | 625 |

<210> SEQ ID NO 101
<211> LENGTH: 14
<212> TYPE: PRT
<213> ORGANISM: Zebrafish

<400> SEQUENCE: 101

Thr His Asp Arg Glu Arg Ile Pro Val Gly Cys Arg Glu Leu
1               5                   10

<210> SEQ ID NO 102
<211> LENGTH: 608
<212> TYPE: DNA
<213> ORGANISM: Zebrafish

<400> SEQUENCE: 102

-continued

```
cagagttgaa gcacatctct ccattggccg tgggtcatta cgcatcgcca tgtatataaa    60
cgcaccagag tcgtgcaatt tcatggtttt attttgcttt ttaataagga gtggtttgac   120
tttgaagaac gatgctacgg agattttcta ctcgcatgtg gtcagtcccg ttcaggatgc   180
gcagagcaac gcgtctctca accgcgcgcg ctccggagga gaggcttca gcacgcacga    240
cagagaacga atcccagtag gctgcagaga gctccgatcc accaagtaca tctcagatgg   300
ccagtgcacc agcataaacc ctgtgaaaga gctggtgtgc acaggacagt gcctccccgc   360
tcagatgctg cccaattgga ttggaggata cggcaagaag tcctggaacc gccggaacag   420
tcaggaatgg cgctgtgtaa atgacaagac ccgaactcag cggattcagc tccagtgcca   480
ggatggcagc accaggacct acaagatcac agtggtgacc tcctgcaaat gcaaacgata   540
ctcgcggcaa cacaatgaat caggagttaa gtctgaggga tactctcata gccagatcaa   600
aaaacaga                                                            608
```

<210> SEQ ID NO 103
<211> LENGTH: 12
<212> TYPE: PRT
<213> ORGANISM: Fugu

<400> SEQUENCE: 103

Thr Tyr Ser Ala Ser Glu Leu Ser Cys Arg Glu Leu
1               5                   10

<210> SEQ ID NO 104
<211> LENGTH: 576
<212> TYPE: DNA
<213> ORGANISM: Fugu

<400> SEQUENCE: 104

```
tgctgcaccg ccgcgcgcgg atggaaggtg ctgaagaacg acgccacaga gattttaccg    60
gactaccggg agcggagtcc gcacgagccg atgacgcagg cggcgaacag cagcagtaac   120
ggcgggaacc gcgcgaagag cggcgggaga agcacgagct cggtgaccta cagtgcctcg   180
gagctgagct gcagggagct gcgttccacc cgctacgtca ccgatggatc ttgccgcagc   240
gccaaaccca tcaaggagct ggtgtgctcg ggccagtgcc tgccagcgca cctcatgccc   300
aacaccatcg gccgcggcaa gtggtggcgg agcaacacct cggagtaccg ctgcatcccg   360
gctcactcca ggaccaggag gatccagctg cagtgcccca acggcaacac tcggacttac   420
aaaatccgca tagtgaccta ctgcaagtgt aagcggttca gggctcacca caaccagtcg   480
gaggccaagg aggtcctgag gaggcagcgg agcaagaagc gcacgtctca aggacggagc   540
aaaaacaaca cgcctttgat tgacaattca tactga                             576
```

<210> SEQ ID NO 105
<211> LENGTH: 16
<212> TYPE: PRT
<213> ORGANISM: Pan troglodytes chimp

<400> SEQUENCE: 105

His Pro Ser Ser Asn Ser Thr Leu Asn Gln Ala Arg Asn Gly Gly Arg
1               5                   10                  15

<210> SEQ ID NO 106
<211> LENGTH: 618
<212> TYPE: DNA
<213> ORGANISM: Pan troglodytes chimp

<400> SEQUENCE: 106

```
atgcttcctc ctgccattca tttctatctc cttccccttg catgcatcct aatgaaaagc    60
tgtttggctt ttaaaaatga tgccacagaa atcctttatt cacatgtggt taaacctgtt   120
ccagcacacc ccagcagcaa cagcacgttg aatcaagcca gaaatggagg caggcatttc   180
agtaacactg gactggatcg gaacactcgg gttcaagtgg gttgccggga actgcgttcc   240
accaaataca tctctgatgg ccagtgcacc agcatcagcc ctctgaagga gctggtgtgt   300
gctggtgagt gcttgcccct gccagtgctc cctaactgga ttggaggagg ctatggaaca   360
aagtactgga gcaggaggag ctcccaggag tggcggtgtg tcaatgacaa aacccgtacc   420
cagagaatcc agctgcagtg ccaagatggc agcacacgca cctacaaaat cacagtagtc   480
actgcctgca gtgcaagag  gtacacccgg cagcacaacg agtccagtca aactttgag    540 agcatgtcac ctgccaagcc agtccagcat cacagagagc ggaaaagagc cagcaaatcc   600
agcaagcaca gcatgagt                                                 618
```

<210> SEQ ID NO 107
<211> LENGTH: 633
<212> TYPE: DNA
<213> ORGANISM: Tetradon fish

<400> SEQUENCE: 107

```
atgcaggtgt ctctggtcct cctcgtgtcc agctcggcgc tcgtgctgct gcagggatgc    60
tgcgccgccg cgcgcggctg gaaggcgctg aagaacgacg ccaccgaggt tttagcggac   120
gaccgcgagc ggagcccgca cgagcccgcc gcgcacgcgg ccaacgccag cagtaacgcg   180
ggaaaccggg cgaagagcgg cgcgaggagc acgagcacgg tgtcctacag tgcctcggag   240
ctaagctgca gggagctgcg ctccacccgt tacgtcaccg atgggtcctg ccgcagcgcc   300
aaacccatca agagctggt gtgctcgggc cagtgcctgc cggcgcacct catgcccaac    360
accattggcc gggccaagtg gtggcggagc agcacctcgg agtaccgctg cgtcccggct   420
cactccaggc ccaggaggat ccagctgcgc tgccccaacg gcaacactcg gacttacaaa   480
atccgcacgg tgacctcctg caagtgcaag aggttccggg ctcaccacaa ccagtcggag   540
gccaaggagg tcccgaggag gcaacgcacc aagaagcggc catcccgagg ccgcagcaag   600
aaccccacgc ctttgattga caattcctac tga                                633
```

<210> SEQ ID NO 108
<211> LENGTH: 621
<212> TYPE: DNA
<213> ORGANISM: Pongo pygmaeus

<400> SEQUENCE: 108

```
atgcttcctc ccgccattca tttctatctc cttccccttg catgcatcct aatgaaaagc    60
tgtttggctt ttaaaaatga tgccacagaa atcctttatt cacatgtggt taaacctgtt   120
ccagcacacc ccagcagcaa cagcacgttg aatcaagcca gaaatggagg caggcatttc   180
agtaacactg gactggatcg gaacactcgg gttcaagtgg gttgccggga actgcgttcc   240
accaaataca tctctgatgg ccagtgcacc agcatcagcc ctctgaagga gctggtgtgt   300
gctggcgagt gcttgcccct gtcagtgctc cctaactgga ttggaggagg ttatggaaca   360
aagtactgga gcaggaggag ctcccaggag tggcggtgcg tcaatgacaa aacccgtacc   420
cagagaatcc agctgcagtg ccaagatggc agcacacgca cctacaaaat cacagtagtc   480
actgcctgca gtgcaagag  gtacacccgg cagcacaacg agtccagtca aactttgag    540
```

```
agcatgtcac ctgccaagcc agtccagcat cacagagagc ggaaaagagc cagcaaatcc    600
agcaagcaca gcatgagtta g                                              621
```

<210> SEQ ID NO 109
<211> LENGTH: 15
<212> TYPE: PRT
<213> ORGANISM: Artificial
<220> FEATURE:
<223> OTHER INFORMATION: LRP 5/6 Peptides

<400> SEQUENCE: 109

Leu Phe Ala Asn Arg Arg Asp Val Arg Leu Val Asp Ala Gly Gly
1               5                   10                  15

<210> SEQ ID NO 110
<211> LENGTH: 8
<212> TYPE: PRT
<213> ORGANISM: Artificial
<220> FEATURE:
<223> OTHER INFORMATION: LTRP 5/6 Peptides

<400> SEQUENCE: 110

Tyr Trp Thr Asp Val Ser Glu Glu
1               5

<210> SEQ ID NO 111
<211> LENGTH: 19
<212> TYPE: PRT
<213> ORGANISM: Artificial
<220> FEATURE:
<223> OTHER INFORMATION: LRP 5/6 Peptides

<400> SEQUENCE: 111

Lys Leu Tyr Trp Thr Asp Ser Glu Thr Asn Arg Ile Glu Val Ala Asn
1               5                   10                  15

Leu Asn Gly

<210> SEQ ID NO 112
<211> LENGTH: 7
<212> TYPE: PRT
<213> ORGANISM: Artificial
<220> FEATURE:
<223> OTHER INFORMATION: LRP 5/6 Peptides

<400> SEQUENCE: 112

Leu Phe Trp Gln Asp Leu Asp
1               5

<210> SEQ ID NO 113
<211> LENGTH: 23
<212> TYPE: PRT
<213> ORGANISM: Artificial
<220> FEATURE:
<223> OTHER INFORMATION: LRP 5/6 Peptides

<400> SEQUENCE: 113

Thr Asp Trp Gly Glu Thr Pro Arg Ile Glu Arg Ala Gly Met Asp Gly
1               5                   10                  15

Ser Thr Arg Lys Ile Ile Val
            20

<210> SEQ ID NO 114
<211> LENGTH: 11
<212> TYPE: PRT
<213> ORGANISM: Artificial

```
<220> FEATURE:
<223> OTHER INFORMATION: LRP 5/6 Peptides

<400> SEQUENCE: 114

His Ala Cys Asn Lys Arg Thr Gly Gly Lys Arg
1               5                   10

<210> SEQ ID NO 115
<211> LENGTH: 15
<212> TYPE: PRT
<213> ORGANISM: Artificial
<220> FEATURE:
<223> OTHER INFORMATION: LRP 5/6 Peptides

<400> SEQUENCE: 115

Thr Gly Val Gln Leu Gln Asp Asn Gly Arg Thr Cys Lys Ala Gly
1               5                   10                  15

<210> SEQ ID NO 116
<211> LENGTH: 19
<212> TYPE: PRT
<213> ORGANISM: Artificial
<220> FEATURE:
<223> OTHER INFORMATION: LRP 5/6 Peptides

<400> SEQUENCE: 116

Glu Val Leu Leu Leu Ala Arg Arg Thr Asp Leu Arg Arg Ile Ser Leu
1               5                   10                  15

Asp Thr Pro

<210> SEQ ID NO 117
<211> LENGTH: 14
<212> TYPE: PRT
<213> ORGANISM: Artificial
<220> FEATURE:
<223> OTHER INFORMATION: LRP 5/6 Peptides

<400> SEQUENCE: 117

Tyr Trp Thr Asp Asp Glu Val Arg Ala Ile Arg Arg Ala Tyr
1               5                   10

<210> SEQ ID NO 118
<211> LENGTH: 10
<212> TYPE: PRT
<213> ORGANISM: Artificial
<220> FEATURE:
<223> OTHER INFORMATION: LRP 5/6 Peptides

<400> SEQUENCE: 118

Val Asn Thr Glu Ile Asn Asp Pro Asp Gly
1               5                   10

<210> SEQ ID NO 119
<211> LENGTH: 29
<212> TYPE: PRT
<213> ORGANISM: Artificial
<220> FEATURE:
<223> OTHER INFORMATION: LRP 5/6 Peptides

<400> SEQUENCE: 119

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25
```

-continued

<210> SEQ ID NO 120
<211> LENGTH: 20
<212> TYPE: PRT
<213> ORGANISM: LRP 5/6 Peptides

<400> SEQUENCE: 120

Thr Asp Trp Gln Arg Arg Ser Ile Glu Arg Val His Lys Val Lys Ala
1               5                   10                  15

Ser Arg Asp Val
            20

<210> SEQ ID NO 121
<211> LENGTH: 11
<212> TYPE: PRT
<213> ORGANISM: Artificial
<220> FEATURE:
<223> OTHER INFORMATION: LRP 5/6 Peptides

<400> SEQUENCE: 121

Asn Val Asp Gly Thr Lys Arg Arg Thr Leu Leu
1               5                   10

<210> SEQ ID NO 122
<211> LENGTH: 109
<212> TYPE: PRT
<213> ORGANISM: Artificial
<220> FEATURE:
<223> OTHER INFORMATION: LRP 5/6 Peptides

<400> SEQUENCE: 122

Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro Val Thr Glu Leu Val Cys Ser Gly
    50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

Arg Ala Gln Arg Val Gln Leu Leu Cys Pro Gly Gly Glu
            100                 105

<210> SEQ ID NO 123
<211> LENGTH: 56
<212> TYPE: PRT
<213> ORGANISM: Artificial
<220> FEATURE:
<223> OTHER INFORMATION: LRP 5/6 Peptides

<400> SEQUENCE: 123

Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro
    50                  55

```
<210> SEQ ID NO 124
<211> LENGTH: 53
<212> TYPE: PRT
<213> ORGANISM: Artificial
<220> FEATURE:
<223> OTHER INFORMATION: LRP 5/6 Peptides

<400> SEQUENCE: 124

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
            20                  25                  30

Phe Arg Cys Ile Pro Asp Arg Tyr Arg Ala Gln Arg Val Gln Leu Leu
        35                  40                  45

Cys Pro Gly Gly Glu
    50

<210> SEQ ID NO 125
<211> LENGTH: 24
<212> TYPE: PRT
<213> ORGANISM: Artificial
<220> FEATURE:
<223> OTHER INFORMATION: LRP 5/6 Peptides

<400> SEQUENCE: 125

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 126
<211> LENGTH: 13
<212> TYPE: PRT
<213> ORGANISM: Artificial
<220> FEATURE:
<223> OTHER INFORMATION: LRP 5/6 Peptides

<400> SEQUENCE: 126

Pro Lys Ile Glu Arg Ala Gly Met Asp Gly Ser Ser Arg
1               5                   10

<210> SEQ ID NO 127
<211> LENGTH: 18
<212> TYPE: PRT
<213> ORGANISM: Artificial
<220> FEATURE:
<223> OTHER INFORMATION: LRP 5/6 Peptides

<400> SEQUENCE: 127

Ala Ala Pro Leu Leu Leu Tyr Ala Asn Arg Arg Asp Leu Arg Leu Val
1               5                   10                  15

Asp Ala

<210> SEQ ID NO 128
<211> LENGTH: 17
<212> TYPE: PRT
<213> ORGANISM: Artificial
<220> FEATURE:
<223> OTHER INFORMATION: LRP 5/6 Peptides

<400> SEQUENCE: 128

Thr Ile Val Val Gly Gly Leu Glu Asp Ala Ala Ala Val Asp Phe Val
1               5                   10                  15
```

Phe

```
<210> SEQ ID NO 129
<211> LENGTH: 14
<212> TYPE: PRT
<213> ORGANISM: Artificial
<220> FEATURE:
<223> OTHER INFORMATION: LRP 5/6 Peptides

<400> SEQUENCE: 129
```

Gly Leu Ile Tyr Trp Ser Asp Val Ser Glu Glu Ala Ile Lys
1               5                   10

```
<210> SEQ ID NO 130
<211> LENGTH: 40
<212> TYPE: PRT
<213> ORGANISM: Artificial
<220> FEATURE:
<223> OTHER INFORMATION: LRP 5/6 Peptides

<400> SEQUENCE: 130
```

Ser Val Gln Asn Val Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
                20                  25                  30

Asn Arg Ile Glu Val Ser Asn Leu
        35                  40

```
<210> SEQ ID NO 131
<211> LENGTH: 19
<212> TYPE: PRT
<213> ORGANISM: Artificial
<220> FEATURE:
<223> OTHER INFORMATION: LRP 5/6 Peptides

<400> SEQUENCE: 131
```

Gln Asn Val Val Val Ser Gly Leu Leu Ser Pro Asp Gly Leu Ala Cys
1               5                   10                  15

Asp Trp Leu

```
<210> SEQ ID NO 132
<211> LENGTH: 20
<212> TYPE: PRT
<213> ORGANISM: Artificial
<220> FEATURE:
<223> OTHER INFORMATION: LRP 5/6 Peptides

<400> SEQUENCE: 132
```

Lys Leu Tyr Trp Thr Asp Ser Glu Thr Asn Arg Ile Glu Val Ser Asn
1               5                   10                  15

Leu Asp Gly Ser
            20

```
<210> SEQ ID NO 133
<211> LENGTH: 19
<212> TYPE: PRT
<213> ORGANISM: Artificial
<220> FEATURE:
<223> OTHER INFORMATION: LRP 5/6 Peptides

<400> SEQUENCE: 133
```

Arg Lys Val Leu Phe Trp Gln Glu Leu Asp Gln Pro Arg Ala Ile Ala
1               5                   10                  15

Leu Asp Pro

```
<210> SEQ ID NO 134
<211> LENGTH: 20
<212> TYPE: PRT
<213> ORGANISM: Artificial
<220> FEATURE:
<223> OTHER INFORMATION: LRP 5/6 Peptides

<400> SEQUENCE: 134

Met Tyr Trp Thr Asp Trp Gly Glu Val Pro Lys Ile Glu Arg Ala Gly
1               5                   10                  15

Met Asp Gly Ser
            20

<210> SEQ ID NO 135
<211> LENGTH: 8
<212> TYPE: PRT
<213> ORGANISM: Artificial
<220> FEATURE:
<223> OTHER INFORMATION: LRP 5/6 Peptides

<400> SEQUENCE: 135

Ile Tyr Trp Pro Asn Gly Leu Thr
1               5

<210> SEQ ID NO 136
<211> LENGTH: 9
<212> TYPE: PRT
<213> ORGANISM: Artificial
<220> FEATURE:
<223> OTHER INFORMATION: LRP 5/6 Peptides

<400> SEQUENCE: 136

Lys Leu Tyr Trp Ala Asp Ala Lys Leu
1               5

<210> SEQ ID NO 137
<211> LENGTH: 13
<212> TYPE: PRT
<213> ORGANISM: Artificial
<220> FEATURE:
<223> OTHER INFORMATION: LRP 5/6 Peptides

<400> SEQUENCE: 137

Phe Ile His Lys Ser Asn Leu Asp Gly Thr Asn Arg Gln
1               5                   10

<210> SEQ ID NO 138
<211> LENGTH: 14
<212> TYPE: PRT
<213> ORGANISM: Artificial
<220> FEATURE:
<223> OTHER INFORMATION: LRP 5/6 Peptides

<400> SEQUENCE: 138

Val Val Lys Gly Ser Leu Pro His Pro Phe Ala Leu Thr Leu
1               5                   10

<210> SEQ ID NO 139
<211> LENGTH: 21
<212> TYPE: PRT
<213> ORGANISM: Artificial
<220> FEATURE:
<223> OTHER INFORMATION: LRP 5/6 Peptides

<400> SEQUENCE: 139
```

```
Asp Thr Leu Tyr Trp Thr Asp Trp Asn Thr His Ser Ile Leu Ala Cys
1               5                   10                  15

Asn Lys Tyr Thr Gly
            20

<210> SEQ ID NO 140
<211> LENGTH: 13
<212> TYPE: PRT
<213> ORGANISM: Artificial
<220> FEATURE:
<223> OTHER INFORMATION: LRP 5/6 Peptides

<400> SEQUENCE: 140

Arg Glu Ile His Ser Asn Ile Phe Ser Pro Met Asp Ile
1               5                   10

<210> SEQ ID NO 141
<211> LENGTH: 21
<212> TYPE: PRT
<213> ORGANISM: Artificial
<220> FEATURE:
<223> OTHER INFORMATION: LRP 5/6 Peptides

<400> SEQUENCE: 141

Ser Asp Arg Asn Asn Arg Val Gln Val Gly Cys Arg Glu Leu Arg Ser
1               5                   10                  15

Thr Lys Tyr Ile Ser
            20

<210> SEQ ID NO 142
<211> LENGTH: 21
<212> TYPE: PRT
<213> ORGANISM: Artificial
<220> FEATURE:
<223> OTHER INFORMATION: LRP 5/6 Peptides

<400> SEQUENCE: 142

Pro Glu Pro Pro Pro Glu Leu Glu Asn Asn Lys Thr Met Asn Arg Ala
1               5                   10                  15

Glu Asn Gly Gly Arg
            20

<210> SEQ ID NO 143
<211> LENGTH: 32
<212> TYPE: PRT
<213> ORGANISM: Artificial
<220> FEATURE:
<223> OTHER INFORMATION: LRP 5/6 Peptides

<400> SEQUENCE: 143

Asn Gly Gly Arg Pro Pro His His Pro Phe Glu Thr Lys Asp Val Ser
1               5                   10                  15

Glu Tyr Ser Cys Arg Glu Leu His Phe Thr Tyr Val Thr Asp Gly
            20                  25                  30

<210> SEQ ID NO 144
<211> LENGTH: 8
<212> TYPE: PRT
<213> ORGANISM: Artificial
<220> FEATURE:
<223> OTHER INFORMATION: LRP 5/6 Peptides

<400> SEQUENCE: 144

Asn Asn Lys Thr Met Asn Arg Ala
1               5
```

```
<210> SEQ ID NO 145
<211> LENGTH: 5
<212> TYPE: PRT
<213> ORGANISM: Artificial
<220> FEATURE:
<223> OTHER INFORMATION: LRP 5/6 Peptides

<400> SEQUENCE: 145

Thr Met Asn Arg Ala
1               5

<210> SEQ ID NO 146
<211> LENGTH: 8
<212> TYPE: PRT
<213> ORGANISM: Artificial
<220> FEATURE:
<223> OTHER INFORMATION: LRP 5/6 Peptides

<400> SEQUENCE: 146

Gly Gly Arg Pro Pro His His Pro
1               5

<210> SEQ ID NO 147
<211> LENGTH: 9
<212> TYPE: PRT
<213> ORGANISM: Artificial
<220> FEATURE:
<223> OTHER INFORMATION: LRP 5/6 Peptides

<400> SEQUENCE: 147

His His Pro Phe Glu Thr Lys Asp Val
1               5

<210> SEQ ID NO 148
<211> LENGTH: 10
<212> TYPE: PRT
<213> ORGANISM: Artificial
<220> FEATURE:
<223> OTHER INFORMATION: LRP 5/6 Peptides

<400> SEQUENCE: 148

Asp Val Ser Glu Tyr Ser Cys Arg Glu Leu
1               5                   10

<210> SEQ ID NO 149
<211> LENGTH: 17
<212> TYPE: PRT
<213> ORGANISM: Artificial
<220> FEATURE:
<223> OTHER INFORMATION: LRP 5/6 Peptides

<400> SEQUENCE: 149

Cys Arg Glu Leu His Phe Thr Arg Tyr Val Thr Asp Gly Pro Cys Arg
1               5                   10                  15

Ser

<210> SEQ ID NO 150
<211> LENGTH: 7
<212> TYPE: PRT
<213> ORGANISM: Artificial
<220> FEATURE:
<223> OTHER INFORMATION: LRP 5/6 Peptides

<400> SEQUENCE: 150

Thr Arg Tyr Val Thr Asp Gly
```

```
<210> SEQ ID NO 151
<211> LENGTH: 5
<212> TYPE: PRT
<213> ORGANISM: Artificial
<220> FEATURE:
<223> OTHER INFORMATION: LRP 5/6 Peptides

<400> SEQUENCE: 151

Tyr Val Thr Asp Gly
1               5

<210> SEQ ID NO 152
<211> LENGTH: 6
<212> TYPE: PRT
<213> ORGANISM: Artificial
<220> FEATURE:
<223> OTHER INFORMATION: LRP 5/6 Peptides

<400> SEQUENCE: 152

Asp Gly Pro Cys Arg Ser
1               5

<210> SEQ ID NO 153
<211> LENGTH: 12
<212> TYPE: PRT
<213> ORGANISM: Artificial
<220> FEATURE:
<223> OTHER INFORMATION: LRP 5/6 Peptides

<400> SEQUENCE: 153

Leu Pro Asn Ala Ile Gly Arg Gly Lys Trp Trp Arg
1               5                   10

<210> SEQ ID NO 154
<211> LENGTH: 8
<212> TYPE: PRT
<213> ORGANISM: Artificial
<220> FEATURE:
<223> OTHER INFORMATION: LRP 5/6 Peptides

<400> SEQUENCE: 154

Pro Asn Trp Ile Gly Gly Gly Tyr
1               5

<210> SEQ ID NO 155
<211> LENGTH: 11
<212> TYPE: PRT
<213> ORGANISM: Artificial
<220> FEATURE:
<223> OTHER INFORMATION: LRP 5/6 Peptides

<400> SEQUENCE: 155

Thr Leu Asn Gln Ala Arg Asn Gly Gly Arg His
1               5                   10

<210> SEQ ID NO 156
<211> LENGTH: 5
<212> TYPE: PRT
<213> ORGANISM: Artificial
<220> FEATURE:
<223> OTHER INFORMATION: LRP 5/6 Peptides

<400> SEQUENCE: 156

Gly Leu Asp Arg Asn
1               5
```

```
<210> SEQ ID NO 157
<211> LENGTH: 13
<212> TYPE: PRT
<213> ORGANISM: Artificial
<220> FEATURE:
<223> OTHER INFORMATION: LRP 5/6 Peptides

<400> SEQUENCE: 157

Cys Arg Glu Leu Arg Ser Thr Lys Tyr Ile Ser Asp Gly
1               5                   10

<210> SEQ ID NO 158
<211> LENGTH: 15
<212> TYPE: PRT
<213> ORGANISM: Artificial
<220> FEATURE:
<223> OTHER INFORMATION: LRP 5/6 Peptides

<400> SEQUENCE: 158

Leu Phe Ala Asn Arg Arg Asp Val Arg Leu Val Asp Ala Gly Gly
1               5                   10                  15

<210> SEQ ID NO 159
<211> LENGTH: 8
<212> TYPE: PRT
<213> ORGANISM: Artificial
<220> FEATURE:
<223> OTHER INFORMATION: LRP 5/6 Peptides

<400> SEQUENCE: 159

Tyr Trp Thr Asp Val Ser Glu Glu
1               5

<210> SEQ ID NO 160
<211> LENGTH: 19
<212> TYPE: PRT
<213> ORGANISM: Artificial
<220> FEATURE:
<223> OTHER INFORMATION: LRP 5/6 Peptides

<400> SEQUENCE: 160

Lys Leu Tyr Trp Thr Asp Ser Glu Thr Asn Arg Ile Glu Val Ala Asn
1               5                   10                  15

Leu Asn Gly

<210> SEQ ID NO 161
<211> LENGTH: 7
<212> TYPE: PRT
<213> ORGANISM: Artificial
<220> FEATURE:
<223> OTHER INFORMATION: LRP 5/6 Peptides

<400> SEQUENCE: 161

Leu Phe Trp Gln Asp Leu Asp
1               5

<210> SEQ ID NO 162
<211> LENGTH: 23
<212> TYPE: PRT
<213> ORGANISM: Artificial
<220> FEATURE:
<223> OTHER INFORMATION: LRP 5/6 Peptides

<400> SEQUENCE: 162

Thr Asp Trp Gly Glu Thr Pro Arg Ile Glu Arg Ala Gly Met Asp Gly
```

```
                1               5                  10                 15

Ser Thr Arg Lys Ile Ile Val
            20

<210> SEQ ID NO 163
<211> LENGTH: 11
<212> TYPE: PRT
<213> ORGANISM: Artificial
<220> FEATURE:
<223> OTHER INFORMATION: LRP 5/6 Peptides

<400> SEQUENCE: 163

His Ala Cys Asn Lys Arg Thr Gly Gly Lys Arg
1               5                  10

<210> SEQ ID NO 164
<211> LENGTH: 15
<212> TYPE: PRT
<213> ORGANISM: Artificial
<220> FEATURE:
<223> OTHER INFORMATION: LRP 5/6 Peptides

<400> SEQUENCE: 164

Thr Gly Val Gln Leu Gln Asp Asn Gly Arg Thr Cys Lys Ala Gly
1               5                  10                  15

<210> SEQ ID NO 165
<211> LENGTH: 19
<212> TYPE: PRT
<213> ORGANISM: Artificial
<220> FEATURE:
<223> OTHER INFORMATION: LRP 5/6 Peptides

<400> SEQUENCE: 165

Glu Val Leu Leu Leu Ala Arg Arg Thr Asp Leu Arg Arg Ile Ser Leu
1               5                  10                  15

Asp Thr Pro

<210> SEQ ID NO 166
<211> LENGTH: 14
<212> TYPE: PRT
<213> ORGANISM: Artificial
<220> FEATURE:
<223> OTHER INFORMATION: LRP 5/6 Peptides

<400> SEQUENCE: 166

Tyr Trp Thr Asp Asp Glu Val Arg Ala Ile Arg Arg Ala Tyr
1               5                  10

<210> SEQ ID NO 167
<211> LENGTH: 10
<212> TYPE: PRT
<213> ORGANISM: Artificial
<220> FEATURE:
<223> OTHER INFORMATION: LRP 5/6 Peptides

<400> SEQUENCE: 167

Val Asn Thr Glu Ile Asn Asp Pro Asp Gly
1               5                  10

<210> SEQ ID NO 168
<211> LENGTH: 29
<212> TYPE: PRT
<213> ORGANISM: Artificial
<220> FEATURE:
<223> OTHER INFORMATION: LRP 5/6 Peptides
```

```
<400> SEQUENCE: 168

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25

<210> SEQ ID NO 169
<211> LENGTH: 20
<212> TYPE: PRT
<213> ORGANISM: Artificial
<220> FEATURE:
<223> OTHER INFORMATION: LRP 5/6 Peptides

<400> SEQUENCE: 169

Thr Asp Trp Gln Arg Arg Ser Ile Glu Arg Val His Lys Val Lys Ala
1               5                   10                  15

Ser Arg Asp Val
            20

<210> SEQ ID NO 170
<211> LENGTH: 11
<212> TYPE: PRT
<213> ORGANISM: Artificial
<220> FEATURE:
<223> OTHER INFORMATION: LRP 5/6 Peptides

<400> SEQUENCE: 170

Asn Val Asp Gly Thr Lys Arg Arg Thr Leu Leu
1               5                   10

<210> SEQ ID NO 171
<211> LENGTH: 109
<212> TYPE: PRT
<213> ORGANISM: Artificial
<220> FEATURE:
<223> OTHER INFORMATION: LRP 5/6 Peptides

<400> SEQUENCE: 171

Pro Glu Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro Val Thr Glu Leu Val Cys Ser Gly
    50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

Arg Ala Gln Arg Val Gln Leu Leu Cys Pro Gly Gly Glu
            100                 105

<210> SEQ ID NO 172
<211> LENGTH: 56
<212> TYPE: PRT
<213> ORGANISM: Artificial
<220> FEATURE:
<223> OTHER INFORMATION: LRP 5/6 Peptides

<400> SEQUENCE: 172
```

```
Pro Glu Pro Pro Glu Leu Glu Asn Asn Lys Thr Met Asn Arg Ala
1               5                   10                  15

Glu Asn Gly Gly Arg Pro His His Pro Phe Glu Thr Lys Asp Val
            20                  25                  30

Ser Glu Tyr Ser Cys Arg Glu Leu His Phe Thr Arg Tyr Val Thr Asp
            35                  40                  45

Gly Pro Cys Arg Ser Ala Lys Pro
    50                  55

<210> SEQ ID NO 173
<211> LENGTH: 53
<212> TYPE: PRT
<213> ORGANISM: Artificial
<220> FEATURE:
<223> OTHER INFORMATION: LRP 5/6 Peptides

<400> SEQUENCE: 173

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
            20                  25                  30

Phe Arg Cys Ile Pro Asp Arg Tyr Arg Ala Gln Arg Val Gln Leu Leu
            35                  40                  45

Cys Pro Gly Gly Glu
    50

<210> SEQ ID NO 174
<211> LENGTH: 18
<212> TYPE: PRT
<213> ORGANISM: Artificial
<220> FEATURE:
<223> OTHER INFORMATION: LRP 5/6 Peptides

<400> SEQUENCE: 174

Ala Ala Pro Leu Leu Leu Tyr Ala Asn Arg Arg Asp Leu Arg Leu Val
1               5                   10                  15

Asp Ala

<210> SEQ ID NO 175
<211> LENGTH: 17
<212> TYPE: PRT
<213> ORGANISM: Artificial
<220> FEATURE:
<223> OTHER INFORMATION: LRP 5/6 Peptides

<400> SEQUENCE: 175

Thr Ile Val Val Gly Gly Leu Glu Asp Ala Ala Ala Val Asp Phe Val
1               5                   10                  15

Phe

<210> SEQ ID NO 176
<211> LENGTH: 14
<212> TYPE: PRT
<213> ORGANISM: Artificial
<220> FEATURE:
<223> OTHER INFORMATION: LRP 5/6 Peptides

<400> SEQUENCE: 176

Gly Leu Ile Tyr Trp Ser Asp Val Ser Glu Glu Ala Ile Lys
1               5                   10

<210> SEQ ID NO 177
```

```
<211> LENGTH: 40
<212> TYPE: PRT
<213> ORGANISM: Artificial
<220> FEATURE:
<223> OTHER INFORMATION: LRP 5/6 Peptides

<400> SEQUENCE: 177

Ser Val Gln Asn Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
                20                  25                  30

Asn Arg Ile Glu Val Ser Asn Leu
        35                  40

<210> SEQ ID NO 178
<211> LENGTH: 19
<212> TYPE: PRT
<213> ORGANISM: Artificial
<220> FEATURE:
<223> OTHER INFORMATION: LRP 5/6 Peptides

<400> SEQUENCE: 178

Gln Asn Val Val Ser Gly Leu Leu Ser Pro Asp Gly Leu Ala Cys
1               5                   10                  15

Asp Trp Leu

<210> SEQ ID NO 179
<211> LENGTH: 20
<212> TYPE: PRT
<213> ORGANISM: Artificial
<220> FEATURE:
<223> OTHER INFORMATION: LRP 5/6 Peptides

<400> SEQUENCE: 179

Lys Leu Tyr Trp Thr Asp Ser Glu Thr Asn Arg Ile Glu Val Ser Asn
1               5                   10                  15

Leu Asp Gly Ser
            20

<210> SEQ ID NO 180
<211> LENGTH: 19
<212> TYPE: PRT
<213> ORGANISM: Artificial
<220> FEATURE:
<223> OTHER INFORMATION: LRP 5/6 Peptides

<400> SEQUENCE: 180

Arg Lys Val Leu Phe Trp Gln Glu Leu Asp Gln Pro Arg Ala Ile Ala
1               5                   10                  15

Leu Asp Pro

<210> SEQ ID NO 181
<211> LENGTH: 20
<212> TYPE: PRT
<213> ORGANISM: Artificial
<220> FEATURE:
<223> OTHER INFORMATION: LRP 5/6 Peptides

<400> SEQUENCE: 181

Met Tyr Trp Thr Asp Trp Gly Glu Val Pro Lys Ile Glu Arg Ala Gly
1               5                   10                  15

Met Asp Gly Ser
            20
```

```
<210> SEQ ID NO 182
<211> LENGTH: 8
<212> TYPE: PRT
<213> ORGANISM: Artificial
<220> FEATURE:
<223> OTHER INFORMATION: LRP 5/6 Peptides

<400> SEQUENCE: 182

Ile Tyr Trp Pro Asn Gly Leu Thr
1               5

<210> SEQ ID NO 183
<211> LENGTH: 9
<212> TYPE: PRT
<213> ORGANISM: Artificial
<220> FEATURE:
<223> OTHER INFORMATION: LRP 5/6 Peptides

<400> SEQUENCE: 183

Lys Leu Tyr Trp Ala Asp Ala Lys Leu
1               5

<210> SEQ ID NO 184
<211> LENGTH: 13
<212> TYPE: PRT
<213> ORGANISM: Artificial
<220> FEATURE:
<223> OTHER INFORMATION: LRP 5/6 Peptides

<400> SEQUENCE: 184

Phe Ile His Lys Ser Asn Leu Asp Gly Thr Asn Arg Gln
1               5                   10

<210> SEQ ID NO 185
<211> LENGTH: 14
<212> TYPE: PRT
<213> ORGANISM: Artificial
<220> FEATURE:
<223> OTHER INFORMATION: LRP 5/6 Peptides

<400> SEQUENCE: 185

Val Val Lys Gly Ser Leu Pro His Pro Phe Ala Leu Thr Leu
1               5                   10

<210> SEQ ID NO 186
<211> LENGTH: 21
<212> TYPE: PRT
<213> ORGANISM: Artificial
<220> FEATURE:
<223> OTHER INFORMATION: LRP 5/6 Peptides

<400> SEQUENCE: 186

Asp Thr Leu Tyr Trp Thr Asp Trp Asn Thr His Ser Ile Leu Ala Cys
1               5                   10                  15

Asn Lys Tyr Thr Gly
            20

<210> SEQ ID NO 187
<211> LENGTH: 13
<212> TYPE: PRT
<213> ORGANISM: Artificial
<220> FEATURE:
<223> OTHER INFORMATION: LRP 5/6 Peptides

<400> SEQUENCE: 187

Arg Glu Ile His Ser Asn Ile Phe Ser Pro Met Asp Ile
```

<210> SEQ ID NO 188
<211> LENGTH: 10
<212> TYPE: PRT
<213> ORGANISM: Artificial
<220> FEATURE:
<223> OTHER INFORMATION: LRP 5/6 Peptides

<400> SEQUENCE: 188

Asp Asn Gly Gly Cys Ser His Leu Cys Leu
1               5                   10

<210> SEQ ID NO 189
<211> LENGTH: 11
<212> TYPE: PRT
<213> ORGANISM: Artificial
<220> FEATURE:
<223> OTHER INFORMATION: LRP 5/6 Peptides

<400> SEQUENCE: 189

Pro Phe Tyr Gln Cys Ala Cys Pro Thr Gly Val
1               5                   10

<210> SEQ ID NO 190
<211> LENGTH: 25
<212> TYPE: PRT
<213> ORGANISM: Artificial
<220> FEATURE:
<223> OTHER INFORMATION: LRP 5/6 Peptides

<400> SEQUENCE: 190

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25

<210> SEQ ID NO 191
<211> LENGTH: 12
<212> TYPE: PRT
<213> ORGANISM: Artificial
<220> FEATURE:
<223> OTHER INFORMATION: LRP 5/6 Peptides

<400> SEQUENCE: 191

Asp Ile Arg His Ala Ile Ala Ile Asp Tyr Asp Pro
1               5                   10

<210> SEQ ID NO 192
<211> LENGTH: 16
<212> TYPE: PRT
<213> ORGANISM: Artificial
<220> FEATURE:
<223> OTHER INFORMATION: LRP 5/6 Peptides

<400> SEQUENCE: 192

Glu Gly Tyr Ile Tyr Trp Thr Asp Asp Glu Val Arg Ala Ile Arg Arg
1               5                   10                  15

<210> SEQ ID NO 193
<211> LENGTH: 31
<212> TYPE: PRT
<213> ORGANISM: Artificial
<220> FEATURE:
<223> OTHER INFORMATION: LRP 5/6 Peptides

<400> SEQUENCE: 193

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 194
<211> LENGTH: 15
<212> TYPE: PRT
<213> ORGANISM: Artificial
<220> FEATURE:
<223> OTHER INFORMATION: LRP 5/6 Peptides

<400> SEQUENCE: 194

Arg Lys Ile Leu Ile Ser Glu Asp Leu Glu Glu Pro Arg Ala Ile
1               5                   10                  15

<210> SEQ ID NO 195
<211> LENGTH: 8
<212> TYPE: PRT
<213> ORGANISM: Artificial
<220> FEATURE:
<223> OTHER INFORMATION: LRP 5/6 Peptides

<400> SEQUENCE: 195

Met Tyr Trp Thr Asp Trp Gly Glu
1               5

<210> SEQ ID NO 196
<211> LENGTH: 10
<212> TYPE: PRT
<213> ORGANISM: Artificial
<220> FEATURE:
<223> OTHER INFORMATION: LRP 5/6 Peptides

<400> SEQUENCE: 196

Pro Lys Ile Glu Arg Ala Ala Leu Asp Gly
1               5                   10

<210> SEQ ID NO 197
<211> LENGTH: 16
<212> TYPE: PRT
<213> ORGANISM: Artificial
<220> FEATURE:
<223> OTHER INFORMATION: LRP 5/6 Peptides

<400> SEQUENCE: 197

Val Leu Val Asn Thr Ser Leu Gly Trp Pro Asn Gly Leu Ala Leu Asp
1               5                   10                  15

<210> SEQ ID NO 198
<211> LENGTH: 12
<212> TYPE: PRT
<213> ORGANISM: Artificial
<220> FEATURE:
<223> OTHER INFORMATION: LRP 5/6 Peptides

<400> SEQUENCE: 198

Tyr Trp Gly Asp Ala Lys Thr Asp Lys Ile Glu Val
1               5                   10

<210> SEQ ID NO 199
<211> LENGTH: 32
<212> TYPE: PRT
<213> ORGANISM: Artificial
<220> FEATURE:
<223> OTHER INFORMATION: LRP 5/6 Peptides -continued

```
<400> SEQUENCE: 199

Glu Asp Lys Ile Pro His Ile Phe Gly Phe Thr Leu Leu Gly Asp Tyr
1               5                   10                  15

Val Tyr Trp Thr Asp Trp Gln Arg Arg Ser Ile Glu Arg Val His Lys
            20                  25                  30

<210> SEQ ID NO 200
<211> LENGTH: 24
<212> TYPE: PRT
<213> ORGANISM: Artificial
<220> FEATURE:
<223> OTHER INFORMATION: LRP 5/6 Peptides

<400> SEQUENCE: 200

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 201
<211> LENGTH: 13
<212> TYPE: PRT
<213> ORGANISM: Artificial
<220> FEATURE:
<223> OTHER INFORMATION: LRP 5/6 Peptides

<400> SEQUENCE: 201

Pro Lys Ile Glu Arg Ala Gly Met Asp Gly Ser Ser Arg
1               5                   10

<210> SEQ ID NO 202
<211> LENGTH: 10
<212> TYPE: PRT
<213> ORGANISM: Artificial
<220> FEATURE:
<223> OTHER INFORMATION: LRP 5/6 Peptides

<400> SEQUENCE: 202

Asp Asn Gly Gly Cys Ser His Leu Cys Leu
1               5                   10

<210> SEQ ID NO 203
<211> LENGTH: 11
<212> TYPE: PRT
<213> ORGANISM: Artificial
<220> FEATURE:
<223> OTHER INFORMATION: LRP 5/6 Peptides

<400> SEQUENCE: 203

Pro Phe Tyr Gln Cys Ala Cys Pro Thr Gly Val
1               5                   10

<210> SEQ ID NO 204
<211> LENGTH: 25
<212> TYPE: PRT
<213> ORGANISM: Artificial
<220> FEATURE:
<223> OTHER INFORMATION: LRP 5/6 Peptides

<400> SEQUENCE: 204

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25
```

```
<210> SEQ ID NO 205
<211> LENGTH: 12
<212> TYPE: PRT
<213> ORGANISM: Artificial
<220> FEATURE:
<223> OTHER INFORMATION: LRP 5/6 Peptides

<400> SEQUENCE: 205

Asp Ile Arg His Ala Ile Ala Ile Asp Tyr Asp Pro
1               5                   10

<210> SEQ ID NO 206
<211> LENGTH: 16
<212> TYPE: PRT
<213> ORGANISM: Artificial
<220> FEATURE:
<223> OTHER INFORMATION: LRP 5/6 Peptides

<400> SEQUENCE: 206

Glu Gly Tyr Ile Tyr Trp Thr Asp Asp Glu Val Arg Ala Ile Arg Arg
1               5                   10                  15

<210> SEQ ID NO 207
<211> LENGTH: 31
<212> TYPE: PRT
<213> ORGANISM: Artificial
<220> FEATURE:
<223> OTHER INFORMATION: LRP 5/6 Peptides

<400> SEQUENCE: 207

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 208
<211> LENGTH: 15
<212> TYPE: PRT
<213> ORGANISM: Artificial
<220> FEATURE:
<223> OTHER INFORMATION: LRP 5/6 Peptides

<400> SEQUENCE: 208

Arg Lys Ile Leu Ile Ser Glu Asp Leu Glu Glu Pro Arg Ala Ile
1               5                   10                  15

<210> SEQ ID NO 209
<211> LENGTH: 8
<212> TYPE: PRT
<213> ORGANISM: Artificial
<220> FEATURE:
<223> OTHER INFORMATION: LRP 5/6 Peptides

<400> SEQUENCE: 209

Met Tyr Trp Thr Asp Trp Gly Glu
1               5

<210> SEQ ID NO 210
<211> LENGTH: 10
<212> TYPE: PRT
<213> ORGANISM: Artificial
<220> FEATURE:
<223> OTHER INFORMATION: LRP 5/6 Peptides

<400> SEQUENCE: 210
```

```
Pro Lys Ile Glu Arg Ala Ala Leu Asp Gly
1               5                  10

<210> SEQ ID NO 211
<211> LENGTH: 16
<212> TYPE: PRT
<213> ORGANISM: Artificial
<220> FEATURE:
<223> OTHER INFORMATION: LRP 5/6 Peptides

<400> SEQUENCE: 211

Val Leu Val Asn Thr Ser Leu Gly Trp Pro Asn Gly Leu Ala Leu Asp
1               5                  10                  15

<210> SEQ ID NO 212
<211> LENGTH: 12
<212> TYPE: PRT
<213> ORGANISM: Artificial
<220> FEATURE:
<223> OTHER INFORMATION: LRP 5/6 Peptides

<400> SEQUENCE: 212

Tyr Trp Gly Asp Ala Lys Thr Asp Lys Ile Glu Val
1               5                  10

<210> SEQ ID NO 213
<211> LENGTH: 32
<212> TYPE: PRT
<213> ORGANISM: Artificial
<220> FEATURE:
<223> OTHER INFORMATION: LRP 5/6 Peptides

<400> SEQUENCE: 213

Glu Asp Lys Ile Pro His Ile Phe Gly Phe Thr Leu Leu Gly Asp Tyr
1               5                  10                  15

Val Tyr Trp Thr Asp Trp Gln Arg Arg Ser Ile Glu Arg Val His Lys
            20                  25                  30

<210> SEQ ID NO 214
<211> LENGTH: 21
<212> TYPE: PRT
<213> ORGANISM: Artificial
<220> FEATURE:
<223> OTHER INFORMATION: LRP 5/6 Peptides

<400> SEQUENCE: 214

Ser Asp Arg Asn Asn Arg Val Gln Val Gly Cys Arg Glu Leu Arg Ser
1               5                  10                  15

Thr Lys Tyr Ile Ser
            20

<210> SEQ ID NO 215
<211> LENGTH: 621
<212> TYPE: DNA
<213> ORGANISM: Human

<400> SEQUENCE: 215
atgcttcctc ctgccattca tctctctctc attccctgc  tctgcatcct gatgaaaaac      60
tgtttggctt ttaaaaatga tgccacagaa atcctttatt cacatgtggt taaacctgtt    120
tcagcacacc ccagcagcaa cagcaccttg aatcaagcca ggaatggagg caggcacttc    180
agtagcacgg gactggatcg aaatagtcga gttcaagtgg ctgcaggga actgcggtcc     240 accaaataca tctcggatgg ccagtgcacc agcatcagcc ctctgaagga gctggtgtgc    300
```

```
gcgggtgagt gcttgcccctt gccagtgctt cccaactgga tcggaggagg ctacggaaca    360
aagtactgga gccggagggg ctcccaggag tggcggtgtg tcaacgacaa gacgcgcacc    420
cagagaatcc agctgcagtg tcaggacggc agcacacgca cctacaaaat caccgtggtc    480
acagcgtgca agtgcaagag gtacacccgg cagcacaacg agtccagcca caactttgaa    540
agcgtgtctc ccgccaagcc cgcccagcac cacagagagc ggaagagagc cagcaaatcc    600
agcaagcaca gtctgagcta g                                              621

<210> SEQ ID NO 216
<211> LENGTH: 206
<212> TYPE: PRT
<213> ORGANISM: Mouse
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid

<400> SEQUENCE: 216

Met Leu Pro Pro Ala Ile His Leu Ser Leu Ile Pro Leu Leu Cys Ile
1               5                   10                  15

Leu Met Arg Asn Cys Leu Ala Phe Lys Asn Asp Ala Thr Glu Ile Leu
                20                  25                  30

Tyr Ser His Val Val Lys Pro Val Pro Ala His Pro Ser Ser Asn Ser
            35                  40                  45

Thr Leu Asn Gln Ala Arg Asn Gly Gly Arg His Phe Ser Ser Thr Gly
        50                  55                  60

Leu Asp Arg Asn Ser Arg Val Gln Val Gly Cys Arg Glu Leu Arg Ser
65                  70                  75                  80

Thr Lys Tyr Ile Ser Asp Gly Gln Cys Thr Ser Ile Ser Pro Xaa Lys
                85                  90                  95

Glu Leu Val Cys Ala Gly Glu Cys Leu Pro Leu Pro Val Leu Pro Asn
            100                 105                 110

Trp Ile Gly Gly Gly Tyr Gly Thr Lys Tyr Trp Ser Arg Arg Ser Xaa
        115                 120                 125

Gln Glu Trp Arg Cys Val Asn Asp Lys Thr Arg Thr Gln Arg Ile Gln
    130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Ser Lys His Ser Leu Ser
        195                 200                 205

<210> SEQ ID NO 217
<211> LENGTH: 168
<212> TYPE: PRT
<213> ORGANISM: Human

<400> SEQUENCE: 217

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
```

-continued

```
                20                  25                  30
Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys
                165
```

COMPOSITIONS AND METHODS FOR TREATING KIDNEY DISEASE

This application is a continuation-in-part of U.S. patent application Ser. No. 11/508,701 filed Aug. 23, 2006. U.S. patent application Ser. No. 11/508,701 is a continuation-in-part of U.S. patent application Ser. No. 10/464,368 filed Jun. 16, 2003, which claims priority to U.S. Provisional Application No. 60/388,970 filed Jun. 14, 2002. U.S. patent application Ser. No. 11/508,701 also claims priority to U.S. Provisional Application Ser. No. 60/710,803 filed Aug. 23, 2005.

BACKGROUND OF INVENTION

A. Field of the Invention

The present invention relates to compositions and methods for the prevention and treatment of renal damage. In particular, the invention relates to administration of novel therapeutics to subjects in order to prevent or treat renal degeneration or damage. These novel therapeutics include antibodies, peptides, and small molecules based upon the WISE/SOST family of proteins.

B. Background of the Invention

The mammalian renal system serves primary roles both in the removal of catabolic waste products from the bloodstream and in the maintenance of fluid and electrolyte balances in the body. Renal failures are, therefore, life-threatening conditions in which the build-up of catabolites and other toxins, and/or the development of significant imbalances in electrolytes or fluids, may lead to the failure of other major organs systems and death. Chronic renal failure is a debilitating and life-threatening disease for which no adequate treatment exists.

Tubular damage and interstitial fibrosis are the final common pathways leading to end stage renal disease. Irrespective of the nature of the initial renal injury, the degree of tubular damage parallels the impairment of renal function. Once nephronic degeneration or tubular damage is established, it cannot be reversed or repaired by currently available treatment, and renal function deteriorates to renal failure, which is often life threatening. Renal damage and failure can only be managed through dialysis or organ transplantation.

Dialysis dependency is one of the leading causes of morbidity and mortality in the world. Despite advancement in understanding the pathophysiology of renal diseases, the incidence of end-stage renal disease is increasing. Approximately 600 patients per million receive chronic dialysis each year in the United States, at an average cost approaching $60,000-$80,000 per patient per year. Of the new cases of end-stage renal disease each year, approximately 28-33% are due to diabetic nephropathy (or diabetic glomerulopathy or diabetic renal hypertrophy), 24-29% are due to hypertensive nephrosclerosis (or hypertensive glomerulosclerosis), and 15-22% are due to glomerulonephritis. The 5-year survival rate for all chronic dialysis patients is approximately 40%, but for patients over 65, the rate drops to approximately 20%.

A need remains, therefore, for treatments that will prevent the progressive loss of renal function which has caused almost two hundred thousand patients in the United States alone to become dependent upon chronic dialysis, and which results in the premature deaths of tens of thousands each year.

SUMMARY OF INVENTION

The present invention provides protein-based renal therapeutic agents for administration to subjects in, or at risk of, renal failure. The methods and compositions of the present invention may be used to prevent, inhibit, delay, or reverse nephronic degeneration, which otherwise leads to the need for renal replacement therapy to prevent death. Specifically, the present invention is directed to compositions and methods that regulate the interaction between SOST and WISE proteins with their natural receptors. Exemplary natural receptors for WISE and SOST proteins include, but are not limited to, LRP5, LRP6, and BMP molecules. Methods and compositions of the present invention therefore provide a therapy that may reverse nephronic degeneration and/or prevent the progressive loss of renal function, thereby preventing premature death.

Methods of the invention include administering a therapeutically effective amount of an antibody to a patient in which the antibody specifically binds a peptide having at least 75%, 80%, 85%, 90%, 95%, 99% or more identity to at least 5, 8, 10, 15, 20 or more contiguous amino acids of a developmental regulator and the antibody interferes with the interaction between at least two developmental regulators thereby providing nephron protection and/or regeneration. Exemplary developmental regulators include those molecules disclosed as SEQ ID NOS: 1-217.

In some embodiments of the invention, the developmental regulators are a ligand and the ligand's natural receptor. For example, the ligand may be WISE and a known WISE receptor, such as LRP5, LRP6, BMP2, or BMP7. Another exemplary pair is SOST protein and one or more of its known receptors, e.g., LRP5, LRP6, BMP6, or BMP7.

The invention also provides a pharmaceutical composition for administration to a subject that includes an antibody and optional excipient(s). Antibodies suitable for the present invention may be administered in a therapeutically effective amount resulting in an improvement of renal function by at least 10%, 15%, 20%, 25%, or more following renal insult, as measured by a standard assay of renal function. Examples of such assays are provided herein. For example, a suitable assay of renal function include, determining rates of increase in Blood Urea Nitrogen (BUN) levels, rates of increase in serum creatinine, static measurements of BUN, static measurements of serum creatinine, glomerular filtration rates (GFR), ratios of BUN/creatinine, and serum concentrations of sodium (Na+). Suitable excipients include, but are not limited to, saline, buffered saline, dextrose, water, glycerol, ethanol, and combinations thereof.

Antibodies of the invention may be monoclonal, polyclonal, humanized, or a fragment thereof (Fab or Fab$_2$), as described in greater detail, below. Preferably, antibodies of the present invention specifically bind a peptide having at least 75%, 80%, 85%, 90%, 95%, 99% or more identity to at least 5, 8, 10, 15, 20 or more contiguous amino acids of a developmental regulator and the antibody interferes with the interaction between at least two developmental regulators thereby providing nephron protection and/or regeneration. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; preferably SEQ ID NOS. 90-108, 215, and 216; more preferably, SEQ ID NOS. 19-89, 15-18, and 217; preferentially, SEQ ID NOS. 90-93, 215, and 216; alternatively, SEQ ID NOS. 15-20 and 217; more preferably, SEQ ID NOS. 92, 93, and 215; more preferably SEQ ID NOS. 15-18 and 217; ideally, SEQ ID NOS. 15-18. Alternatively, the antibody specifically binds a peptide having at least 75%, 80%, 85%, 90%, 95%, 99% or more identity to at least 5, 8, 10, 15, 20 or more contiguous amino acids of positions 50-62, 68-80, or 83-98 of SEQ ID NOS. 20, and 215-217.

The method and pharmaceutical composition of the invention may be administered to any subject receiving renal injury, chemical or physical insult resulting in apoptosis or necrosis of renal tissue, disease, or those otherwise at risk of chronic renal failure. For example, subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis.

The methods and compositions of the present invention may be utilized for any mammalian subject. For example, human subjects or patients, domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd Ed. 1994); *The Cambridge Dictionary of Science and Technology* (Walker ed., 1988); The Glossary of Genetics, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, *J., Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol* :5368, Zhu et al. (1997) *Protein Sci* 6:781, Hu et al (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al, *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

The term "insult" refers to any injury or damage to a cell or population of cells that results in cell death or apoptosis, necrosis, altered kidney function, or decreased kidney function. An insult may have a variety of causes including, but not limited to, disease, chemical injury, or physical injury.

The phrase "specifically binds" when referring to a protein or peptide, refers to a binding reaction that is determinative of the presence of the protein, in a heterogeneous population of proteins and other biologics. Thus, under designated immunoassay conditions, the specified antibodies bind to a particular protein sequence at least two times the background and more typically more than 10 to 100 times background.

Specific recognition by an antibody under such conditions requires an antibody that is selected for its specificity for a particular protein. For example, antibodies raised against a particular protein, polymorphic variants, alleles, orthologs, and conservatively modified variants, or splice variants, or portions thereof, can be selected to obtain only those polyclonal antibodies that are specifically immunoreactive with WISE/SOST-like peptides such as those exemplified by SEQ ID NOS: 2, 4, 6, 8, 10, 12, 14, 15-18, 20-82, 85-87, 91, 93, 95, 98, 101, 103, 105, 109-217 and not with other random proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

The terms "identical" or percent "identity," in the context of two or more nucleic acids or polypeptide sequences, refer to two or more sequences or subsequences that are the same or have a specified percentage of amino acid residues or nucleotides that are the same as measured using a BLAST or BLAST 2.0 sequence comparison algorithms with default parameters described below, or by manual alignment and visual inspection. Such sequences are said to be "substantially identical" when they have about 60% identity, preferably 70%, 75%, 80%, 85%, 90%, 91%, 92%, 93%, 94%, 95%, 96%, 97%, 98%, 99%, or higher identity over a specified region, once compared and aligned for maximum correspondence over a comparison window or designated region. This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

The phrase "conditions suitable for protein binding" refers to those conditions (in terms of salt concentration, pH, detergent, protein concentration, temperature, etc.) which allow for binding to occur between a protein and its binding partner in solution. The conditions are not so lenient that a significant amount of nonspecific protein binding occurs.

As used herein, the term "developmental regulators" refers to molecules associated with the Wnt and BMP signaling pathways. Specifically, the term refers to the ligands and receptors responsible for regulating the Wnt and BMP signaling pathways including, but not limited to, LRP5, LRP6, BMP2, BMP4, BMP6, and BMP7. For example, several of these developmental regulators are provided by SEQ ID NOs: 1-217 as presented in the present application.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 graphically illustrates inhibition of SOST association with LRP6. Relative LRP6 binding to variants of SOST was measured following immunoprecipitation. SOST variants M1, M2, M3, and M8 significantly exhibited reduced binding to LRP6 compared to wild type SOST.

DETAILED DESCRIPTION

I. Introduction

The present invention provides compositions and methods of using certain protein-based renal therapeutic agents that surprisingly prevent, inhibit, delay or alleviate the progressive loss of renal function. In a preferred embodiment, the present invention is suitable for treatment of renal disease.

In some forms, renal disease is caused by aberrant signal transduction during kidney development. The kidney develops from the ureteric bud, extending out from a pre-existing epithelial tube, giving rise to the branched collecting duct system while the surrounding metanephric mesenchyme undergoes mesenchymal-epithelial transition to form the proximal parts of the nephron. Signaling by members of the Wnt, BMP and FGF protein families, mediate this nephrogenesis by adjusting the balance between the ureteric bud epithelium, stromal and nephrogenic tissues. Inappropriate alteration of the balance of these signaling pathways, gives rise to renal disease. For example, over-activation of the Wnt pathway leads to cancer development (e.g. Wilms tumor), while inhibition of BMP signaling results in nephronic degeneration, both ultimately leading to renal failure.

WISE and/or SOST signaling also influences mature kidney tissue homeostasis, particularly in the case of renal damage or disease. In certain embodiments of the present invention, renal disease or damage is mitigated or reversed by administering to a patient antibodies that perturb or block the association of WISE and/or SOST to its receptor molecules in vivo. For example, administration of antibodies that mimic the WISE and/or SOST association with LRP5 or LRP6 may be used to subdue over-activated Wnt signaling in the treatment of kidney cancer. Alternatively, the association of WISE and/or SOST with BMP6, BMP7, and/or BMP2 may be inhibited to allow BMP signaling, which may result in protection from nephronic injury and/or promotion of nephronic regeneration.

II. Biological Assays of the Invention

The phrase "nephronic degeneration" refers to deterioration of an individual's kidney in which kidney or renal function is diminished as result of tissue necrosis or apoptosis by at least 5% preferably 10%, 15%, 20%, 25%, 30%, 40% 50% or more from the range of normal values medically determined for the individual. Nephronic degeneration can result from physical insult, chemical insult, or disease. The presence of nephronic degeneration can be measured by assays well known to those of ordinary skill of the art, such as elevation of serum creatinine levels or decrease in creatinine clearance (see, Brenner and Lazarus (1994), in HARRISON'S PRINCIPLES OF INTERNAL MEDICINE, 13th edition, Isselbacher et al., eds., McGraw Hill Text, N.Y.). Preferably a decrease of 5%, more preferably 10%, 15%, 20%, 25%, 30%, 40%, 50% or more of creatinine clearance compared to normal levels marks nephronic degeneration. Likewise, a 5% elevation of serum creatinine levels, more preferably 10%, 15%, 20%, 25%, 30%, 40%, 50% or more compared to normal levels indicates nephronic degeneration.

The phrase "nephron protection" refers to an in vivo phenomenon that protects against and prevents degeneration of nephronic or renal function caused by physical insult, chemical insult, or disease. As such, nephron protection refers to an in viva phenomenon that inhibits elevation of serum creatinine levels or decrease in creatinine clearance by at least 5% preferably 10%, 15%, 20%, 25%, 30%, 40% 50% or more from the range of elevated values medically determined for the individual. Nephron protection also encompasses regeneration or repair of degenerate nephronic function caused by tissue necrosis or apoptosis resulting from physical insult, chemical insult, or disease. The regeneration or repair of degenerate nephronic function can be measured by assays well known to those of ordinary skill of the art, such as serum creatinine levels or creatinine clearance. Preferably an increase of 5%, more preferably 10%, 15%, 20%, 25%, 30%, 40%, 50% or more of creatinine clearance compared to normal levels marks nephronic protection. Likewise, a 5% decrease of serum creatinine levels, more preferably a 10%, 15%, 20%, 25%, 30%, 40%, 50% or more compared to normal levels indicates nephronic protection.

Assays of renal function are well known to those of ordinary skill of the art and include, without being limited to, rates of increase in Blood Urea Nitrogen (BUN) levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, Brenner and Lazarus (1994), in HARRISON'S PRINCIPLES OF INTERNAL MEDICINE, 13th edition, Isselbacher et al., eds., McGraw Hill Text, N.Y.). Exemplary normal levels are as follows: serum creatinine levels of 0.8 to 1.4 mg/dL; BUN levels of 5 to 20 mg/dL; GFR score of 90 mL/min or more; BUN/Creatinine ratio of 10:1 to 20:1 and up to 30:1 in infants under 12 months of age; and serum sodium levels of 135 to 145 mEq/L. A skilled artisan will recognize that the normal ranges may vary with age, muscle mass, gender, weight, body surface area, and other characteristics. An "improvement" in one of the assays of renal function refers to an increase or decrease in level that is closer to the normal range. For example, a 10% improvement of a serum creatinine level of 0.2 mg/dL would be a serum creatinine level of 0.22 mg/dL, while a 10% improvement of a serum creatinine level of 3.0 mg/dL would be a serum creatinine level of 2.7 mg/dL.

III. Therapeutic Compositions

The present invention is directed to compositions and methods that regulate the interaction between SOST and WISE proteins with their natural receptors, particularly LRP5, LRP6, and BMP molecules. The renal therapeutic agents of the invention include, but are not limited to, peptides, proteins, antibodies, and small molecules derived from the WISE/SOST and LRP/BMP families and resultantly regulate Wnt and BMP signaling. For example, any peptide of at least 20, preferably 25, 30, 35, 40, 50 or more amino acids encoded by SEQ ID NO: 2, 4, 6, 8, 10, 12, 14, 15-18, 20-82, 85-87, 91, 93, 95, 98, 101, 103, 105, 109-217, or any fragment of any sequence thereof, may be used to raise antibodies, derive peptides, or derive small molecules suitable for antagonizing the interaction between SOST and WISE proteins with their natural receptors.

Such peptides may provide the basis of therapeutics by their inherent properties. For example, as inhibitors of renal damage, blocking peptides that antagonize the interaction between SOST and WISE proteins with their natural receptors may be useful. Further, peptides that activate SOST and WISE natural receptors by mimicking the necessary interaction between SOST or WISE and their natural receptors may also be useful. Exemplary antagonizing or activating peptides may include those provided by SEQ ID NOS: 21-82 or fragments of SEQ ID NOS: 2, 4, 6, 8, 10, 12, 14, 15-18, 20, 85-87, 91, 93, 95, 98, 101, 103, 105, 109-217.

A. Peptides and Proteins

Proteins and peptides useful to the invention may be isolated from natural sources, prepared synthetically or recombinantly, or any combination of the same using techniques well known to those of skill in the art. Generally, any purification protocol suitable for isolating proteins and known to those of skill in the art can be used. For example, affinity purification, column chromatography techniques, precipitation protocols and other methods for separating proteins may be used (see, e.g., Scopes, Protein Purification: Principles and Practice (1982); and U.S. Pat. No. 4,673,641). Further, peptides may be produced synthetically using solid phase techniques and other techniques known to those skilled in the art (see, Barany, G. and Merrifield, R. B. *Solid Phase Peptide Synthesis* in PEPTIDES, Vol. 2, Academic Press, New York, N.Y., pp. 100-118 (1980)). Peptides and proteins of the invention may also be available commercially, or may be produced commercially.

B. Antibodies

The renal therapeutic agents of the present invention may be antibodies that recognize developmental regulator proteins, polypeptides, amino acid sequences, or fragments thereof. Suitable antibodies include those that recognize the WISE/SOST and LRP/BMP families and resultantly regulate Wnt and BMP signaling, such as those described in U.S. application Ser. No. 11/508,701 and incorporated herein by reference. For example, antibodies of the invention will recognize proteins or amino acid sequences encoding developmental regulators or fragments thereof, such as, but not limited to, those provided by SEQ ID NOS: 2, 4, 6, 8, 10, 12, 14, 15-18, 20-82, 85-87, 91, 93, 95, 98, 101, 103, 105, 109-217. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; more preferably SEQ ID NOS. 90-108, 215, and 216; more preferably, SEQ ID NOS. 19-89, 15-18, and 217; more preferably, SEQ ID NOS. 90-93, 215, and 216; more preferably, SEQ ID NOS. 15-20 and 217; more preferably, SEQ ID NOS. 92, 93, and 215; more preferably SEQ ID NOS. 15-18 and 217; more preferably, SEQ ID NOS. 15-18. Alternatively, the antibody specifically binds a peptide having at least 75%, 80%, 85%, 90%, 95%, 9904 or more identity to at least 5, 8, 10, 15, 20 or more contiguous amino acids of positions 50-62, 68-80, or 83-98 of SEQ ID NOS. 20, and 215-217.

When the above family of amino acid sequences, including WISE and SOST, are allowed to bind to their natural receptors, renal regeneration is repressed. When the above-mentioned family of amino acid sequences are prevented from binding to their natural receptors, renal regeneration will increase. Thus, the present invention relates to tools and methods used to inhibit or mimic the binding of the WISE/SOST family to their natural receptors.

1. Antigen Specificity and Production

The present invention provides at least one antibody that inhibits interaction between Wnt or BMP antagonistic ligands (developmental regulators) with LRP or BMP receptors, thus promoting constitutive Wnt or BMP signaling and renal regeneration. Suitable antibodies are obtained by immunizing a host animal with peptides, or antigens, that are all or a portion of the subject protein of the presently claimed invention. The antigen may be the complete protein, or fragments and derivatives thereof. For example, a suitable antigen may have at least 75%, 80%, 85%, 90%, 95%, 98%, 99% or 100% identity to at least 5, 8, 10, 12, 15, 20, or 25 contiguous amino acids of a protein encoded by SEQ ID NOS: 2, 4, 6, 8, 10, 12, 14, 15-18, 20-82, 85-87, 91, 93, 95, 98, 101, 103, 105, 109-217. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; more preferably SEQ ID NOS. 90-108, 215, and 216; more preferably, SEQ ID NOS. 19-89, 15-18, and 217; more preferably, SEQ ID NOS. 90-93, 215, and 216; more preferably, SEQ ID NOS. 15-20 and 217; more preferably, SEQ ID NOS. 92, 93, and 215; more preferably SEQ ID NOS. 15-18 and 217; more preferably, SEQ ID NOS. 15-18. Alternatively, the antibody specifically binds a peptide having at least 75%, 80%, 85%, 90%, 95%, 99% or more identity to at least 5, 8, 10, 15, 20 or more contiguous amino acids of positions 50-62, 68-80, or 83-98 of SEQ ID NOS. 20, and 215-217.

Some exemplary embodiment of the present invention includes antibodies that inhibit, block, or otherwise interfere with the specific binding of an LRP or BMP molecule to a Wnt or BMP antagonistic ligand. A skilled artisan will recognize that an antigen may be selected to generate an antibody that interferes by specifically binding to the LRP or BMP molecule or by specifically binding to the Wnt or BMP antagonistic ligand. The selected antigen will result in an antibody that will specifically bind to WISE-like or SOST-like proteins and prevent the interaction of WISE-like or SOST-like proteins with LRP5, LRP6, BMP2, BMP6, or BMP7. in alternative examples, a selected antigen will result in an antibody that will specifically bind to LRP5, LRP6, or BMP molecules and prevent the interaction with WISE-like or SOST-like proteins.

Suitable amounts of well-characterized antigen for production of antibodies can be obtained using standard techniques known in the art such as, but not limited to, cloning or synthetic synthesis. Antigenic proteins can be obtained from transfected cultured cells that overproduce the antigen of interest. For example, expression vectors that have nucleotide sequences encoding an antigen of interest can be constructed, transfected into cultured cells, and then the antigen can be subsequently isolated using methods well-known to those skilled in the art (see, Wilson et al., *J. Exp. Med.* 173:137, 1991; Wilson et al., *J. Immunol.* 150:5013, 1993). Alternatively, DNA molecules encoding an antigen of choice can be obtained by synthesizing DNA molecules using mutually priming long oligonucleotides (see, Ausubel et al., (eds.), *Current Protocols In Molecular Biology*, pages 8.2.8 to 8.2.13, 1990; Wosnick et al., *Gene* 60:115, 1987; and Ausubel et al. (eds.), *Short Protocols In Molecular Biology*, 3rd Edition, pages 8-8 to 8-9, John Wiley & Sons, Inc., 1995). As a skilled artisan will recognize, established techniques using the polymerase chain reaction provide the ability to synthesize antigens (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263 268, Humana Press, Inc. 1993). Once produced, the antigen of choice is used to generate antigen specific antibodies.

2. Antibody Production

The present invention provides antibodies as renal therapeutic agents. It is envisioned that such antibodies include, but are not limited to, polyclonal, monoclonal, humanized, part human, or fragments thereof. A skilled artisan will appreciate the benefits and disadvantages of the type of antibody used for therapeutic treatment and will further recognize the selection is dependent upon the intended use.

a. Polyclonal Antibodies

Means for preparing and characterizing polyclonal antibodies are well known to those skilled in the art (see, e.g., *Antibodies: A Laboratory Manual*, Cold Spring Harbor Laboratory, 1988; incorporated herein by reference). For example, for the preparation of polyclonal antibodies, the first step is immunization of the host animal with the target antigen, where the target antigen will preferably be in substantially pure form, with less than about 1% contaminant. The antigen may include the complete target protein, fragments, or derivatives thereof. To prepare polyclonal antisera an animal is immunized with an antigen of interest, and antisera is collected from that immunized animal. A wide range of animal species can be used for the production of antisera. Typically the animal used for production of anti-antisera is a rabbit, mouse, rat, hamster, guinea pig or goat. Because of the relatively large blood volume of rabbits, a rabbit is a preferred choice for the production of polyclonal antibodies.

The amount of antigen used in the production of polyclonal antibodies varies upon the nature of the antigen as well as the animal used for immunization. A variety of routes can be used to administer the antigen of choice; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored. The animal can also be used to generate monoclonal antibodies, as is well known to those skilled in the art.

The immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis*; incomplete Freund's adjuvant; and aluminum hydroxide adjuvant.

It may also be desired to boost the host immune system, as may be achieved by associating the antigen with, or coupling the antigen to, a carrier. Exemplary carriers include keyhole limpet hemocyanin (KLH) and bovine serum albumin (BSA). Other albumins such as ovalbumin, mouse serum albumin or rabbit serum albumin can also be used as carriers. As is also known in the art, a given composition may vary in its immunogenicity.

b. Monoclonal Antibodies

Monoclonal antibodies (Mabs) may be readily prepared through use of well-known techniques to those skilled in the art, such as those exemplified in U.S. Pat. No. 4,196,265, incorporated herein by reference. Typically, this technique involves immunizing a suitable animal with the selected antigen. The antigen is administered in a manner effective to stimulate antibody-producing cells. Rodents such as mice and rats are preferred animals, however, the use of rabbit, sheep and frog cells is also possible.

By way of example, following immunization the somatic cells with the potential for producing antigen specific antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The anti-antigen antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984; each incorporated herein by reference). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

The heterogeneous cell population may be cultured in the presence of a selection medium to select out the hybridoma cells. A suitable selection medium includes an inhibitor of de novo synthesis, such as aminopterin in HAT medium, methotrexate in HMT medium, or azaserine in AzaH medium plus the necessary purine and/or pyrimidine salvage precursors (i.e. hypoxanthine and thymidine in HAT or HMT media; hypoxanthine in AzaH medium). Only cells capable of operating nucleotide salvage pathways are able to survive in the selection medium. The myeloma cells are defective in key enzymes of the salvage pathway, e.g., hypoxanthine phosphoribosyl transferase (HPRT), and cannot survive. The B cells can operate this pathway, but they have a limited life span in culture and generally die within about two weeks. Therefore, the only cells that can survive in the selective media are those hybrids formed from myeloma and B cells (hybridomas).

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-antigen reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual anti-antigen antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

c. Humanized Antibodies

Also of interest are humanized antibodies. Methods of humanizing antibodies are known in the art. The humanized antibody may be the product of an animal having transgenic human immunoglobulin constant region genes (see for example International Patent Applications WO 90/10077 and WO 90/04036, both incorporated herein by reference). Alternatively, the antibody of interest may be engineered by recombinant DNA techniques to substitute the CH1, CH2, CH3, hinge domains, and/or the framework domain with the corresponding human sequence (see WO 92/02190 and incorporated herein by reference).

The use of Ig cDNA for construction of chimeric immunoglobulin genes is known in the art (Liu et al. *P.N.A.S.* 84:3439, 1987 and incorporated herein by reference). mRNA is isolated from a hybridoma or other cell producing the antibody and used to produce cDNA. The cDNA of interest may be amplified by the polymerase chain reaction using specific primers (see U.S. Pat. Nos. 4,683,195 and 4,683,202, both incorporated herein by reference). Alternatively, a library is made and screened to isolate the sequence of interest. The DNA sequence encoding the variable region of the antibody is then fused to human constant region sequences. The sequences of human constant region genes may be found in Kabat et al. Sequences of Proteins of Immunological Interest, N.I.H. publication no. 91-3242, 1991 and incorporated herein by reference. Human C region genes are readily available from known clones. The chimeric, humanized antibody is then expressed by conventional methods known to those of skill in the art.

d. Antibody Fragments

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule. The following patents and patent applications are specifically incorporated herein by reference for the preparation and use of functional, antigen-binding regions of antibodies, including scFv, Fv, Fab', Fab and F(ab')$_2$ fragments: U.S. Pat. Nos. 5,855,866; 5,965,132; 6,051,230; 6,004,555; and 5,877,289.

Also contemplated are diabodies, which are small antibody fragments with two antigen-binding sites. The fragments may include a heavy chain variable domain ($V_H$) connected to a light chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Techniques for generating diabodies are well known to those of skill in the art and are also described in EP 404,097 and WO 93/11161, each specifically incorporated herein by reference. Also, linear antibodies, which can be bispecific or monospecific, may include a pair of tandem Fd segments ($V_H C_{H1}$-$V_H C_{H1}$) that form a pair of antigen binding regions may be useful to the invention as described in Zapata et al., (1995), and incorporated herein by reference.

C. Compositions

The renal therapeutic agents contemplated herein can be expressed from intact or truncated genomic or cDNA or from synthetic DNAs in prokaryotic or eukaryotic host cells by techniques well known to those of skill in the art. Exemplary host cells include, without limitation, prokaryotes including *E. coli*, or eukaryotes including yeast, *Saccharomyces*, insect cells, or mammalian cells, such as CHO, COS or BSC cells. One of ordinary kill in the art will appreciate that other host cells can be used to advantage.

The term "construct" as used herein refers to a nucleic acid sequence containing at least one polynucleotide encoding a polypeptide of the invention operably linked or fused to additional nucleic acids. Such constructs include vectors, plasmids, and expression cassettes encoding at least one polynucleotide encoding a polypeptide of the invention. It is also envisioned that constructs could be polynucleotides encoding a polypeptide of the invention fused to other protein coding sequence to generate fusion proteins as known to those of skill in the art.

Constructs can be inserted into mammalian host cells by methods known to those of skill in the art including, but not limited to, electroporation, transfection, microinjection, micro-vessel transfer, particle bombardment, biolistic particle delivery, liposome mediated transfer and other methods described in *Current Protocols in Cell Biology*, Unit 20, pub. John Wiley & Sons, Inc., 2004 and incorporated herein by reference.

III. Therapeutic Uses

A. Subjects for Treatment

Renal therapeutic agents of the invention may be used in subjects that have received renal injury, or those at risk of chronic renal failure. As used herein, a subject is said to be in, or at risk or, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

The methods and compositions of the present invention may be utilized for any mammalian subject. Such mammalian subjects include, but are not limited to, human subjects or patients. Exemplary subjects may also include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

B. Excipients

The renal therapeutic agents of the invention, alone or conjugated, may be formulated according to methods known to those skilled in the art to prepare pharmaceutically useful compositions, whereby the therapeutic agents are combined in a mixture with a pharmaceutically acceptable carrier or excipient. A composition is said to be a "pharmaceutically acceptable carrier" if its administration can be tolerated by a recipient patient and preserves the activity of the active component, in this case the renal therapeutic agent. Exemplary carriers include, but not are limited to, saline, buffered saline, dextrose, water, glycerol, ethanol, and combinations thereof. The Formulation should suit the mode of administration.

Other suitable carriers are well known to those skilled in the art (see, REMINGTON'S PHARMACEUTICAL SCIENCES, 19th Ed., 1995). Upon formulation, the antibody or immunoconjugate solutions will be administered in a manner compatible with the dosage formulation and in such amount as is therapeutically effective.

C. Dosage

In general, the dosage of administered renal therapeutic agents will vary depending upon such factors as the patient's age, weight, height, sex, general medical condition and previous medical history. For example, it is typically desirable to provide the recipient with a dosage of an antibody component, which is in the range of from about 1 pg/cg to 10 mg/kg (amount of agent/body weight of patient), although a lower or higher dosage also may be administered as circumstances dictate. Range finding studies may be conducted to determine appropriate dosage by techniques known to those skilled in the all and as described in *Current Protocols in Pharmacology*, Unit 10, pub. John Wiley & Sons, 2003 and incorporated herein by reference. A skilled artisan will recognize the therapeutically effective amount for each active compound may vary with factors including, but not limited to, the activity of the compound used, stability of the active compound in the recipient's body, the total weight of the recipient treated, the route of administration, the ease of absorption, distribution, and excretion of the active compound by the recipient, the age and sensitivity of the recipient to be treated, the type of tissue, and the like.

For purposes of therapy, renal therapeutic agents are administered to a patient in a therapeutically effective amount in a pharmaceutically acceptable carrier. In this regard, a "therapeutically effective amount" is one that is physiologically significant. An agent is physiologically significant if its presence results in a detectable change in the physiology of a recipient patient. In the present context, an agent is physiologically significant if its presence results in a clinically significant improvement in an assay of renal function when administered to a mammalian subject (e.g., a human patient). Such assays of renal function are well known to those of skill in the art and include, without being limited to, rates of increase in Blood Urea Nitrogen (BUN) levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, Brenner and Lazarus (1994), in HARRISON'S PRINCIPLES OF INTERNAL MEDICINE, 13th edition, Isselbacher et al., eds., McGraw Hill Text, N.Y.)

Additional pharmaceutical methods may be employed to control the duration of action of an antibody in a therapeutic application. Control release preparations can be prepared through the use of polymers to complex or adsorb the renal therapeutic agent. For example, biocompatible polymers include matrices of poly(ethylene-co-vinyl acetate) and matrices of a polyanhydride copolymer of a stearic acid dimer and sebacic acid (Sherwood et al., *Bio/Technology;* 10:1446, 1992). The rate of release of an agent from such a matrix depends upon the molecular weight of the protein, the amount of agent within the matrix, and the size of dispersed particles (Saltzman et al., *Biophys. J* 55:163, 1989; Sherwood et al., *Bio/Technology* 10:1446, 1992). Other solid dosage forms are described in REMINGTON'S PHARMACEUTICAL SCIENCES, 19th ed. (1995) and can be prepared by techniques known to those skilled in the art.

D. Routes of Administration

Administration of renal therapeutic agents to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing antibodies.

E. Methods for Testing Renal Therapeutic Agents

The renal therapeutic agents of the present invention may be tested in animal models of chronic renal failure or nephronic degeneration. Mammalian models of nephronic degeneration in, for example, mice, rats, guinea pigs, cats, dogs, sheep, goats, pigs, cows, horses, and non-human primates, may be created by causing an appropriate direct or indirect injury or insult to the renal tissues of the animal. For example, animal models of nephronic degeneration may be created by administering cisplatin, which causes nephrotoxicity and reduced creatinine clearance. Animal models of nephronic degeneration may also be created by performing a partial (e.g., 5/6) nephrectomy which reduces the number of function nephron units to a level which initiates compensatory renal hypertrophy, further nephron loss, and the progressive decline in renal function (see, Vukicevic, et al., *J. Bone Mineral Res.* 2:533, 1987). Alternatively, animal models of renal cell carcinoma may be generated by subcapsular renal injection of renal carcinoma (RENCA) cells that results in the development of primary tumors with subsequent development of metastases in the lungs, lymph nodes, and spleen (see, Hillman, G. G., Droz, J., and Haas, G. H. *In Vivo,* 8: 77-80, 1994). The above-described animal models may be generated by techniques well-known to those of skill in the art.

The renal therapeutic agents may be administered to the above-described animal models and markers of renal function can be monitored (see, Examples 1-3). Preferably kidney function is determined using markers of renal function such as Blood Urea Nitrogen (BUN) levels, serum creatinine levels, or glomerular filtration. Exemplary renal therapeutic agents will result in a decrease of BUN or serum creatinine levels or increase in glomerular filtration rate compared to control animals. Control animals will be animal models treated with a control solution not containing the renal therapeutic agent being tested, preferably a non-irritating buffer solution or other carrier.

IV. Kits

The present invention provides articles of manufacture and kits containing materials useful for treating the pathological conditions described herein. The article of manufacture may include a container of a medicament as described herein with a label. Suitable containers include, for example, bottles, vials, and test tubes. The containers may be formed from a variety of materials such as glass or plastic. The container holds a composition having an active agent which is effective for treating, for example, diseases characterized by nephronic degeneration. Alternatively, the container may hold a composition that includes a nephronic degeneration-inducing agent. The active agent in the composition is a renal therapeutic agent of the invention, including a peptide, protein, antibody, small molecule, or an agent such as a vector or cell preparation capable of allowing production of a renal therapeutic agent in vivo. The label on the container indicates that the composition is used for treating nephronic degenerative diseases, or malignant diseases, and may also indicate directions for administration and monitoring techniques, such as those described above.

The kit of the invention includes the container described above and a second container, which may include a pharmaceutically acceptable diluent. It may further include other materials desirable from a commercial and user standpoint, including other buffers, diluents, filters, needles, syringes, and package inserts with instructions for use.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of non-critical parameters that could be changed or modified to yield essentially similar results.

Example 1

WISE/SOST Antibody Production

Figure 1:
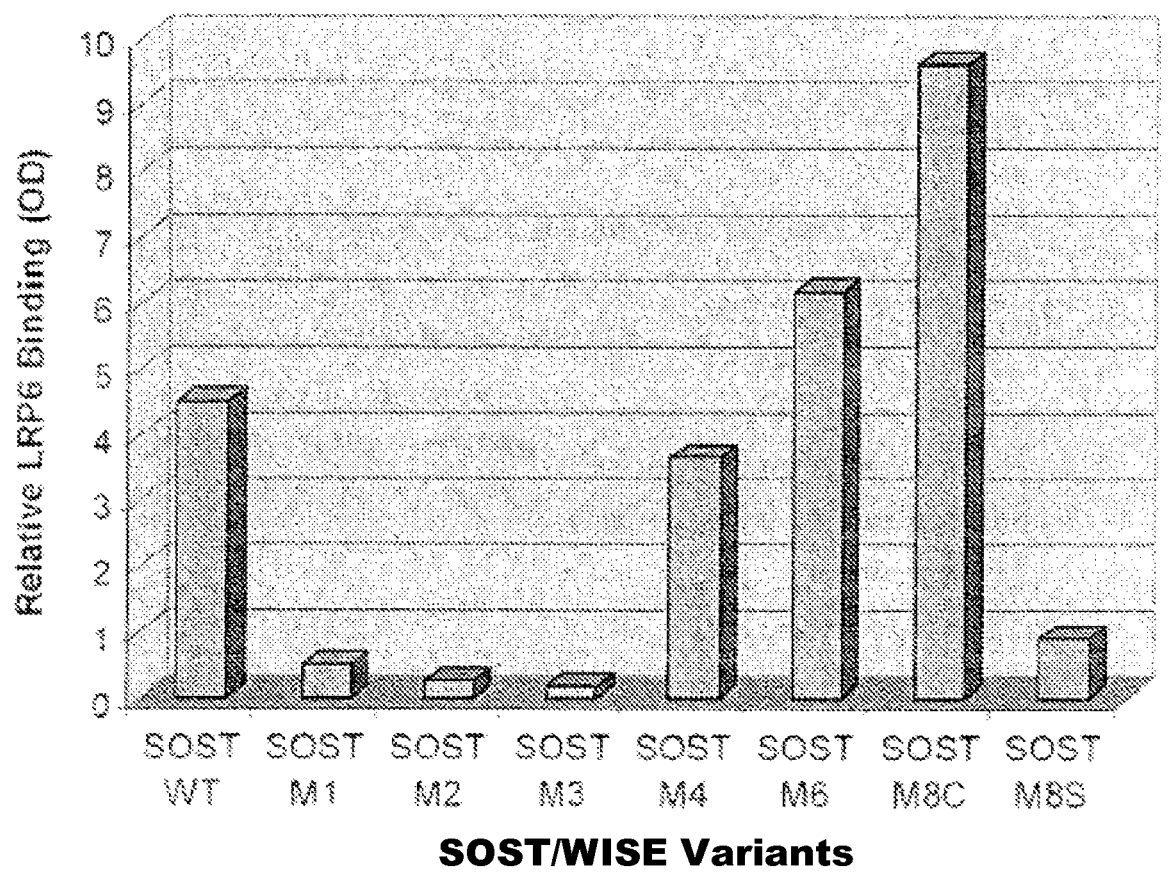

SOST and Wise both share the same gene structure, and produce a secreted protein whose second exon encodes a cystein knot. Molecular dissection of SOST at the amino acid level revealed putative LRP5/6 binding sites located in the first arm of the cystein knot. An immunoprecipitation assay of Flag tagged SOST variants and LRP6 was used to confirm which of these sites were necessary for LRP5/6 binding. Variants of SOST were generated with mutations at positions 60-62 (M1), 78-81 (M2), 89-90 (M3), 100-103 (M4), 140-143 (M7), and 162-166 (M8s). An immunoprecipitated western blot of Flag tagged SOST was mixed with LRP6-IgG and was quantified using phosphor-imager and its software ImageQuant. SOST variants M1, M2 and M3 showed a significant loss of binding ability to LRP6 (FIG. 1A, thus indicating potential sites for mediating the block between SOST and its natural binding partners including LRP5/6, BMP6, and BMP7.

In order to block the binding of SOST to LRP 5/6, BMP6, or BMP7 inhibitory antibodies were generated that recognize the altered amino acids of SOST variants M1, M2, and M3. Specific epitopes targeting these amino acids were identified using antigenic hydrophobic plots. These plots revealed that the best sites for generation of an antibody were between amino acids 50-62, 68-80, and 83-98 of SEQ ID NO. 215 and 217. The resultant peptides selected as antigens to produce antibodies are listed in SEQ ID NOS 15-18 and were used to generate monoclonal antibodies.

The peptides of SEQ ID NO 15-18 were used to immunize mice. Following immunization, B lymphocytes (B cells) were obtained from peripheral blood samples. The B cells from the immunized mice were then fused with murine myeloma cells to produce hybridomas. The cells were cultured in HAT medium with hypoxanthine and thymidine to select out the hybridoma cells. Hybridomas were then cultured by single-clone dilution in microtiter plates, followed by ELISA testing of the individual clonal supernatants for desired anti-antigen reactivity. There were 27 ELISA positive monoclonal antibodies generated against SOST.

Example 2

Acute Renal Failure Treatment

Acute renal failure manifests itself immediately following renal insult or injury. Therapeutics of the present invention may be analyzed for use as a treatment for preventing or reversing acute renal failure.

Mice subjected to partial nephrectomies or decapsulation may be used as models of nephronic degeneration to test renal therapeutic agents of the invention (see, Vukicevic, et al., *J. Bone Mineral Res.* 2:533, 1987). A partial nephrectomy involves removing one kidney and ⅔ of the remaining kidney. After initial dramatic increases in plasma creatinine and BUN levels indicating an acute failure phase, the levels decline to an elevated level compared to normal levels. Approximately two weeks following surgery, the elevated level gradually increases with time as the animal progresses to chronic renal failure. Decapsulation is a mock surgery in which the kidneys are decapsulated but no renal tissue is removed or nephronic injury introduced. Decapsulated mice may be used as controls for kidney functionality comparison.

To determine if a renal therapeutic agent of the invention can prevent or delay the effects of acute renal failure, nephrectomized and decapsulated mice that have immediately recovered from their respective surgeries may be used. Mice may be divided into six groups as follows: 1) nephrectomized, receiving renal therapeutic agent; 2) nephrectomized, receiving vehicle buffer only; 3) nephrectomized, receiving no treatment; 4) decapsulated, receiving renal therapeutic agent; 5) decapsulated, receiving vehicle buffer only; and 6) decapsulated, receiving no treatment. Group one can be further divided into mice receiving 1, 3, 10, or 50 µg/kg body weight of renal therapeutic agent. Prior to or during the acute failure phase, nephrectomized mice may be administered their respective treatment by intraperitoneal injection twice daily for at least three days. Serum creatinine levels should be monitored prior to surgery, immediately following surgery, each day of treatment, and for each of at least four days following the last injection.

A decrease in serum creatinine levels in nephrectomized mice treated with a therapeutic agent of the invention may indicate a successful candidate for further testing of preventing nephronic degeneration or inducing nephronic regeneration. An increase in serum creatinine levels beyond increases of serum creatinine levels of vehicle-only treated mice may indicate a therapeutic agent capable of inducing nephronic degeneration. Such an agent may be useful in treating renal cell carcinoma or other kidney cancer type.

Example 3

Chronic Renal Failure Treatment

Chronic renal failure manifests itself progressively following an initial acute renal failure phase or renal insult without concomitant acute renal failure. Therapeutics of the present invention may be analyzed for use as a treatment for preventing or reversing chronic renal failure.

To determine if a therapeutic agent of the invention may prevent the development of chronic renal failure, nephrectomized and decapsulated mice that have recovered from their respective surgeries for at least two weeks may be used. Animals surviving the surgery for two weeks are past the acute renal failure phase and have not yet entered chronic renal failure.

Mice may be divided into six groups as follows: 1) nephrectomized, receiving renal therapeutic agent; 2) nephrectomized, receiving vehicle buffer only; 3) nephrectomized, receiving no treatment; 4) decapsulated, receiving renal therapeutic agent; 5) decapsulated, receiving vehicle buffer only; and 6) decapsulated, receiving no treatment. Group one can be further divided into mice receiving 1, 3, 10, or 50 µg/kg body weight of renal therapeutic agent. Mice may be treated intraperitoneally at least three times per week for a period of approximately 6-9 weeks. Serum creatinine levels should be monitored prior to treatment, during the treatment period, and at least 1 week following the treatment period.

During weeks 1-5 of treatment, nephrectomized mice may exhibit elevated serum creatinine levels compared to decapsulated mice. The amount of elevation between the groups of nephrectomized mice may correlate with the course of treatment used. If the serum creatinine levels are less elevated with increasing amounts of the renal therapeutic agent being tested, then the agent may be a successful candidate for further tests of preventing nephronic degeneration and inducing nephronic regeneration. If the serum creatinine levels become increasingly elevated with increasing amounts of the renal therapeutic agent in decapsulated mice, then the agent may be a nephronic degeneration inducing agent. Such an agent may be useful in treating renal cell carcinoma or other kidney cancer type.

Example 4

Renal Cell Carcinoma Treatment

Constitutive activation of the Wnt signaling pathway may be involved in the development of renal cell carcinoma and other kidney cancer types. The renal therapeutic agents of the invention that result in ectopic activation of the Wnt signaling pathway via interaction with the natural receptors of WISE and SOST may be useful in therapies treating renal cell carcinoma or other kidney cancer types. Therapeutics of the present invention may be analyzed for use as a treatment for preventing or reversing kidney cancer types.

To investigate novel therapeutic strategies for the treatment of human renal cell carcinoma, such as adoptive immunotherapy or cytokine therapy, murine renal cell carcinoma has been a particularly suitable animal model for assessing novel therapeutic approaches (Sayers, T. J., Wiltrout, T. A., McCormick, K., Husted, C., and Wiltrout, R. H., *Cancer Res.*, 50: 5414-5420, 1990; Salup, R. R., and Wiltrout, R. H. *Cancer Res.*, 46: 3358-3363, 1986). In this model, primary kidney tumors are induced by subcapsular renal injection of renal carcinoma (RENCA) cells with subsequent development of metastases in the lungs, lymph nodes, and spleen (Hillman, G. G., Droz, J., and Haas, G. H. *In Vivo*, 8: 77-80, 1994).

Murine RENCA cells originally obtained from a tumor that arose spontaneously in the kidney of BALB/c mice may be injected into BALB/c mice to generate a renal cell carcinoma model. Histologically, RENCA is a granular cell type adenocarcinoma, which is pleomorphic with large nuclei. Monolayers of murine RENCA cells may be grown in RPMI 1640 with phenol red supplemented with 10% FCS, 2 mM L-glutamine, 100 units penicillin/ml, and 100 µg of streptomycin/ml. RENCA cells may be cultured in a humidified atmosphere of 95% air and 5% carbon dioxide at 37° C.

Female BALD/c mice approximately 6-8 weeks of age (approximate weight, 20 g) may be injected with RENCA cells in 0.2-ml aliquots into the subcapsular space of the left kidney performed through a flank incision after the animals are anesthetized with 0.5-1.5 volume percent isoflurane, which may be used in combination with an oxygen flow of 1.5 l/min. The subcapsular renal injection of RENCA cells in a syngeneic BALB/c mouse may be followed by the progressive development of a primary tumor mass in the left kidney. One week after application, the primary tumor may be macroscopically visible; after 10 days, spontaneous metastases may develop in the regional lymph nodes, in the lung, the peritoneum, and the liver, allowing the RENCA model to be staged similarly to human renal cell carcinoma. The mean survival time of RENCA-bearing mice may be 32 days after RENCA cells are injected.

Treatments with a renal therapeutic agent of the invention or vehicle only may be initiated 1 day after tumor cell inoculation into the subcapsular space of the left kidney. Mice receiving the renal therapeutic agent may receive about 1, 3, 10, or 50 µg/kg body weight of the renal therapeutic agent intraperitoneally at least three times per week for a period of approximately 6-9 weeks. Serum creatinine levels should be monitored prior to treatment, during the treatment period, and at least 1 week following the treatment period. Animal weights should be taken every other day.

Two or 3 weeks after starting treatment, 6 or 10 mice, respectively, may be sacrificed in each group for determination of weight and volume of primary tumors, weight, and number of metastasis of the lung and metastasis formation in the abdominal lymph nodes. The volumes of primary tumors taken macroscopically may be calculated by taking and multiplying the distances of all three dimensions. The number of metastases in the lung and abdominal lymph nodes may be counted using a dissection microscope. In the abdominal cave, all visible lymph nodes may be counted for detection of metastasis, knowing that in healthy animals visible lymph nodes are usually absent. More animals may be sacrificed at later time points to monitor the progression or regression of tumor development.

A renal therapeutic agent of the invention that results in a significant decrease in primary tumor size or number of metastasis compared to mice treated with vehicle only may be successful candidates for renal cell carcinoma therapy. Agents that do not result in a significant decrease or result in a significant increase in primary tumor size or number of metastasis may be successful candidates for preventing nephronic degeneration or promoting nephronic regeneration.

SEQUENCE LISTING

The Sequence Listing, in computer readable form (CRF), is submitted on compact disc, and is hereby incorporated by reference into this patent application. A total of 217 sequences are being submitted.

What is claimed is:

1. A method for treating nephronic degeneration comprising administering to a patient a composition comprising a therapeutically effective amount of an antibody that specifically binds a peptide selected from the group consisting of SEQ ID NOS: 15-18, and 217, wherein the antibody interferes with the interaction between SOST and a SOST binding partner selected from the group consisting of LRP5, LRP6, and BMP.

2. The method of claim 1, wherein a cause of the nephronic degeneration comprises chemical insult, physical insult, or disease that results in apoptosis or necrosis.

3. The method of claim 1, wherein the antibody is a monoclonal antibody.

4. The method of claim 1, wherein the antibody is a Fab or Fab$_2$ fragment.

5. The method of claim 1, wherein the antibody specifically binds SOST and the binding of the antibody to SOST prevents SOST interaction with LRP5 or LRP6 under conditions suitable for protein binding.

6. The method of claim 1, wherein the antibody specifically binds SOST and the binding of the antibody to SOST prevents SOST interaction with BMP under conditions suitable for protein binding.

* * * * *